US009889135B2

(12) United States Patent
Koff et al.

(10) Patent No.: US 9,889,135 B2
(45) Date of Patent: Feb. 13, 2018

(54) COMPANION DIAGNOSTIC FOR CDK4 INHIBITORS

(71) Applicant: Memorial Sloan-Kettering Cancer Center, New York, NY (US)

(72) Inventors: Andrew Koff, Westbury, NY (US); Aimee Crago, New York, NY (US); David Liu, Elmhurst, NY (US); Marta Kovatcheva, New York, NY (US); Samuel Singer, New York, NY (US); Gary K. Schwartz, New York, NY (US); Mark A. Dickson, New York, NY (US); Mary Elizabeth Klein, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 14/884,329

(22) Filed: Oct. 15, 2015

(65) Prior Publication Data
US 2016/0030433 A1 Feb. 4, 2016

Related U.S. Application Data

(63) Continuation of application No. PCT/US2014/034399, filed on Apr. 16, 2014.
(Continued)

(51) Int. Cl.
*A61P 35/00* (2006.01)
*A61K 31/519* (2006.01)
(Continued)

(52) U.S. Cl.
CPC .......... *A61K 31/519* (2013.01); *C12Q 1/6886* (2013.01); *G01N 33/573* (2013.01);
(Continued)

(58) Field of Classification Search
CPC .. A61K 31/519; G01N 33/573; G01N 33/574; G01N 33/57496; G01N 33/57484;
(Continued)

(56) References Cited

U.S. PATENT DOCUMENTS 6,630,464 B1 10/2003 Kelley et al.
6,818,663 B2 11/2004 Chu et al.
(Continued)

FOREIGN PATENT DOCUMENTS

EP 1309621 B1 4/2010

OTHER PUBLICATIONS

Adams, "Healing and Hurting: Molecular Mechanisms, Functions, and Pathologies of Cellular Senescence," Molecular Cell 36:2-14 (2009).
(Continued)

*Primary Examiner* — T. Victor Oh
(74) *Attorney, Agent, or Firm* — Baker Botts L.L.P.

(57) ABSTRACT

The present invention relates to the use of one or more biomarkers to evaluate the likelihood that a CDK4 inhibitor would produce an anti-cancer effect in a subject. It is based, at least in part, on the discovery that cancer treatment with a CDK4 inhibitor is more effective where treated cancer cells undergo cellular senescence rather than a transient cell cycle arrest, where cellular senescence is associated with decreased MDM2 protein level. Accordingly, in non-limiting embodiments, the present invention provides for methods, compositions, and kits for a companion diagnostic for CDK4 inhibitors, and in particular, to the use of MDM2 expression as a biomarker for the likelihood that a cancer can be successfully treated by CDK4 inhibition.

10 Claims, 35 Drawing Sheets

Related U.S. Application Data

Figure 6B:
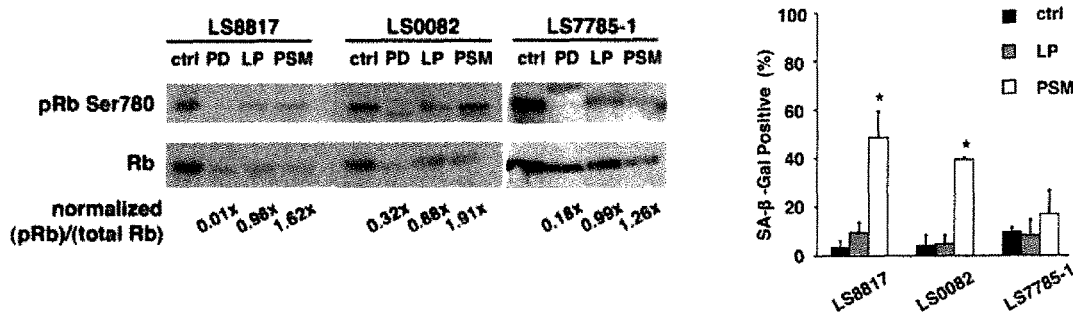

(60) Provisional application No. 61/812,412, filed on Apr. 16, 2013, provisional application No. 61/893,755, filed on Oct. 21, 2013.

(51) Int. Cl.
*C12Q 1/68* (2006.01)
*G01N 33/574* (2006.01)
*G01N 33/573* (2006.01)

(52) U.S. Cl.
CPC . *G01N 33/57484* (2013.01); *G01N 33/57496* (2013.01); *C12Q 2563/131* (2013.01); *G01N 2333/9015* (2013.01); *G01N 2800/52* (2013.01)

(58) Field of Classification Search
CPC ....... G01N 2333/9015; G01N 2800/52; C12Q 1/68; C12Q 1/6886; C12Q 2563/131; A61P 35/00
USPC .................................. 514/252.1, 19.3, 19.4
See application file for complete search history.

(56) References Cited

U.S. PATENT DOCUMENTS

| | | |
|---|---|---|
| 2011/0152244 A1 | 6/2011 | Besong et al. |
| 2012/0207763 A1 | 8/2012 | Brain et al. |
| 2012/0244110 A1 | 9/2012 | Chen et al. |

OTHER PUBLICATIONS

Aksoy et al., "The atypical E2F family member E2F7 couples the p53 and RB pathways during cellular senescence," Genes & Development 26:1546-1557 (2012).
Ambrosini et al., "Mouse double minute antagonist Nutlin-3a enhances chemotherapy-induced apoptosis in cancer cells with mutant p53 by activating E2F1," Oncogene 26:3473-3481 (2007).
Anders et al., "A Systematic Screen for CDK4/6 Substrates Links FOXM1 Phosphorylation to Senescence Suppression in Cancer Cells," Cancer Cell 20(5):620-634 (2011).
Barretina et al., "Subtype-specific genomic alterations define new targets for soft-tissue sarcoma therapy," Nature Genetics 42(8):715-721 (2010).
Brooks et al., "How does SIRT1 affect metabolism, senescence and cancer?," Nature Rev. Cancer 9(2):123-128 (2009).
Brooks et al., "The p53—Mdm2—HAUSP complex is involved in p53 stabilization by HAUSP," Oncogene 26(51):7262-7266 (2007).
Campisi J., "The Biology of Replicative Senescence," Eur. J. Cancer 33(5):703-709 (1997).
Campisi, J., "Cellular senescence: putting the paradoxes in perspective," Curr Opin Genet Dev. 21(1):107-112 (2011).
Capparelli et al., "CDK inhibitors (p 16/p19/p21) induce senescence and autophagy in cancer-associated fibroblasts, "fueling" tumor growth via paracrine interactions, without an increase in neo-angiogenesis," Cell Cycle 11(19):3599-3610 (2012).
Chan et al., "Novel ARF/p53-independent senescence pathways in cancer repression," J. Mol. Med (Berl) 89(9):857-867 (2011).
Chappell et al., "Ras/Raf/MEK/ERK and PI3K/PTEN/Akt/mTOR Inhibitors: Rationale and Importance to Inhibiting These Pathways in Human Health," Oncotarget 2(3):135-164 (2011).
Cheok et al., "Translating p53 into the clinic," Nat. Rev. Clin. Oncol. 8:25-37 (2011).
Chicas et al., "Dissecting the unique role of the retinoblastoma tumor suppressor during cellular senescence," Cancer Cell 17(4):376-387 (2010).
Ciznadija et al., "Hdm2- and proteasome-dependent turnover limits p21 accumulation during S phase," Cell Cycle 10(16):2714-2723 (2011).
Collado et al., "Senescence in tumours: evidence from mice and humans," Nat Rev Cancer 10(1):51-57 (2010).
Coppe et al., "The Senescence-Associated Secretory Phenotype: the Dark Side of Tumor Suppression," Annu Rev Pathol. 5:99-118 (2010).
Courtois-Cox et al., "Many roads lead to oncogene-induced senescence," Oncogene 27: 2801-2809 (2008).
Davalos et al., "Senescent cells as a source of inflammatory factors for tumor progression," Cancer Metastasis Rev 29:273-283 (2010).
Dean et al., "Therapeutic response to CDK4/6 inhibition in breast cancer defined by ex vivo analyses of human tumors," Cell Cycle 11(14):2756-2761 (2012).
Dickson et al., "Phase II Trial of the CDK4 Inhibitor PD0332991 in Patients with Advanced CDK4-Amplified Well-Differentiated or Dedifferentiated Liposarcoma," Journal of Clinical Oncology, 31(16):2024-2028 (2013).
Favaro et al., "Glucose Utilization via Glycogen Phosphorylase Sustains Proliferation and Prevents Premature Senescence in Cancer Cells," Cell Metabolism 16:751-764 (2012).
Finn et al., "PD 0332991, a selective cyclin D kinase 4/6 inhibitor, preferentially inhibits proliferation of luminal estrogen receptor-positive human breast cancer cell lines in vitro," Breast Cancer Research 11:R77 (2009).
Foo et al., "Ubiquitination and Degradation of the Anti-apoptotic Protein ARC by MDM2," The Journal of Biological Chemistry 282(8):5529-5535 (2007).
Fry et al., "Specific inhibition of cyclin-dependent kinase 4/6 by PD 0332991 and associated antitumor activity in human tumor xenografts," Molecular Cancer Therapeutics 3(11):1427-1438 (2004).
Goentoro et al., "Evidence that fold-change, and not absolute level, of β-catenin dictates Wnt signaling," Mol Cell. 36(5):872-884 (2009).
Guha, "Blockbuster dreams for Pfizer's CDK inhibitor," Nat Biotechnol 31(3):187 (2013).
Halvorsen et al., "Thiazolidinediones and Glucocorticoids Synergistically Induce Differentiation of Human Adipose Tissue Stromal Cells: Biochemical, Cellular, and Molecular Analysis," Metabolism 50(4):407-413 (2001).
Haupt et al., "Mdm2 promotes the rapid degradation of p53," Nature 387:296-299 (1997).
Honda et al., "Oncoprotein MDM2 is a ubiquitin ligase E3 for tumor suppressor p53," FEBS Letters 420:25-27 (1997).
Hsieh et al., "RB Regulates the Stability and the Apoptotic Function of p53 via MDM2," Molecular Cell 3:181-193 (1999).
International Search Report dated Sep. 15, 2014 in International Application No. PCT/US14/34399.
Inuzuka et al., "Phosphorylation by Casein Kinase I Promotes the Turnover of the Mdm2 Oncoprotein via the SCF(beta-TRCP) Ubiquitin Ligase," Cancer Cell 18(2):147-159 (2010).
Italiano et al., "Clinical and Biological Significance of CDK4 Amplification in Well-Differentiated and Dedifferentiated Liposarcomas," Clinical Cancer Research 15:5696-5703 (2009).
Iwakuma et al., "MDM2, An Introduction," Mol. Cancer Research, 1(14):993-1000 (2003).
Jackman et al., "Impact of Epidermal Growth Factor Receptor and KRAS Mutations on Clinical Outcomes in Previously Untreated Non-Small Cell Lung Cancer Patients: Results of an Online Tumor Registry of Clinical Trials," Clinical Cancer Research, 15(16):5267-5273 (2009).
Janku et al., "PIK3CA Mutations in Patients with Advanced Cancers Treated with PI3K/AKT/mTOR Axis Inhibitors," Molecular Cancer Therapeutics, 10(3):558-565 (2011).
Jensen et al., "STRING 8—a global view on proteins and their functional interactions in 630 organisms," Nucleic Acids Research 37:D412-416 (2009).
Jiang et al., "Reciprocal regulation of p53 and malic enzymes modulates metabolism and senescence," Nature 493(7434):689-693 (2013).
Johnson et al., "Mitigation of hematologic radiation toxicity in mice through pharmacological quiescence induced by CDK4/6 inhibition," The Journal of Clinical Investigation 120(7):2528-36 (2010).
Jones et al., "The role of CUGBP1 in age-dependent changes of liver functions," Ageing Res Rev 11(4):442-449 (2012).

(56) References Cited

OTHER PUBLICATIONS

Jung et al., "Enigma negatively regulates p53 through MDM2 and promotes tumor cell survival in mice," The Journal of Clinical Investigation, 120(12):4493-4506 (2010).
Khambata-Ford et al., "Expression of Epiregulin and Amphiregulin and K-ras Mutation Status Predict Disease Control in Metastatic Colorectal Cancer Patients Treated With Cetuximab," Journal of Clinical Oncology 25(22):3230-3237 (2007).
Knudsen et al., "Inhibition of DNA synthesis by RB: effects on G1/S transition and S-phase progression," Genes & Development 12:2278-2292 (1998).
Koff et al., "MDM2 modulates the cellular response to CDK4 inhibition," Journal of Cancer Science & Therapy, s1(01):abstract (2013).
Korotchkina et al., "The choice between p53-induced senescence and quiescence is determined in part by the mTOR pathway," Aging 2(6):344-352 (2010).
Kosar et al., "Senescence-associated heterochromatin foci are dispensable for cellular senescence, occur in a cell type- and insult-dependent manner and follow expression of p16(ink4a)," Cell Cycle 10(3):457-468 (2011).
Kubbutat et al., "Regulation of p53 stability by Mdm2," Nature 387:299-303 (1997).
Kuilman et al., "Senescence-messaging secretome: SMS-ing cellular stress," Nature Reviews Cancer 9:81-94 (2009).
Kuilman et al., "The essence of senescence," Genes & Development 24:2463-2479 (2010).
Lawless et al., "Quantitative assessment of markers for cell senescence," Exp. Gerontology 45:772-778 (2010).
Leach et al., "p53 Mutation and MDM2 Amplification in Human Soft Tissue Sarcomas," Cancer Research 53:2231-2234 (1993).
Li et al., "A Dynamic Role of HAUSP in the p53-Mdm2 pathway," Molecular Cell 13:879-886 (2004).
Li et al., "Molecular Pathways: Targeting Mdm2 and Mdm4 in Cancer Therapy," Clinical Cancer Research 19(1):34-41 (2013).
Linares et al., "Intrinsic ubiquitination activity of PCAF controls the stability of the oncoprotein Hdm2," Nature Cell Biology 9(3):331-338 (2007).
Liu, "MDM2 levels modulate the cellular senescence response to CDK4 inhibition," A dissertation Presented to the Faculty of the Graduate School of Cornell University in Partial Fulfillment of the Requirements for the Degree of Doctor of Philosophy, Mar. 1, 2013, pp. 1-152, Retrieved from the Internet: URL:http://search.proquest.com/docview/1432161078.
Loupakis et al., "KRAS codon 61, 146 and BRAF mutations predict resistance to cetuximab plus irinotecan in KRAS codon 12 and 13 wild-type metastatic colorectal cancer,"British Journal of Cancer 101:715-721 (2009).
Lujambio et al., "Non-cell-autonomous tumor suppression by p53," Cell 153(2):449-460 (2013).
Malumbres et al., "Cell cycle, CDKs and cancer: a changing paradigm," Nature Reviews Cancer 9:153-166 (2009).
Marine et al., "Mdm2-mediated ubiquitylation: p53 and beyond," Cell Death and Differentiation 17:93-102 (2010).
McCubrey et al., "Mutations and Deregulation of Ras/Raf/MEK/ERK and PI3K/PTEN/Akt/mTOR Cascades Which Alter Therapy Response," Oncotarget 3(9):954-987 (2012).
McDuff et al., "Jailbreak: Oncogene-induced senescence and its evasion," Cellular Signalling 23:6-13 (2011).
Michaud et al., "Pharmacologic inhibition of cdk4/6 arrests the growth of glioblastoma multiforme intracranial xenografts," Cancer Research 70(8):3228-3238 (2010).
Miller et al., "HdmX overexpression inhibits oncogene induced cellular senescence," Cell Cycle 9(16):3376-3382 (2010).
Moll et al., "The MDM2-p53 interaction," Mol Cancer Res 1:1001-1008 (2003).
Momand et al., "The mdm-2 Oncogene Product Forms a Complex with the p53 Protein and Inhibits p53-Mediated Transactivation," Cell 69:1237-1245 (1992).

Narita et al., "Senescence comes of age," Nature Medicine 11(9):920-922 (2005).
Narita et al., "Rb-Mediated Heterochromatin Formation and Silencing of E2F Target Genes during Cellular Senescence," Cell 113:703-716 (2003).
Oliner et al., "Oncoprotein MDM2 conceals the activation domain of tumour suppressor p53," Nature 362:857-860 (1993).
Pearson et al., "PML regulates p53 acetylation and premature senescence induced by oncogenic Ras," Nature 406:207-210 (2000).
Prieur et al., "p53 and p16(INK4A) independent induction of senescence by chromatin-dependent alteration of S-phase progression," Nature Communications 2:473, 10 pages (2011).
Puyol et al., "A Synthetic Lethal Interaction between K-Ras Oncogenes and Cdk4 Unveils a Therapeutic Strategy for Non-small Cell Lung Carcinoma," Cancer Cell 18:63-73 (2010).
Quijano et al., "Oncogene-induced senescence results in marked metabolic and bioenergetic alterations," Cell Cycle 11(7):1383-1392 (2012).
Ramsey et al., "ROS as a tumour suppressor?" Nature Cell Biology 8(11):1213-1215 (2006).
Rane et al. "Germ Line Transmission of the Cdk4(R24C) Mutation Facilitates Tumorigenesis and Escape from Cellular Senescence," Molecular and Cellular Biology 22(2):644-656 (2002).
Rayess et al., "Cellular senescence and tumor suppressor gene p16," Int J Cancer 130(8): 1715-1725 (2012).
Ringshausen et al., "Mdm2 is critically and continuously required to suppress lethal p53 activity in vivo," Cancer Cell 10:501-514 (2006).
Roberts et al., "Multiple Roles of Cyclin-Dependent Kinase 4/6 Inhibitors in Cancer Therapy," Journal of the National Cancer Institute 104(6):476-487 (2012).
Rodier et al., "Four faces of cellular senescence," The Journal of Cell Biology 192(4):547-556 (2011).
Salomoni et al., "The role of PML in Tumor Suppression," Cell 108:165-170 (2002).
Scaglioni et al., "Translation-dependent mechanisms lead to PML upregulation and mediate oncogenic K-RAS-induced cellular senescence," EMBO Mol Med 4:594-602 (2012).
Schwartz et al., "Phase I study of PD 0332991, a cyclin-dependent kinase inhibitor, administered in 3-week cycles (Schedule 2/1)," British Journal of Cancer 104:1862-1868 (2011).
Secchiero et al., "Recent Advances in the Therapeutic Perspectives of Nutlin-3," Current Pharmaceutical Design 17:569-577 (2011).
Serrano et al., "Oncogenic ras Provokes Premature Cell Senescence Associated with Accumulation of p53 and p16INK4a," Cell 88:593-602 (1997).
Singer et al., "Gene Expression Profiling of Liposarcoma Identifies Distinct Biological Types/Subtypes and Potential Therapeutic Targets in Well-Differentiated and Dedifferentiated Liposarcoma," Cancer Research 67(14):6626-6636 (2007).
Sperka et al., "DNA damage checkpoints in stem cells, ageing and cancer," Nature Reviews Molecular Cell Biology 13:579-590 (2012).
Stark et al., "The BioGRID Interaction Database: 2011 update," Nucleic Acids Research 39:D698-D704 (2011).
Steelman et al., "Roles of the Raf/MEK/ERK and PI3K/PTEN/Akt/mTOR pathways in controlling growth and sensitivity to therapy-implications for cancer and aging," Aging 3(3):192-222 (2011).
Supplemental European Search Report dated Nov. 29, 2016 in Application No. EP 14785765.
Talluri et al., "Regulation of transcription and chromatin structure by pRB: Here, there and everywhere," Cell Cycle 11(17):3189-3198 (2012).
Taylor et al., "Functional Copy-Number Alterations in Cancer," PloS ONE 3(9):e3179 (2008).
Tchkonia et al., "Cellular senescence and the senescent secretory phenotype: therapeutic opportunities," The Journal of Clinical Investigation 123(3):966-972 (2013).
Teicher, "Searching for molecular targets in sarcoma," Biochemical Pharmacology 84:1-10 (2012).

(56) References Cited

OTHER PUBLICATIONS

Thangavel et al., Therapeutically activating RB: reestablishing cell cycle control in endocrine therapy-resistant breast cancer, Endocr Relat Cancer 18(3):333-345 (2011).

Van Cutsem et al., "Cetuximab and Chemotherapy as Initial Treatment for Metastatic Colorectal Cancer," The New England Journal of Medicine 360:1408-1417 (2009).

Varmeh et al., "Cellular Senescence as a Possible Mechanism for Halting Progression of Keloid Lesions," Genes & Cancer 2(11):1061-1066 (2011).

Wawrzynow et al., "MDM2 Chaperones the p53 Tumor Suppressor," The Journal of Biological Chemistry 282(45):32603-32612 (2007).

Wiedemeyer et al., "Pattern of retinoblastoma pathway inactivation dictates response to CDK4/6 inhibition in GBM," PNAS 107(25):11501-11506 (2010).

Wolyniec et al., "E6AP ubiquitin ligase regulates PML-induced senescence in Myc-driven lymphomagenesis," Blood 120(4):822-832 (2012).

Xiao et al., "Interaction between the retinoblastoma protein and the oncoprotein MDM2," Nature 375:694-698 (1995).

Yap et al., "mdm2: a bridge over the two tumour suppressors, p53 and Rb," Oncogene 18:7681-7689 (1999).

Zezula et al., "p21cip1 is required for the differentiation of oligodendrocytes independently of cell cycle withdrawal," EMBO *reports* 2(1):27-34 (2001).

Zou et al., "Cdk4 disruption renders primary mouse cells resistant to oncogenic transformation, leading to Arf/p53-independent senescence," Genes & Development 16: 2923-2934 (2002).

Kovatcheva, Marta. MDM2 is a mediator of senescence associated with CDK4 inhibition. Molecular Genetics of Aging (CSHL), Oct. 9, 2012.

Kovatcheva et al., MDM2 is a mediator of senescence associated with CDK4 inhibition. EMBO Poster Presentation, Sep. 22, 2012.

FIGURE 1A-C
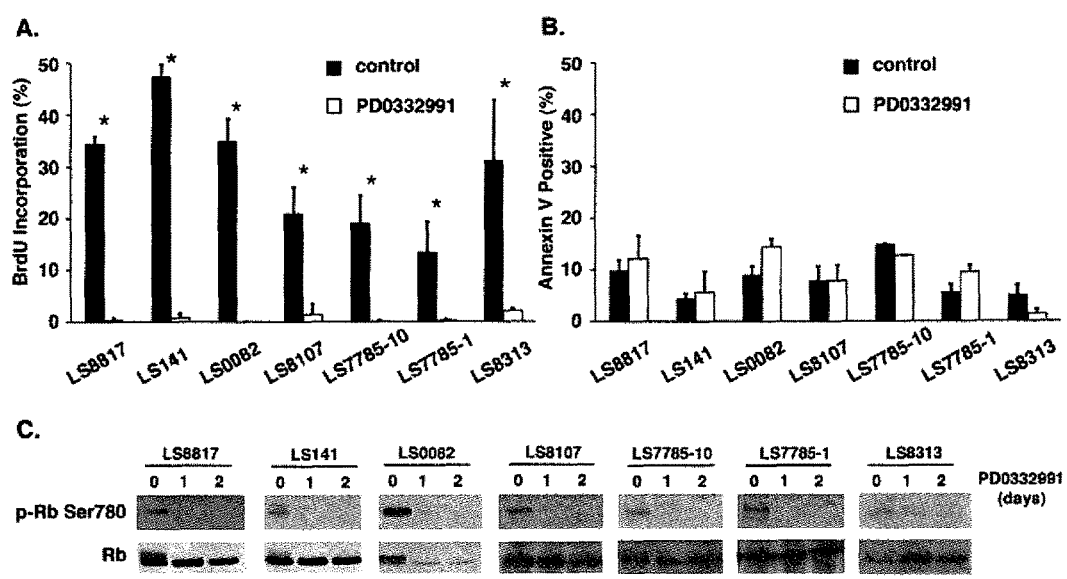

FIGURE 2A-D
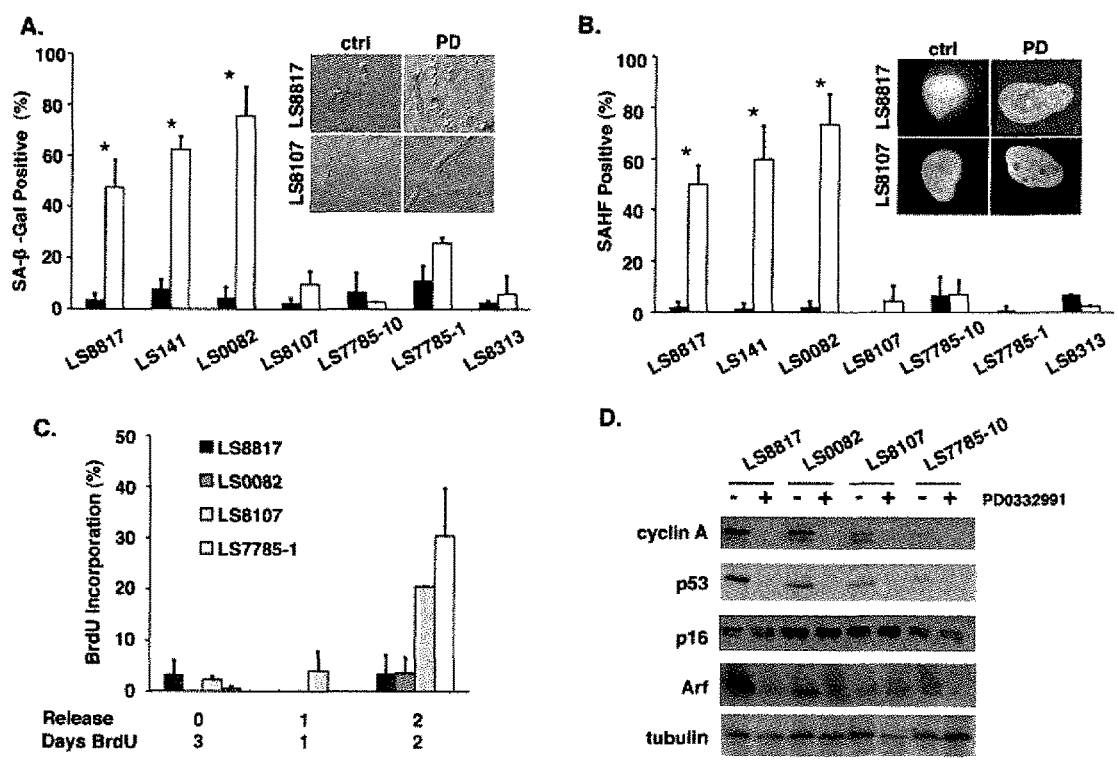

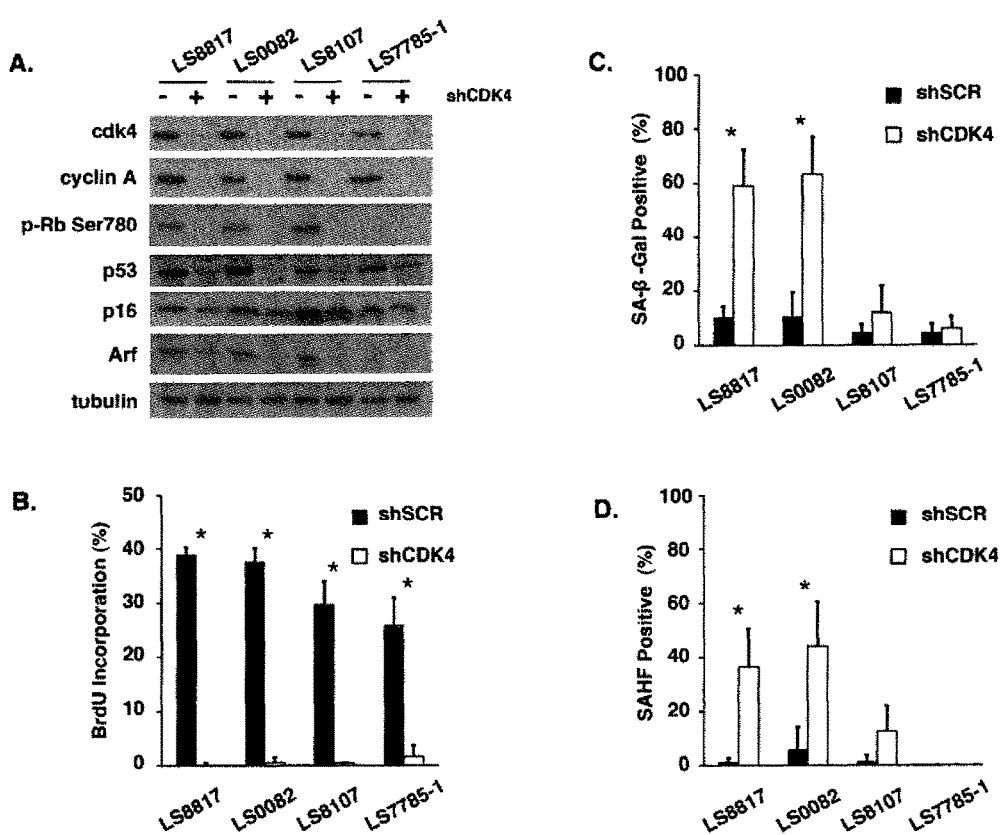
FIGURE 3A-D

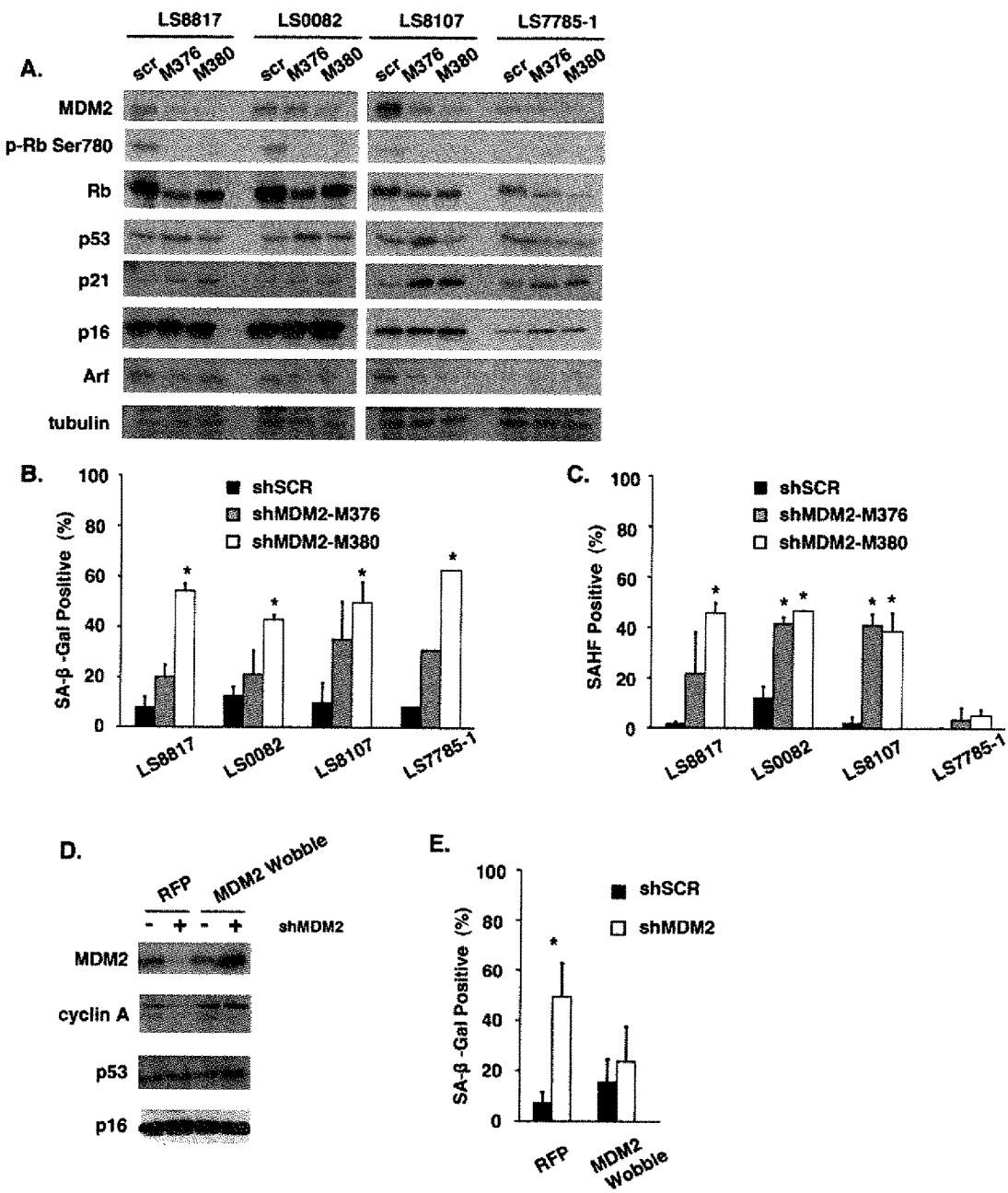
FIGURE 4A-E

FIGURE 5A-D
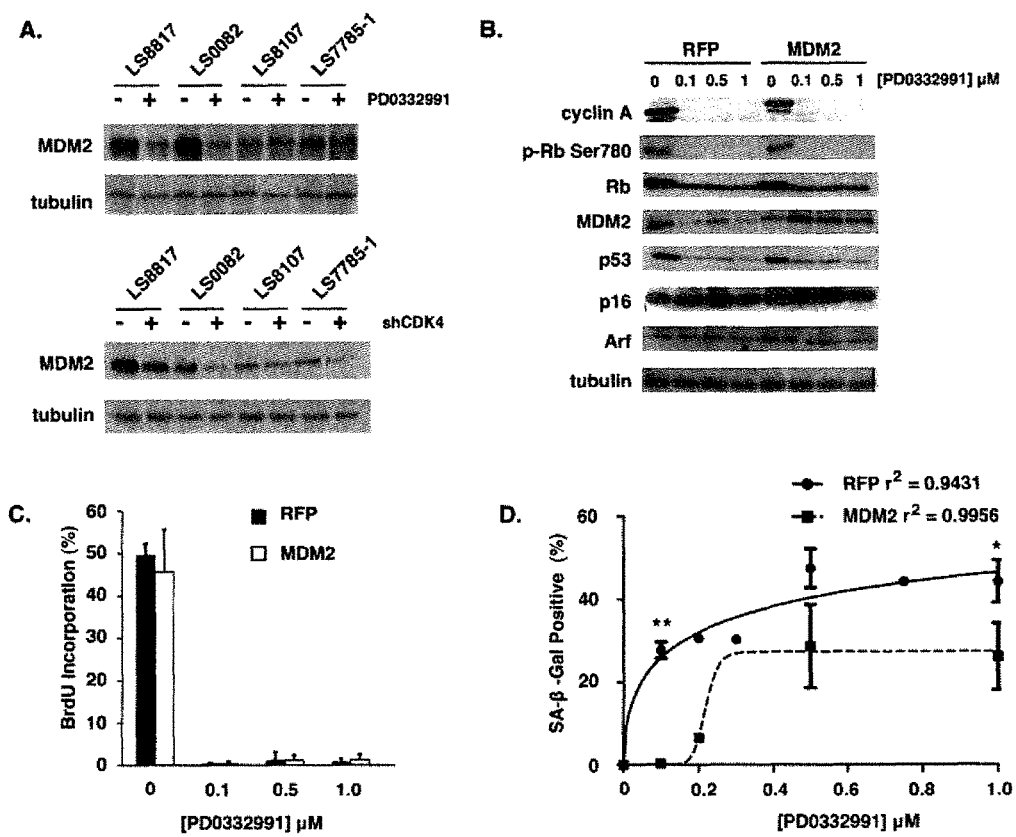

FIGURE 6A
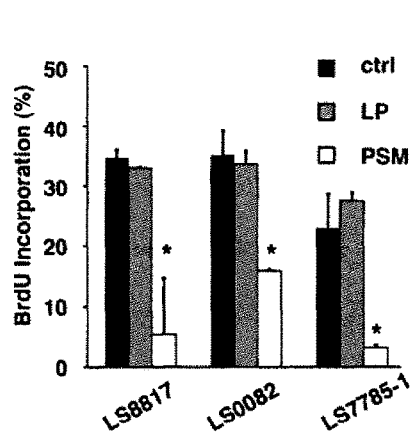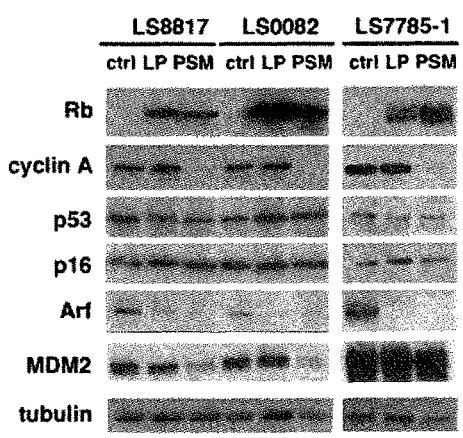

FIGURE 18A-B
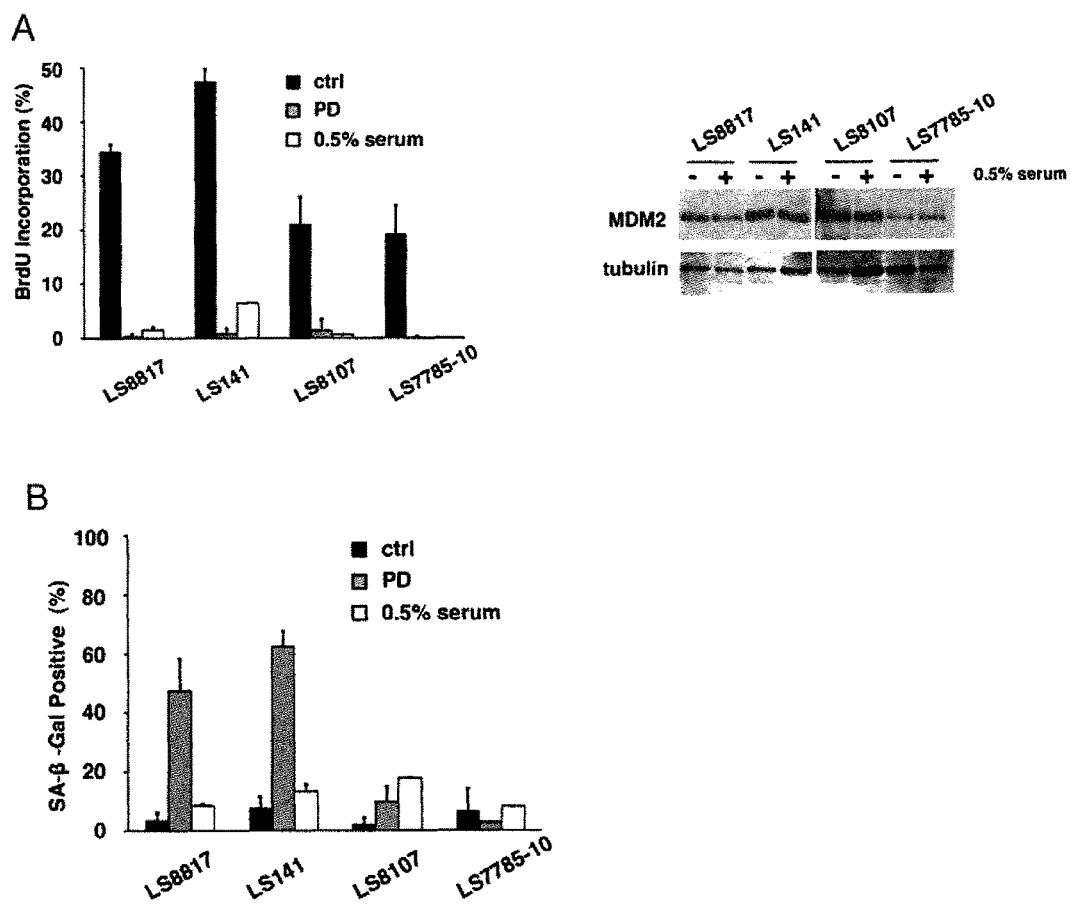

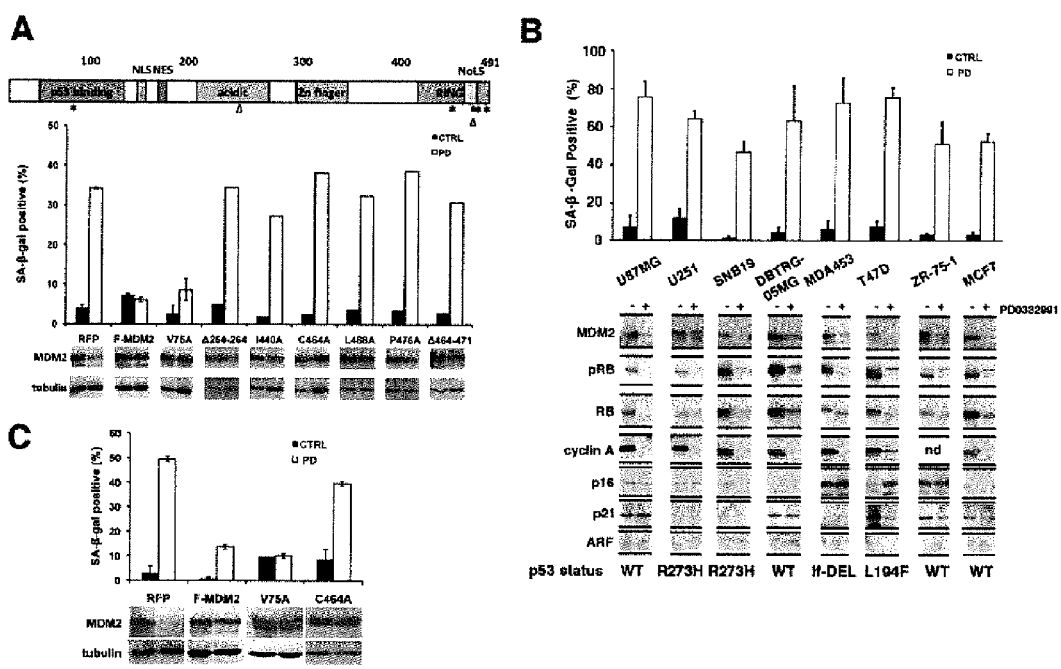
FIGURE 19A-C

FIGURE 23A-B

FIGURE 26A-B
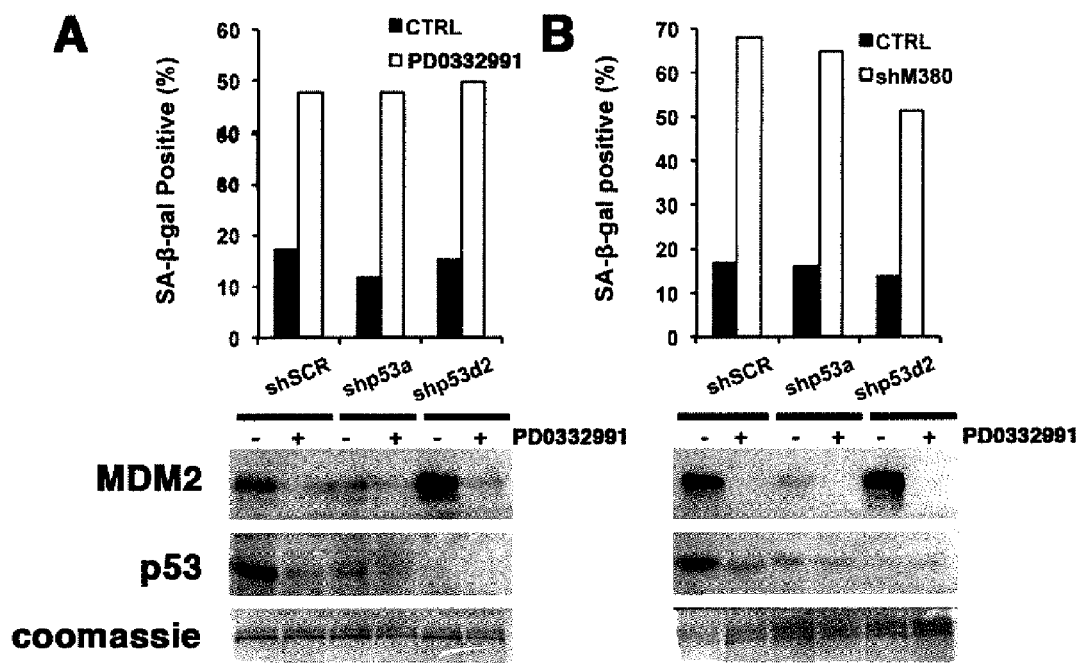

COMPANION DIAGNOSTIC FOR CDK4 INHIBITORS

CROSS-REFERENCE TO RELATED APPLICATIONS

This application is a continuation of International Patent Application No. PCT/US2014/034399, filed Apr. 16, 2014, and claims priority to U.S. Provisional Application Ser. No. 61/812,412, filed Apr. 16, 2013, and U.S. Provisional Application Ser. No. 61/893,755, filed Oct. 21, 2013, to each of which priority is claimed and the contents of each which are incorporated herein in their entireties.

GRANT INFORMATION

This invention was made with government support under grant numbers CA047179, CA140146 and CA089563 awarded by the National Institutes of Health. The government has certain rights in the invention.

SEQUENCE LISTING

The specification further incorporates by reference the Sequence Listing submitted herewith via EFS on Oct. 16, 2015. Pursuant to 37 C.F.R. §1.52(e)(5), the Sequence Listing text file, identified as 0727340331SEQLIST.txt, is 14,187 bytes and was created on Oct. 13, 2015. The Sequence Listing, electronically filed herewith, does not extend beyond the scope of the specification and thus does not contain new matter.

1. INTRODUCTION

This present invention relates to biomarkers which may be used to evaluate the likelihood that a CDK4 inhibitor would produce an anti-cancer effect in a subject. As such, these biomarkers may be used in methods of treating cancer patients.

2. BACKGROUND OF THE INVENTION

Mouse double minute 2 homolog (MDM2) is a protein that is encoded by the MDM2 gene. MDM2 functions as an E3 ubiquitin ligase and as a negative regulator of the tumor suppressor protein, p53, by ubiquitinating and targeting p53 for degradation (8). MDM2 affects the cell cycle, apoptosis and tumorigenesis through interaction with other proteins, including retinoblastoma (RB) (50).

Genome-wide association studies, such as The Cancer Genome Atlas projects, show that most cancers are genetically heterogeneous. A few recurrent alterations/mutations are integral to the development and progression of a tumor, while a host of other changes can substantially alter its phenotype, affecting progression and impacting both patient prognosis and the efficacy of therapy (1-5). Ninety percent of well-differentiated and dedifferentiated liposarcomas (WD/DDLS) have amplification of genes on chromosome segment 12q13-15, in a background of karyotypes that are widely variable and, in many instances, highly complex. The 12q13-15 amplification is associated with overexpression of the oncogenes, MDM2 and CDK4, and the corresponding translated proteins are thought to promote liposarcomagenesis (6).

CDK4 promotes cell proliferation by catalyzing phosphorylation and inactivation of RB (7), and MDM2 suppresses oncogene-induced apoptosis or senescence by inactivating p53 (8). Drugs have been developed that specifically target these potential drivers and the effect of these targeted agents in patients with a variety of tumors has been an active area of investigation. However predicting the efficacy of these drugs on patient outcome has been problematic, because of the extensive molecular crosstalk between p53 and RB pathways and the genomic heterogeneity of the tumors examined (9, 10).

3. SUMMARY OF THE INVENTION

The present invention relates to methods and compositions which provide a companion diagnostic for CDK4 inhibitors, and in particular, to the use of MDM2 expression as a biomarker for the likelihood that a cancer can be successfully treated by CDK4 inhibition. It is based, at least in part, on the discovery that treatment with a CDK4 inhibitor is more effective where treated cancer cells undergo cellular senescence rather than a transient cell cycle arrest, where cellular senescence is associated with a decreased MDM2 protein level.

4. BRIEF DESCRIPTION OF THE FIGURES

FIG. 1A-C. PD0332991 induces growth arrest. Cells grown in the presence (white) or absence (black) of PD0332991 for 48 hours and labeled with BrdU, a marker of ongoing DNA replication (A), or annexin V and 7-AAD, a marker of apoptosis (B). Mean percentage of BrdU incorporation or annexin V+/7-AAD− cells was calculated from three or more independent experiments. Error bars represent standard deviation ($*p<0.05$). (C) The amount of serine 780 phosphorylated or total Rb was detected by immunoblot in extracts from asynchronously growing cells (0) and cells treated with PD0332991 for either 1 or 2 days (representative experiment; n>3 for each cell line).

FIG. 2A-D. PD0332991 induces senescence in some cells. Cells were grown in the presence (white) or absence (black) of PD0332991 for 7 days. Mean percentage standard deviation). ($*p<0.05$). (A) Senescence-associated β-galactosidase and (B) HP1γ staining for senescence associated heterochromatic foci (SAHF) formation was quantitated for three or more independent experiments for each cell line. ($*p<0.05$). Representative phase contrast micrographs of cells stained for SA-β-gal or immunofluorescence staining for HP1γ in two of the cell lines before (ctrl) and after (PD) drug treatment are shown in the insets of FIGS. 2A and 2B, respectively. (C) BrdU incorporation. Cell lines were treated with PD0332991 for seven days, and released into drug-free medium containing BrdU for the number of days indicated. Error bars represent the standard deviation of the mean calculated from three independent trials. (D) The amount of cyclin A, p53, p16 and Arf were detected by immunoblotting extracts prepared from asynchronously growing cells (−) and cells treated with PD0332991 (+) for 7 days (n>3).

FIG. 3A-D. CDK4 knockdown mimics the effect of PD0332991. Following lentiviral infection, CDK4 knockdown cells (shCDK4) and cells infected with a scramble control shRNA (shSCR) were selected for ten days in puromycin. (A) Immunoblot. Extracts from cells expressing shRNA directed against CDK4 (+) and scramble control (−) were resolved by SDS-PAGE and the level of the indicated proteins was measured by immunoblot. (B) BrdU incorporation. Cells infected with vectors expressing scrambled (black) or CDK4 shRNAs (white) were labeled with BrdU for 2 hours. Mean percentage of BrdU incorporation was calculated from three or more independent trials. Error bars represent standard deviation. (*p<0.05). (C) Senescence-associated β-galactosidase and (D) HP1γ staining for senescence associated heterochromatic foci (SAHF) formation was calculated for cells infected with scrambled (black) and CDK4 shRNAs (white). The mean and standard deviation from three independent experiments were determined. (*p<0.05)

FIG. 4A-E. MDM2 knockdown induces senescence in all of the liposarcoma cell lines. The cells indicated were transduced with two different MDM2 knockdown lentiviral vectors (M376 or M380) or a scrambled non-specific vector (scr) and selected in puromycin for 10 days prior to extraction of proteins for immunoblotting (A), or analysis of senescence-associated beta-galactosidase staining (B), or HP1γ staining (C). (D and E) LS8817 cells were transduced with a lentivirus expressing a wobbled allele of MDM2 and selected before secondary transduction with the lentivirus expressing M380 and selection in puromycin for ten days prior to immunoblot (D) and senescence associated beta-galactosidase staining (*p<0.05) (E). These experiments were done at least three times with different pools of transductants with similar results each time.

FIG. 5A-D. Enforced MDM2 expression can abrogate the senescence promoting activity of PD0332991 but not its ability to induce growth arrest. (A) Immunoblot. The amount of MDM2 was measured in extracts prepared from cells treated with PD0332991 for two days or selected for shCDK4 expression as shown in FIG. 3A. Tubulin was a loading control. (B) Immunoblot. Cells were transduced with lentiviral vectors expressing either RFP or MDM2 and the amount of proteins determined 48 hours after treatment with the indicated dose of PD0332991. (C) BrdU incorporation was measured in the RFP and MDM2 expressing cells forty-eight hours after treatment with the indicated dose of PD0332991. (D) Senescence associated beta-galactosidase staining was carried out in the RFP or MDM2 expressing cells treated with different doses of PD0332991 for seven days. This experiment was carried out with three different pools of transductants multiple times (*p<0.05, **p<0.01). $r^2$ is calculated as the best-fit correlation.

FIG. 6A-B. PSM-Rb can induce senescence. The responder cells, LS8817 and LS0082, and the non-responder cells, LS7785-1, were transduced with a lentivirus expressing either the large pocket of RB (LP) or a non-phosphorylatable large pocket of RB (PSM) and selected for 10 days in puromycin. The effect of these gene products on BrdU incorporation and protein expression (A) and senescence associated beta-galactosidase staining (B) were assessed as described in the legends to the other figures. (B) Endogenous phosphorylated Rb was measured as a marker of CDK4/6 kinase activity in cells that are expressing the LP or PSM pocket domains. PD0332991 and untreated control cells are shown for a comparison. This experiment was done at least three times with different pools of transductants with similar results each time.

Figure 7:
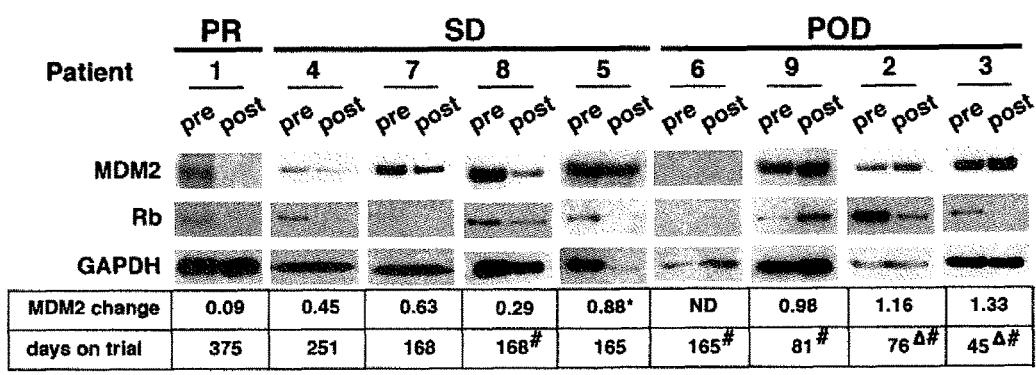

FIG. 7. Changes in MDM2 correlate with the response of patients with WD/DDLS to PD0332991. Nine patients accrued between January 2012 and August 2012 were enrolled in a continuing phase II clinical trial of PD0332991. Pre-treatment biopsies and post-treatment biopsies were collected from these patients and the expression of MDM2 and RB were measured by immunoblot. GAPDH serves as a loading control. Patients, indicated by numbers 1 through 9, fell into three classes (PR, partial response; SD, stable disease; POD, progression of disease) based on their best response to the drug as measured by target lesion growth by CT scan according to RECIST criteria. The change in MDM2 expression was measured and normalized to the change in GAPDH in each pair of samples. For patient 5, the change in MDM2 is highlighted with an asterisk because the value was obtained by normalizing MDM2 to actin (not shown). Superscripted number sign indicates that the patient withdrew from the trial, and triangles indicate that the patient is deceased. The number of days that the patient has been on the trial is indicated.

Figure 8:
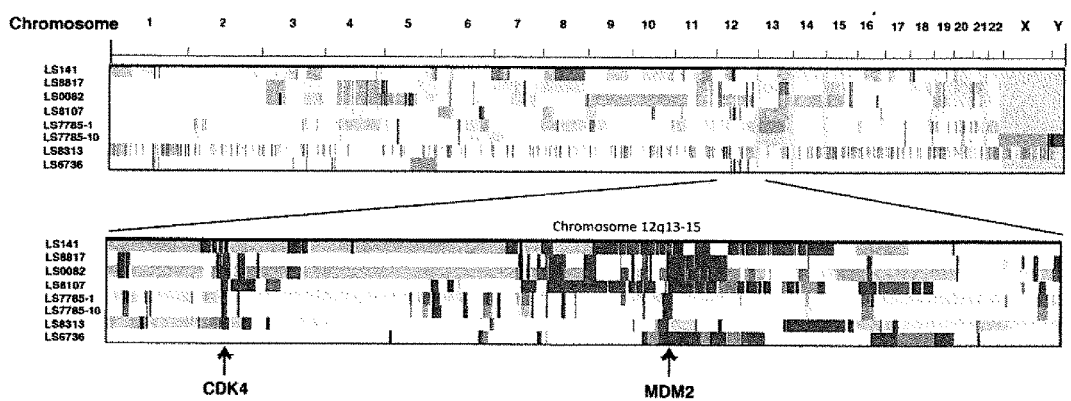

FIG. 8. Copy number alterations in WD/DDLS cell lines as determined by comparative genomic hybridization. Amplification (red) and deletions (blue) were identified using the RAE algorithm and are visualized using Integrated Genomic Viewer (http://broadinstitute.org/igv).

Figure 9:
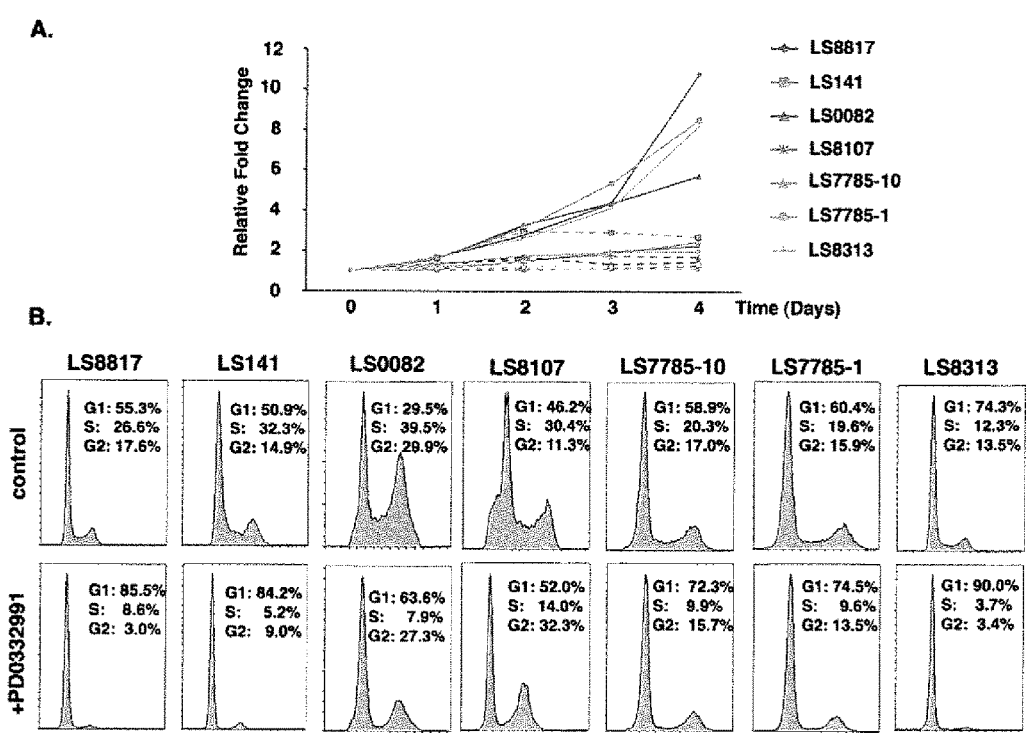

FIG. 9A-B. PD0332991 induces G1 arrest in liposarcoma cell lines. (A) Number of cells isolated from cultures grown in the presence (dashed lines) or absence (solid lines) of PD0332991 for 4 days quantitated daily by Coulter Counter and graphed as a function of time. (B) Cells grown in the presence of PD0332991 for two days or asynchronously growing in the absence of the drug (control) were stained with propidium iodine and analyzed by flow cytometry to determine cell cycle distribution within culture. Percentages annotated on graphs represent the mean of three or more independent experiments.

Figure 10:
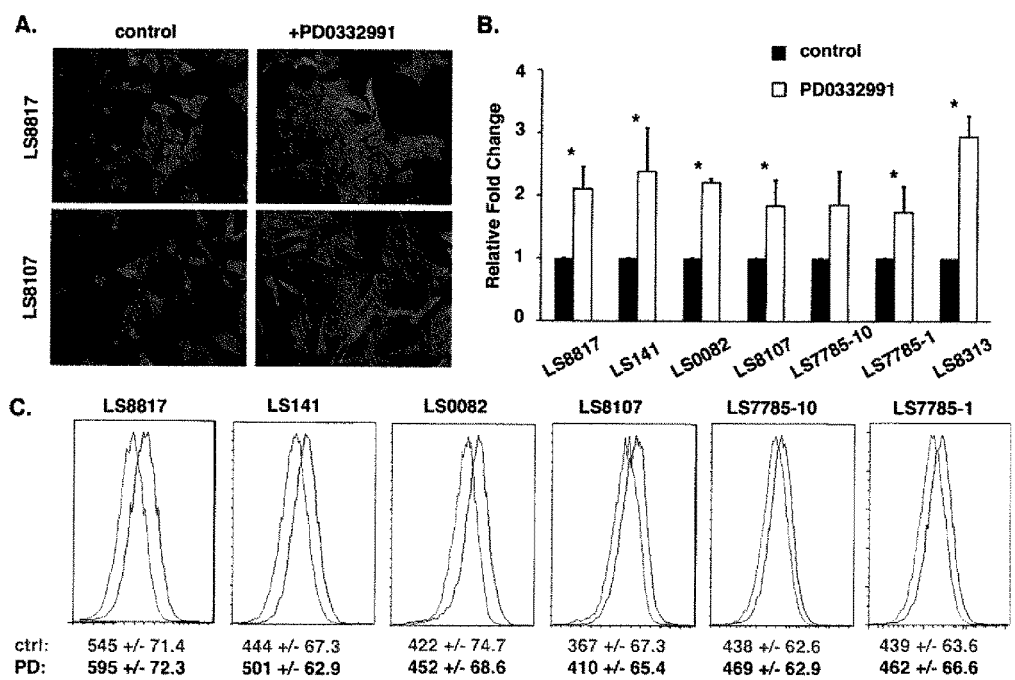

FIGS. 10A-C. PD0332991 induces a change in cell volume. Cells grown in the presence or absence of PD0332991 for 48 hours were stained with phalloidin or analyzed by flow cytometry. (A) Representative images obtained by fluorescence microscopy of two of the cell lines stained with phalloidin (red) and DAPI (blue). (B) Mean cell size in control untreated cells (black) and PD0332991 treated cells (white) were averaged over three independent trials (±standard deviation). (*p<0.05) (C) Forward scatter plots obtained by flow cytometry. The distribution of untreated control cells (red) and PD0332991 treated cells (blue) is indicated. The peak mean value over three independent experiments are quantified below (mean cell size+standard deviation).

Figure 11:
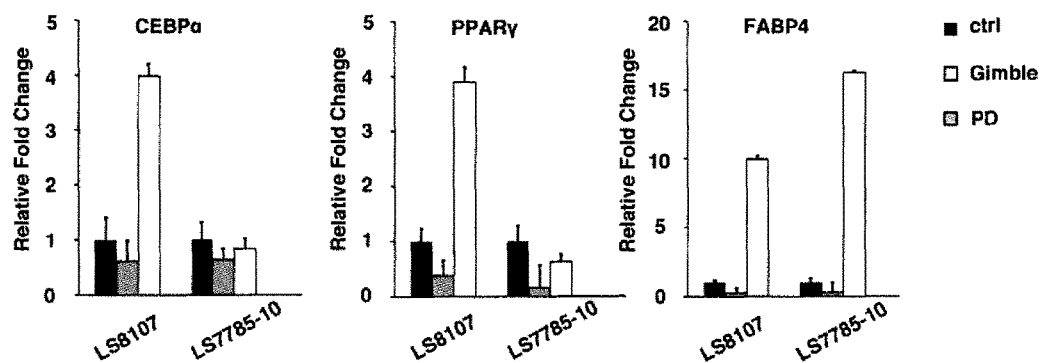

FIG. 11. PD0332991 does not induce differentiation. The cell lines were treated with either PD0332991 (grey) or differentiation medium (Gimble, white) for seven days and the amount of RNA for each indicated gene product compared to that seen in untreated well growing cells (ctrl, black).

FIG. 12A-D. Expression of CDK4 or CDK6 was inhibited with shRNA compared to scramble controls (scr). All infected cells were selected for ten days in puromycin. (A) Immunoblot. Extracts were prepared from the infected, puromycin-resistant cells and expression of CDK4 and CDK6 measured by SDS-PAGE and immunoblot. (B) Cells infected with vectors expressing scrambled (black), CDK4 shRNA (gray), or CDK6 shRNA (white) were labeled with BrdU for 2 hours. Mean percentage of BrdU incorporation was calculated from three or more independent trials. Error bars represent standard deviation. (*p<0.05). (C) Senescence-associated β-galactosidase and (D) HP1γ staining for senescence associated heterochromatic foci (SAHF) formation was calculated for cells infected with scrambled (black), CDK4 shRNA (gray), and CDK6 shRNA (white). (*p<0.05). These experiments were done at least three times with different pools of transductants with similar results each time.

Figure 13:
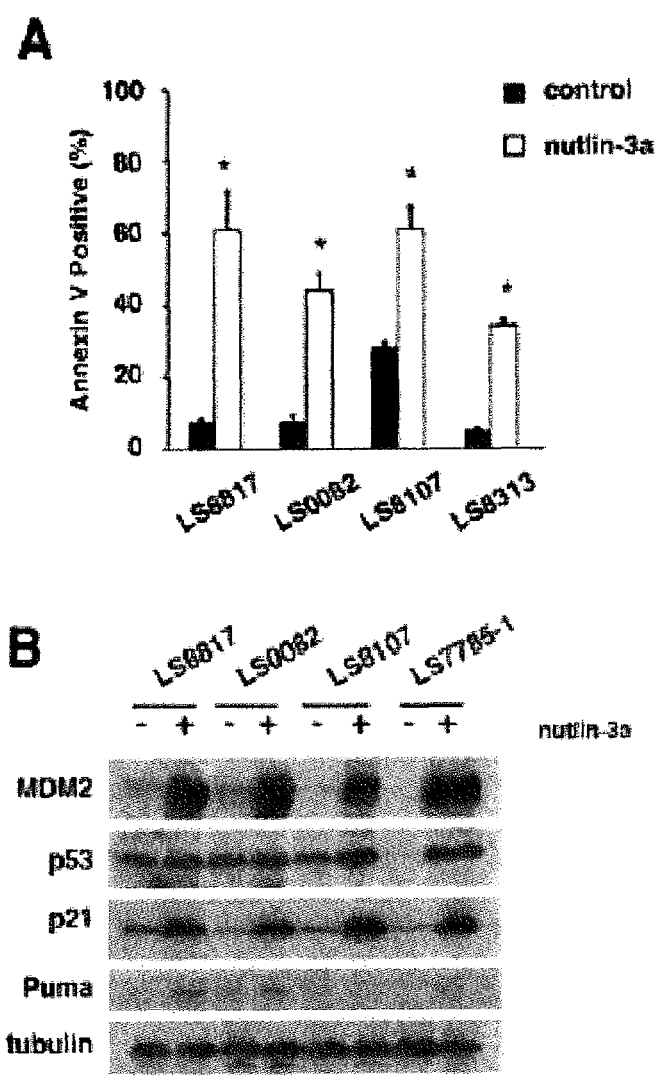

FIG. 13A-B. Nutlin-3a induces apoptosis in all the liposarcoma cell lines. The indicated cell lines were treated with nutlin-3a or vehicle control and extracts were prepared for immunoblotting (A) or annexin V staining (B) forty-eight hours after treatment. Mean percentage of annexin V+/7-

AAD− cells was calculated from three or more independent experiments. Error bars represent standard deviation (*p<0.05).

Figure 14:
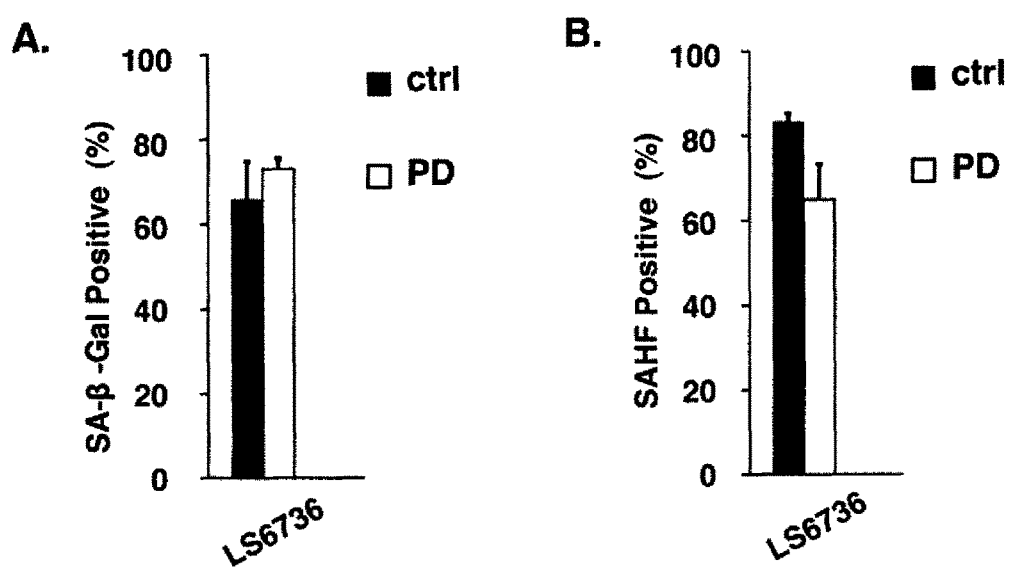

FIG. 14A-B. MDM2 expression and senescence are correlated to amplification of CDK4. (A) Senescence associated β-galactosidase and (B) HP1γ staining were examined in LS6736 cells characterized by MDM2 amplification but not CDK4 co-amplification after treatment with PD0332991 (white) or control media (black) for seven days.

FIG. 15A-D. PD0332991 induced senescence correlates with changes in MDM2 expression. Cells were grown in the presence (white) or absence (black) of PD0332991 for 7 days. Mean percentage (±standard deviation). (*p<0.05). (A) The amount of MDM2, p53, cyclin A, p16, p21, and tubulin were detected by immunoblotting extracts prepared from cells treated with PD0332991 (7D PD) or asynchronously growing non-treated (ctrl) for 7 days. (B) Representative phase contrast micrographs of cells stained for SA-β-gal in cell lines treated with control media (ctrl) or PD0332991 (7D PD) drug treatment. (C) BrdU incorporation and (D) Senescence-associated β-galactosidase was calculated for cells after treatment with PD0332991 (7D PD) or control media (ctrl).

Figure 16:
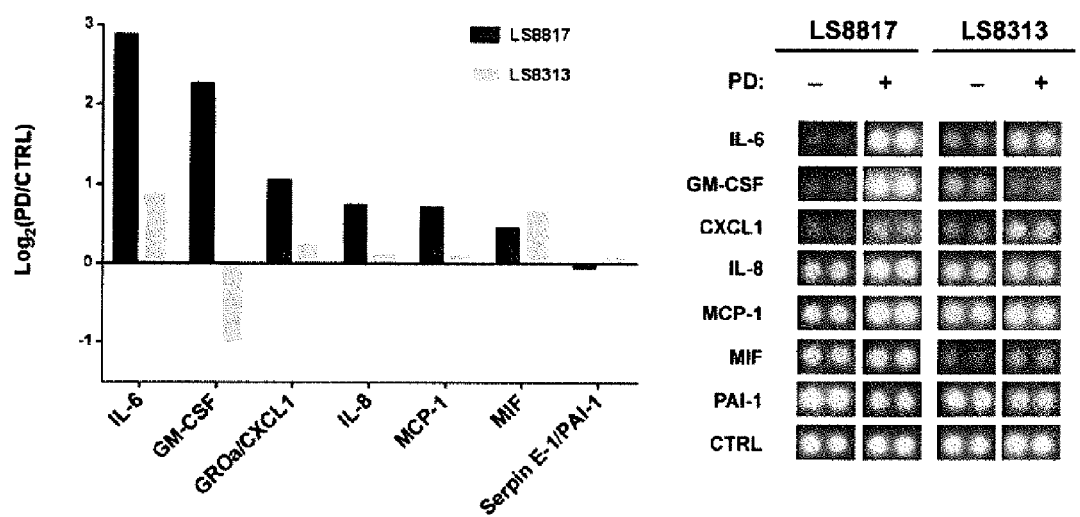

FIG. 16. Responder LS8817 (black) and the non-responder LS8313 (light gray) were cultured in the presence or absence of PD0332991 for seven days and the effect of the drug on cytokine expression plotted on the left. Representative autoradiographs are shown on the right.

Figure 17:
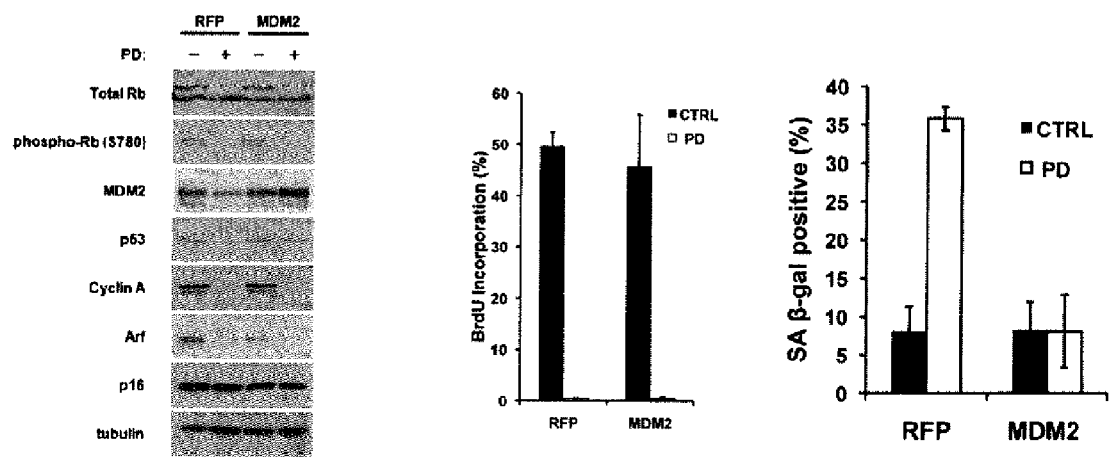

FIG. 17. The enforced expression of MDM2 in LS8817 can prevent PD0332991 induced loss of the protein (left) and accumulation of senescence-associated β-galactosidase positive cells (right) but not the drug induced reduction of BrdU incorporation (middle). Cells transduced with an RFP expressing virus were used as a control.

FIGS. 18A-E. Turnover of MDM2 is regulated post-translationally and associated with unbalanced signaling. (A) The responder cells LS8817 LS0082 and the non-responder LS7785-1 were transduced with a lentivirus expressing either the large pocket of RB (LP) or a non-phosphorylatable large pocket of RB (PSM) and selected for five days in blasticidin. The effect of these gene products on BrdU incorporation is shown on the left, senescence associated beta-galactosidase staining on the right, and expression of MDM2, phosphorylated RB, p53, p16, Arf and cyclin A expression in the center. This experiment was done at least three times with different pools of transductants with similar results each time. (B) Serum starvation induces growth arrest but no change in MDM2 or senescence. The indicated cells were grown in 0.5% serum (white) or treated with PD0332991 (gray) and proliferation measured by incorporation of BrdU (left) and the number of cells undergoing senescence by staining for senescence associated β-galactosidase (right). The level of MDM2 was measured by immunoblot (center). Tubulin was a loading control. (C) Cells were treated with PD0332991 for two days and the effect on MDM2 transcript levels determined by qPCR. This experiment was repeated at least three times on different biologic replicates. (D) The indicated cell lines were treated with PD0332991 for two days and cycloheximide added and samples collected every 15 minutes from 30-60 minutes to measure the amount of MDM2 by immunoblot. Tubulin is a loading control. Data compiled from at least three independent experiments is plotted (mean and standard deviation) and a representative immunoblot is shown. (E) Serum starvation has a more modest effect on MDM2 half-life than CDK4 inhibition. The cells were treated with PD0332991 or 0.5% serum and the effect on MDM2 levels determined by immunoblot. The graphs are compiled from the data obtained in three independent biologic replicates and representative autoradiographs are shown.

FIG. 19A-C. Senescence associated with the downregulation of MDM2 is p53 and INK4 independent. (A) The ability of MDM2 to block senescence induced by PD0332991 is dependent on an intact RING domain but not the ability to bind p53. Cells were transduced with lentiviral vectors encoding the indicated mutants of MDM2 and after selection were treated with PD0332991 and the expression of MDM2 determined by immunoblot and the percentage of cells that undergo senescence by measuring senescence associated β-galactosidase. This experiment was repeated three times with similar results in both LS8817 and LS141. (B) Glioma (U87MG, U251, SNB19, DBTRG-05MG) and breast cancer (MDA453, T47D, ZR-75-1, and MCF7) cells were treated with PD0332991 and its effects on senescence and protein expression examined as described. The p53 mutational status of these cell lines (WT, wild type; R273H and L194F, missense mutations; if-DEL, in-frame deletion of 30 nucleotides at amino acid 368) were obtained from the p53 mutation database and the RIKEN bioresource databank and is consistent with the detection of p21 by immunoblot. (C) SNB19 cells, a p53 mutant and INK4A deficient cell, was transduced with the mutants described in panel A and their effect on senescence determined.

Figure 20:
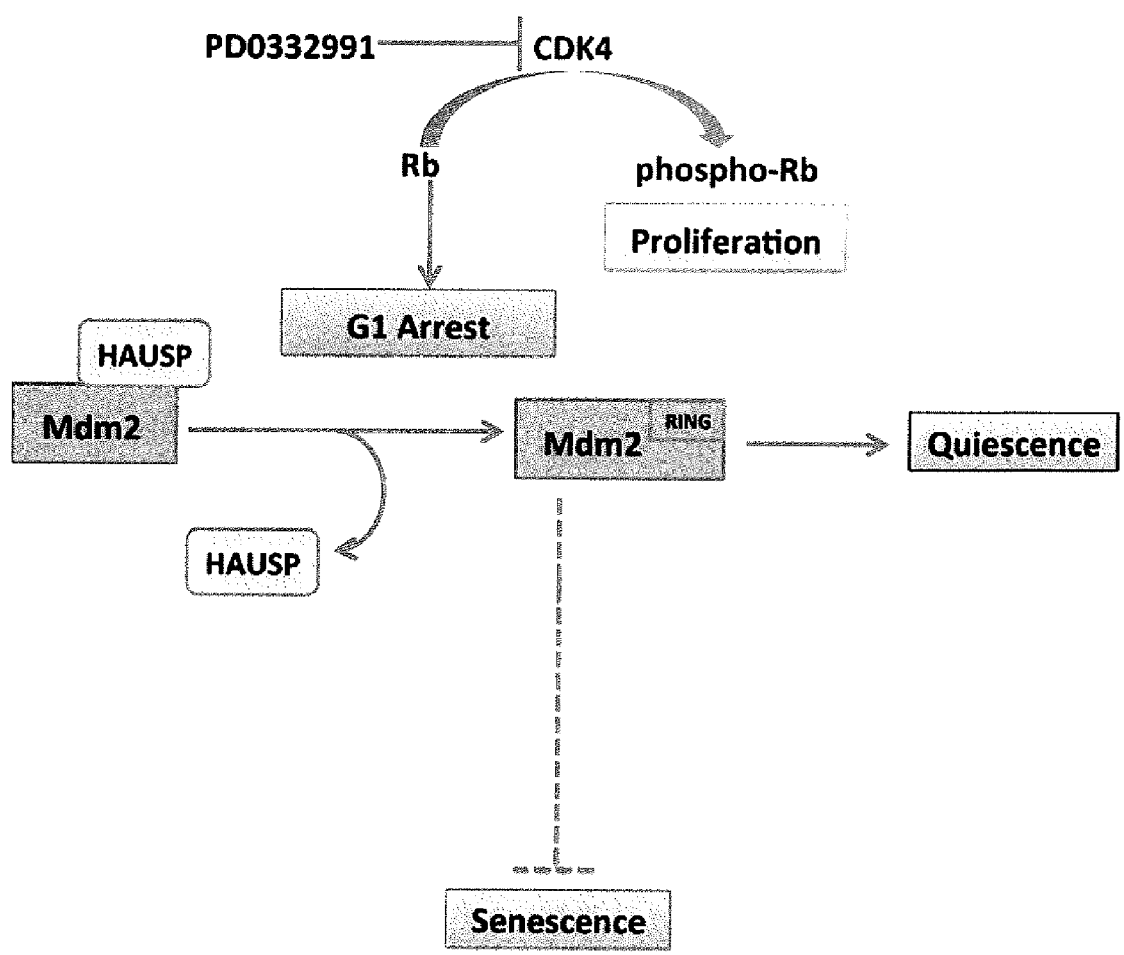

FIG. 20. Summary model. This model summarizes the key points suggesting that it is the unbalanced signaling associated with growth arrest induced by accumulation of unphosphorylated RB that triggers the post-translational change in MDM2 that activates a p53- and INK4A-independent senescence program. In non-responders, the cell either does not undergo unbalanced arrest or cannot activate the MDM2 turnover pathway that triggers the p53- and INK4A-independent senescence pathway. Inhibition of CDK4 further results in the dissociation of the MDM2 and HAUSP complex in non-responder and responder cells.

Figure 21A:
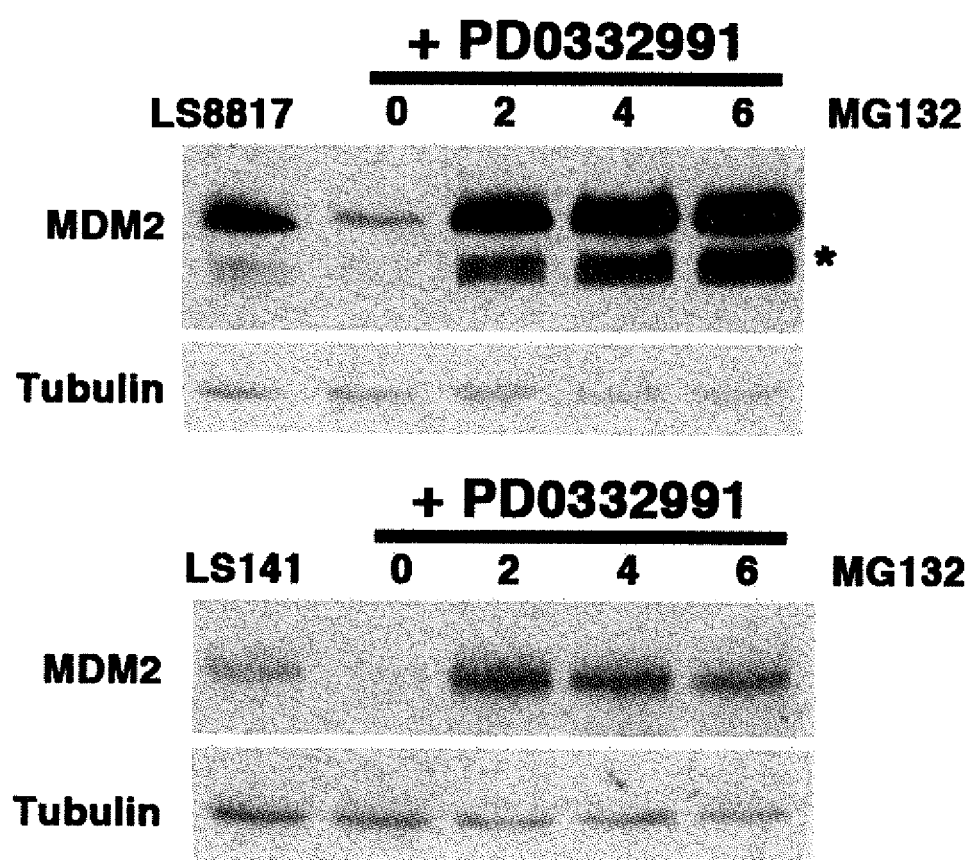
Figure 21B:
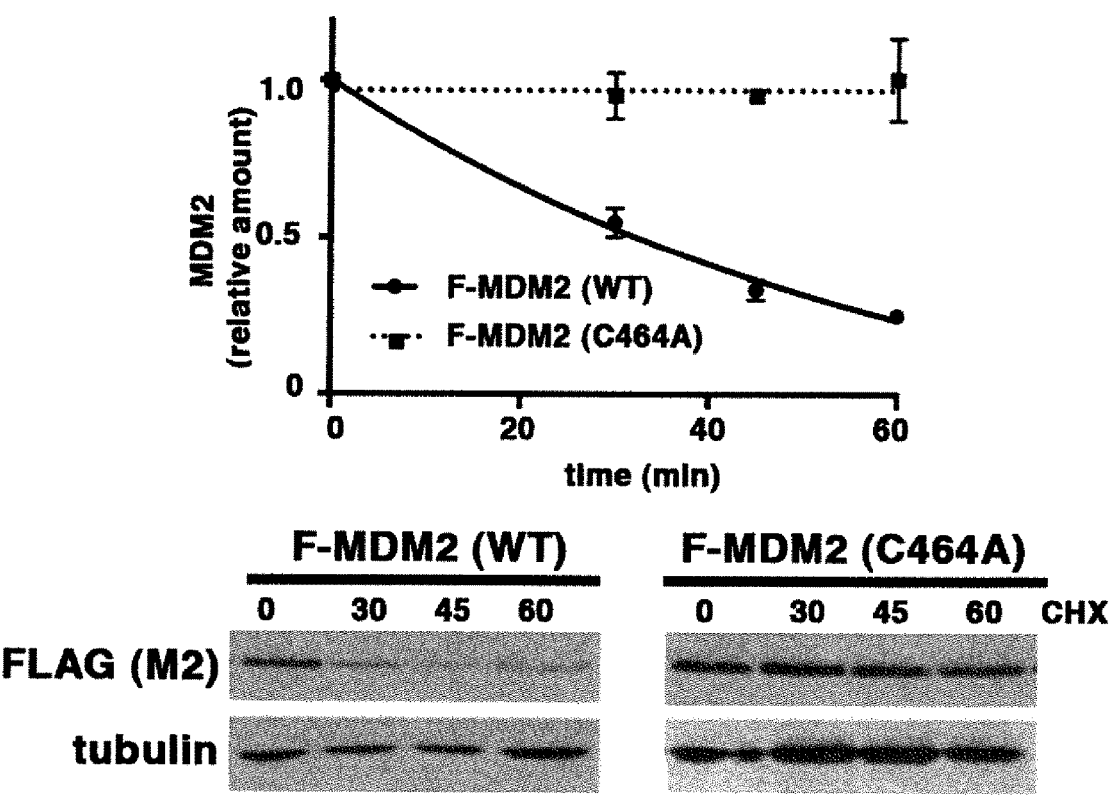

FIG. 21A-B. Turnover of MDM2 is regulated post-translationally. (A) Cell lines were treated with PD0332991 for two days after which 10 μM of the proteasome inhibitor MG132 was added for the indicated times (hours). Tubulin was used as a loading control. This experiment was repeated twice with similar results. (B) LS8817 cells transduced with either a FLAG-tagged MDM2 or a FLAG-tagged C464A mutant of MDM2 were selected and the turnover of the FLAG-tagged protein measured by immunoblot after protein synthesis was blocked with cycloheximide for the indicated amount of time. A representative immunoblot is shown and the mean and standard deviation was compiled from two independent experiments.

Figure 22:
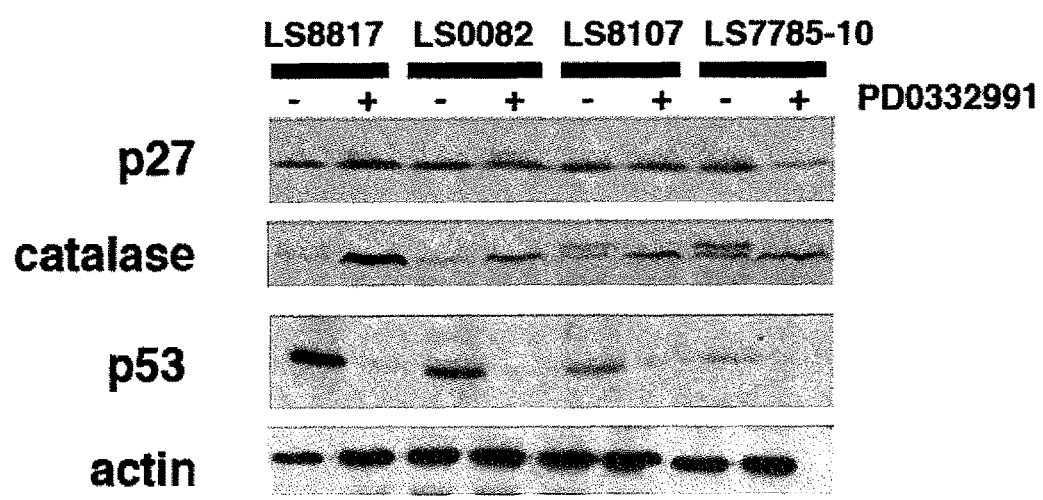

FIG. 22. Additional immunoblot analysis in responder and non-responder cells. As described in the legend to FIG. 5A, immunoblots were used to measure the accumulation of p27, catalase and p53 in cells treated with PD0332991 and proteins extracted in SDS RIPA. Actin is a loading control. This experiment was repeated at least three times for each cell line.

Figure 23:
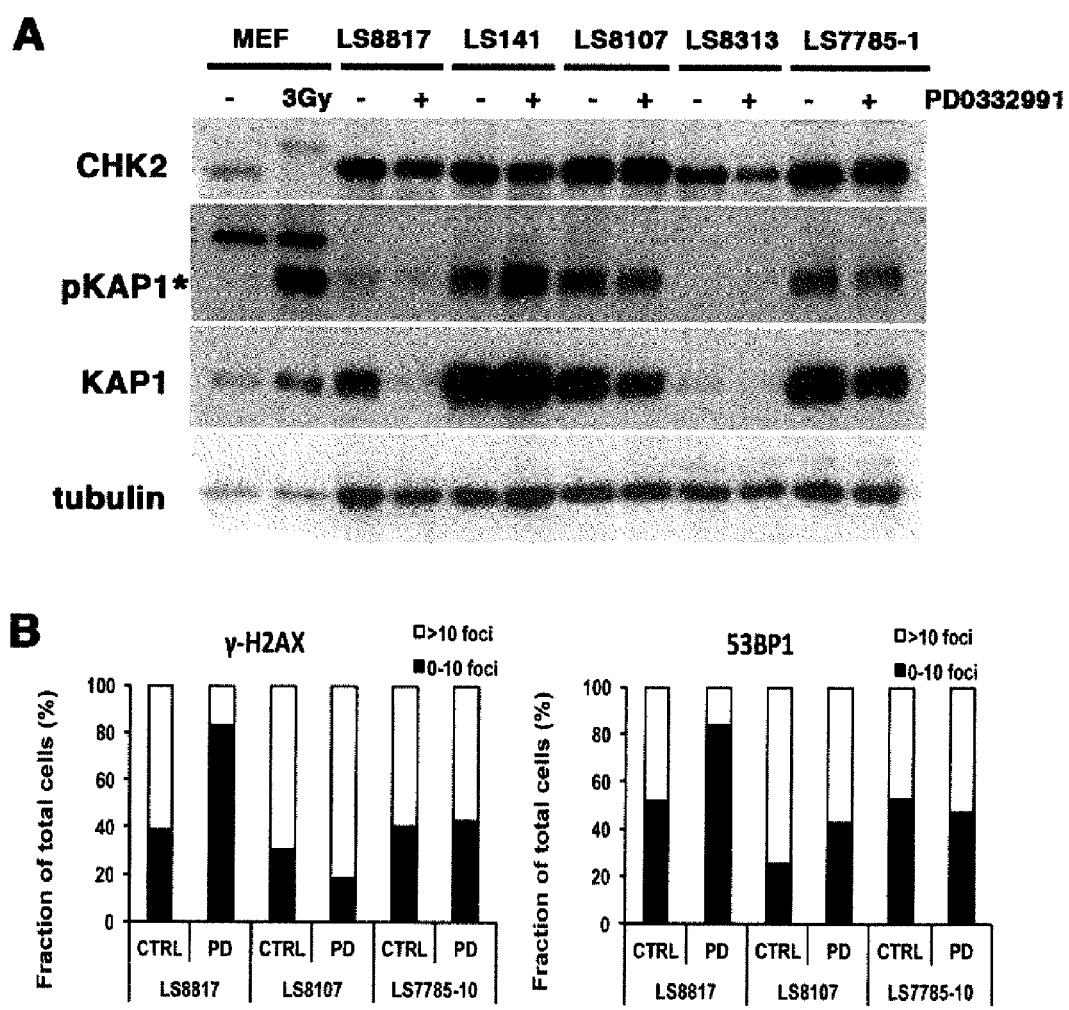

FIG. 23A-B. PD0332991 has little effect on indices of ATM activation, but does resolve DNA damage foci in responder cells. (A) CHK2, phosphoKAP1 and total KAP1 were measured as markers of ATM activity in PD0332991 treated cells. Extracts from control and irradiated mouse embryo fibroblasts were included as a control. Tubulin is a control. (B) γH2AX and 53BP1 foci were scored in the indicated cell lines. As per (Doll et al., 2009; Panier et al., 2012) having a cell with greater than 10 foci (white) is considered positive for DNA damage. As expected for WD/DDLS cell lines the basal level of DNA damage was quite high. Even though all cell lines exit the cell cycle PD0332991 leads to the resolution of the damage foci in the responder LS8817, but not the non-responders LS8107 and LS7785-10.

Figure 24:
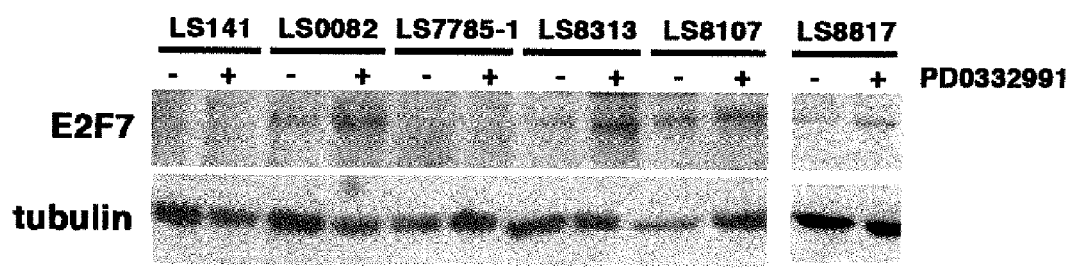

FIG. 24. PD0332991 induced senescence did not correlate with induction of either E2F7, or catalase, a marker of reactive oxygen species. E2F7 levels were measured by immunoblot 48 hours after PD0332991 treatment in the indicated cell lines. Tubulin is a loading control. This experiment was repeated at least twice for each cell line.

FIG. 25A-D. Turnover of MDM2 is regulated post-translationally. (A) The cell lines indicated were treated with PD0332991 for two days, after which 5 µM MG132 was added and incubation continued for an additional 2 hours. Extracts were prepared and MDM2 was immunoprecipitated and the presence of HAUSP and MDM2 in the precipitates were determined by immunoblot. IgG was used as a non-specific antibody control for the immunoprecipitation. (B) The cell lines were either asynchronously growing or treated with PD0332991 for 2 days and the expression of HAUSP and MDM2 measured by immunoblot. Tubulin is a loading control. HAUSP levels were reduced with shRNA in the indicated cells lines and the effect on protein expression (C) and the accumulation of senescence-associated (3-galactosidase positive cells measured (D). The mean and standard deviation was compiled from at least two independent experiments with each cell line and a representative immunoblot is shown.

FIG. 26A-B. p53 is not required for PD0332991 or MDM2 knockdown induced senescence in LS8817 cells. LS8817 cells were infected with lentiviruses expressing either a scrambled (shSCR) or two independent p53 targeting (shp53a and shp53d2) shRNAs. After selection these cells were either treated with PD0332991 (A) or MDM2 was reduced by superinfection with a lentivirus expressing shM380 (B). The accumulation of senescence associated β-galactosidase (top), and the expression of MDM2 and p53 were determined by immunoblot (bottom). Coomassie staining of the gel indicated equivalent loading.

Figure 27:
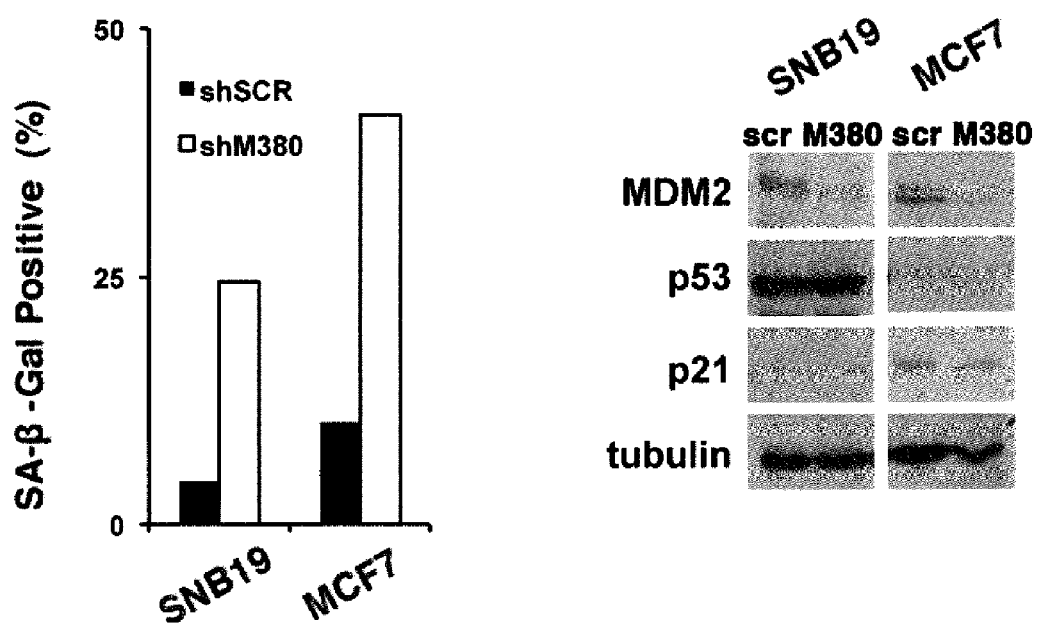

FIG. 27. MDM2 was knocked down in SNB19 and MCF7 cells and the effect on accumulation of senescence associated β-galactosidase positive cells (left) and p53 and p21 are shown (right). This experiment was repeated twice.

5. DETAILED DESCRIPTION OF THE INVENTION

For clarity and not by way of limitation the detailed description of the invention is divided into the following subsections:
(i) MDM2 as a biomarker;
(ii) CDK4 inhibitors;
(iii) cancer targets;
(iv) methods of use; and
(v) kits.

5.1 MDM2 as a Biomarker

Mouse double minute 2 is denoted MDM2 herein.

A subject may be human or a non-human subject. Non-limiting examples of non-human subjects include non-human primates, dogs, cats, mice, rats, guinea pigs, rabbits, pigs, fowl, horses, cows, goats, sheep, cetaceans, etc.

In certain non-limiting embodiments, a MDM2 biomarker may be a protein.

In a specific, non-limiting embodiment, a MDM2 protein may be a human MDM2 protein having the amino acid sequence as set forth in NCBI database accession no. NP_002383 (SEQ ID NO:1).

MDM2 nucleic acids and proteins for non-human species are known or can be determined according to methods known in the art, for example, where the sequence is the allele represented in the majority of the population.

In a specific, non-limiting embodiment, a MDM2 protein may be a mouse MDM2 protein having the amino acid sequence as set forth in NCBI database accession no. NP_034916 (SEQ ID NO:2).

In a specific, non-limiting embodiment, a MDM2 protein may be a rat MDM2 protein having the amino acid sequence as set forth in NCBI database accession no. NP_001101569 (SEQ ID NO:3).

A MDM2 biomarker is a biomarker, which manifests as decreased MDM2 expression levels following treatment with a CDK4 inhibitor, relative to a reference standard level. A reference standard level of MDM2 may, for example, be established using a reference standard such as cancer cells from the subject prior to treatment with a CDK4 inhibitor or in a parallel culture of the subject's cancer cells.

In certain, non-limiting embodiments of the invention, a level of a MDM2 biomarker may be evaluated by evaluating MDM2 function, where the MDM2 level is directly proportional to the level of MDM2 function.

In particular non-limiting embodiments, a reduction in MDM2 biomarker level means a reduction of at least a statistically significant amount, or at least about ten percent, or at least about twenty percent, or at least about thirty percent, or at least about forty percent, or at least about fifty percent, relative to the reference standard level.

Methods for detecting and/or determining the level of a protein biomarker include, but are not limited to, mass spectrometry techniques, 1-D or 2-D gel-based analysis systems, chromatography, protein microarray, immunofluorescence, enzyme linked immunosorbant assays (ELISAs), radioimmunoassay (RIA), enzyme immunoassays (ETA), Western Blotting and other immunoglobulin-mediated assays, and other techniques known in the art.

In certain, non-limiting embodiments, one method that can be used for detecting a MDM2 biomarker is Western blotting. Cells can be harvested by trypsinization and homogenized and/or sonicated in lysis buffer. Lysates can be clarified by centrifugation and subjected to SDS-PAGE followed by transfer to a membrane, such as a polyvinylidene difluoride (PVDF) membrane. Antibodies (unlabeled), specific to a biomarker, e.g., MDM2, can then brought into contact with the membrane and assayed by a secondary immunological reagent, such as labeled anti-immunoglobulin. Non-limiting examples of labels include, but are not limited to, $^{125}$I, horseradish peroxidase and alkaline phosphatase. In certain embodiments, immunodetection can be performed with antibody to a biomarker using the enhanced chemiluminescence system (e.g., from PerkinElmer Life Sciences, Boston, Mass.). The membrane can then be stripped and re-blotted with a control antibody, e.g., anti-tubulin. In certain embodiments, the level of a biomarker can be normalized against the level of a control protein, e.g., tubulin or actin, detected in the same sample.

In certain, non-limiting embodiments, immunohistochemistry can be used for detecting a MDM2 biomarker. For example, a first antibody can be brought into contact with a sample, e.g., a thin layer of cells, followed by washing to remove unbound antibody, and then contacted with a second, labeled antibody. Labeling can be by fluorescent markers, enzymes, such as peroxidase, avidin or radiolabeling. In certain embodiments, the first antibody can be conjugated to a fluorophore for direct detection. The labeling can be scored visually using microscopy and the results can be quantitated.

5.2 CDK4 Inhibitors

Non-limiting examples of CDK4 inhibitors include compounds that inhibit the kinase activity of CDK4. Additional non-limiting examples of CDK4 inhibitors include ATP-competitive inhibitors of CDK4. In particular non-limiting embodiments, the CDK4 inhibitor is derived from pyridopyrimidine, pyrrolopyrimidine or indolocarbazole compounds. Further non-limiting examples of CDK4 inhibitors include Palbociclib Isethionate, LEE011 (CAS Number 1211441-98-3), LY2835219 (CAS Number 1231930-82-7), PD0332991 and Flavopiridol Hydrochloride. Additional CDK4 inhibitors are disclosed in U.S. Pat. Nos. 6,630,464 and 6,818,663, and U.S. Patent Application Nos. U.S. 2012/0244110, 2012/0207763 and 2011/0152244.

Further non-limiting examples of CDK4 inhibitors include antisense oligonucleotides, shRNA molecules and siRNA molecules that specifically inhibit the expression or activity of CDK4. One non-limiting example of a CDK4 inhibitor comprises an antisense, shRNA, or siRNA nucleic acid sequence homologous to at least a portion of a CDK4 nucleic acid sequence, wherein the homology of the portion relative to the CDK4 sequence is at least about 75 or at least about 80 or at least about 85 or at least about 90 or at least about 95 or at least about 98 percent, where percent homology can be determined by, for example, BLAST or FASTA software. In certain non-limiting embodiments, the complementary portion may constitute at least 10 nucleotides or at least 15 nucleotides or at least 20 nucleotides or at least 25 nucleotides or at least 30 nucleotides and the antisense nucleic acid, shRNA or siRNA molecules may be up to 15 or up to 20 or up to 25 or up to 30 or up to 35 or up to 40 or up to 45 or up to 50 or up to 75 or up to 100 nucleotides in length. In certain embodiments, the CDK4 inhibitor is a shRNA comprising the nucleic acid sequence GAGAT-TACTTTGCTGCCTTAA (SEQ ID NO:4). shRNA Antisense, shRNA or siRNA molecules may comprise DNA or atypical or non-naturally occurring residues, for example, but not limited to, phosphorothioate residues.

5.3 Cancer Targets

Non-limiting examples of cancers that may be subject to the present invention include liposarcoma, glioma (or glioblastoma), osteosarcomas, melanoma, oligodendroglioma, astrocytoma, neuroblastoma, pancreatic neuroendocrine tumors and breast cancer.

5.4 Methods of Use

In certain non-limiting embodiments, the present invention provides for a method of determining whether an anti-cancer effect is likely to be produced in a cancer by a CDK4 inhibitor, comprising, determining the expression level of a MDM2 biomarker in a cancer, where if the expression level of the MDM2 biomarker is reduced in the cancer in response to CDK4 inhibition, it is more likely that the CDK4 inhibitor would have an anti-cancer effect on the cancer. For example, the reduction may be appreciated by comparing the level of MDM2 biomarker in the cancer consequent to CDK4 inhibitor treatment to a reference standard as described above.

MDM2 biomarkers are described in the sections above. CDK4 inhibitors are described above. Cancers suitable for treatment are described above.

In certain non-limiting embodiments, the present invention provides for a method for determining whether an anti-cancer effect is likely to be produced in a cancer by a CDK4 inhibitor, comprising, obtaining a sample of the cancer before and after treatment with a CDK4 inhibitor, and determining, in the samples, the expression level of a MDM2 biomarker, where if the MDM2 biomarker expression level is decreased following treatment with a CDK4 inhibitor, it is more likely that a CDK4 inhibitor would have an anti-cancer effect on the cancer. Methods for determining the expression levels of a MDM2 biomarker are set forth in section 5.1 above. As stated supra, the reduction may be appreciated by comparing the level of MDM2 biomarker in the cancer consequent to CDK4 inhibitor treatment to a reference standard level. For example, but not by way of limitation, the reference standard level can be established using cancer cells from the subject prior to treatment with a CDK4 inhibitor.

An anti-cancer effect means one or more of a reduction in aggregate cancer cell mass, a reduction in cancer cell growth rate, a reduction in cancer cell proliferation, a reduction in tumor mass, a reduction in tumor volume, a reduction in tumor cell proliferation, a reduction in tumor growth rate, a reduction in tumor metastasis and/or an increase in the proportion of senescent cancer cells.

In certain non-limiting embodiments, the present invention provides for a method for producing an anti-cancer effect by a CDK4 inhibitor in a subject, comprising, obtaining a sample of the cancer before treatment of the subject with a CDK4 inhibitor, and determining, in one or more cancer cell from the sample, the effect of treatment with the CDK4 inhibitor on the level of MDM2 biomarker, where if the MDM2 biomarker expression level is decreased following treatment with the CDK4 inhibitor, then initiating treatment of the subject with a therapeutically effective amount of the CDK4 inhibitor.

In certain non-limiting embodiments, the present invention provides for a method for producing an anti-cancer effect by a CDK4 inhibitor, comprising, obtaining a sample of the cancer after treatment with a CDK4 inhibitor, and determining, in one or more cancer cell from the sample, the expression level of a MDM2 biomarker, where if the MDM2 biomarker expression level is decreased following treatment with a CDK4 inhibitor, then continuing or resuming treatment of the subject with a therapeutically effective amount of a CDK4 inhibitor. Optionally, a sample may be collected before and after treatment and the MDM2 levels compared.

In certain non-limiting embodiments, the present invention provides for a method for producing an anti-cancer effect by a CDK4 inhibitor, wherein the CDK4 inhibitor used to treat a subject after the detection of a decrease in MDM2 expression levels may be the same or different from the CDK4 inhibitor administered during the determination of the MDM2 expression level change in the subject. In certain non-limiting embodiments, the CDK4 inhibitor used to treat the subject after the detection of a decrease in MDM2 expression levels may be of the same or different chemical class than the CDK4 inhibitor administered during the determination of the MDM2 expression level change in the subject. In certain non-limiting embodiments, the CDK4 inhibitor used to treat the subject after the detection of a decrease in MDM2 expression levels may function by a similar or different mechanism than the CDK4 inhibitor administered during the determination of the MDM2 expression level change in the subject.

In certain non-limiting embodiments, the present invention provides for a method for treating a subject having a cancer, comprising, obtaining a sample of the cancer before treatment of the subject with a CDK4 inhibitor, and determining, in one or more cancer cell from the sample, the effect of treatment with the CDK4 inhibitor on the level of MDM2 biomarker, where if the MDM2 biomarker expression level is decreased following treatment with the CDK4 inhibitor, then initiating treatment of the subject with a therapeutically effective amount of the CDK4 inhibitor.

In certain non-limiting embodiments, the present invention provides for a method for treating a subject having a cancer, comprising, obtaining a sample of the cancer after treatment with a CDK4 inhibitor, and determining, in the sample, the expression level of a MDM2 biomarker, where if the MDM2 biomarker expression level is decreased following treatment with a CDK4 inhibitor as compared to a reference standard level, then continuing or resuming treatment of the subject with a therapeutically effective amount of a CDK4 inhibitor. Optionally, a sample may be collected before and after treatment and the MDM2 levels compared.

Any of the foregoing methods may comprise a step of collecting one or more cancer cell sample from the subject, where a cell or cells from the subject may be used to determine the effect of CDK4 inhibitor of MDM2 biomarker level.

Any of the foregoing methods may further comprise a step of detecting one or more marker for senescence in a sample following treatment with a CDK4 inhibitor.

Any of the foregoing methods may further comprise determining the level of phosphorylated RB in a sample following treatment with a CDK4 inhibitor, where if the level of phosphorylated-RB is decreased following treatment with a CDK4 inhibitor, it is more likely that the CDK4 inhibitor has reduced the kinase activity of CDK4. In certain embodiments, the reduction may be appreciated by comparing the level of phosphorylated-RB in the cancer consequent to CDK4 inhibitor treatment to a reference level. A reference level of phosphorylated-RB may, for example, be established using cancer cells from the subject prior to treatment with a CDK4 inhibitor or in a parallel culture of the subject's cancer cells.

In certain non-limiting embodiments, a sample includes, but is not limited to, a clinical sample, cells in culture, cell supernatants, cell lysates, serum, blood plasma, biological fluid (e.g., lymphatic fluid) and tissue samples. The source of the sample may be solid tissue (e.g., from a fresh, frozen, and/or preserved organ, tissue sample, biopsy or aspirate), blood or any blood constituents, bodily fluids (such as, e.g., urine, lymph, cerebral spinal fluid, amniotic fluid, peritoneal fluid or interstitial fluid), or cells from the individual, including circulating tumor cells. In certain non-limiting embodiments, the sample is obtained from a tumor.

In certain non-limiting embodiments, where the expression level of a MDM2 biomarker is not decreased in cancer cells following treatment with a CDK4 inhibitor, the subject from whom the cancer cells derive is treated with another modality, for example, an alternative chemotherapeutic agent, biologic anticancer agent, or radiation therapy, is administered.

A therapeutically effective amount is an amount that is able to achieve one or more of an anticancer effect, prolongation of survival and/or prolongation of period until relapse. Methods of determining levels of MDM2 biomarkers are set forth in preceding section 5.1.

5.5 Kits

In non-limiting embodiments, the present invention provides for a kit for determining whether an anti-cancer effect is likely to be produced in a cancer by a CDK4 inhibitor, comprising a means for detecting the expression level of a biomarker. MDM2 biomarkers and method for measuring MDM2 biomarker levels are described in the sections above.

Types of kits include, but are not limited to, arrays/microarrays, biomarker-specific antibodies and beads, which further contain one or more probes, antibodies, or other detection reagents for detecting one or more biomarker of the present invention.

In non-limiting embodiments, the present invention provides for a kit for determining whether the anti-cancer effect is likely to be produced in a cancer by a CDK4 inhibitor, comprising a means for detecting the protein levels of a biomarker.

In non-limiting embodiments, a kit may comprise at least one antibody for immunodetection of the biomarker(s) to be identified. Antibodies, both polyclonal and monoclonal, including molecules comprising an antibody variable region or MDM2 subregion thereof, specific for a MDM2 biomarker, may be prepared using conventional immunization techniques, as will be generally known to those of skill in the art. The immunodetection reagents of the kit may include detectable labels that are associated with, or linked to, the given antibody or antigen itself. Such detectable labels include, for example, chemiluminescent or fluorescent molecules (rhodamine, fluorescein, green fluorescent protein, luciferase, Cy3, Cy5, or ROX), radiolabels ($^3$H, $^{35}$S, $^{32}$P, $^{14}$C and $^{131}$I) or enzymes (alkaline phosphatase, horseradish peroxidase). Alternatively, a detectable moiety may be comprised in a secondary antibody or antibody fragment which selectively binds to the first antibody or antibody fragment (where said first antibody or antibody fragment specifically recognizes MDM2).

In a further non-limiting embodiment, the MDM2 biomarker-specific antibody may be provided bound to a solid support, such as a column matrix, an array, or well of a microtiter plate. Alternatively, the support may be provided as a separate element of the kit.

In one specific non-limiting embodiment, a kit may comprise a probe, microarray, or antibody suitable for detecting a MDM2 biomarker.

In one specific non-limiting embodiment, a kit may further comprise a probe, microarray, or antibody suitable for detecting phosphorylated-RB.

In certain non-limiting embodiments, where the measurement means in the kit employs an array, the set of biomarkers set forth above may constitute at least 10 percent or at least 20 percent or at least 30 percent or at least 40 percent or at least 50 percent or at least 60 percent or at least 70 percent or at least 80 percent of the species of markers represented on the microarray.

In certain non-limiting embodiments, a kit may further contain means for detecting a marker for senescence. For example, in certain non-limiting embodiments, the kit may further comprise an antibody suitable for detecting senescence-associated heterochromatic foci (SAHF), e.g., an antibody specific for HP1γ. In certain non-limiting embodiments, the kit may comprise an antibody suitable for detecting senescence-associated β-galactosidase.

In certain non-limiting embodiments, a kit may further comprise a probe, microarray, or antibody suitable for detecting Retinoblastoma (RB) protein levels. For example, the kit may comprise an a probe, microarray, or antibody suitable for detecting the phosphorylated form of RB (e.g., p-RB Ser780).

In certain non-limiting embodiments, a biomarker detection kit may comprise one or more detection reagents and other components (e.g., a buffer, enzymes such as alkaline phosphatase, antibodies, and the like) necessary to carry out an assay or reaction to determine the expression levels of a biomarker.

In certain non-limiting embodiments, a kit may further contain means for comparing the biomarker with a reference standard. For example, in certain non-limiting embodiments, the kit may further comprise an a probe, microarray, or antibody suitable for detecting protein that can be used a control for normalizing protein expression levels. Non-limiting examples of such proteins include tubulin and actin.

A kit may further include instructions for using the kit to determine the expression level of the MDM2 biomarker. Specifically, the instructions describes that the decrease in expression levels of a MDM2 biomarker following treatment with a CDK4 inhibitor, set forth herein, is indicative of an increased possibility of an anti-cancer effect in a cancer by a CDK4 inhibitor.

6. EXAMPLE 1: MDM2 MODULATES THE CELLULAR SENESCENCE RESPONSE TO CDK4 INHIBITION

To identify the types of cellular response induced by either CDK4 or MDM2 inhibition in well-differentiated and dedifferentiated liposarcomas (WD/DDLS), we pharmacologically or genetically manipulated the expression of these proteins or their activities in a collection of RB-positive patient-derived cell lines. These lines had amplification of MDM2 and CDK4 but were otherwise genetically diverse.

MDM2 inhibitors include the Nutlin class of drugs (e.g., Nutlin-3a and RG7112). Nutlin-3a mimics three residues of the transactivation domain of p53 and competes with p53 to bind MDM2 allowing the accumulation of transcriptionally active p53. Additionally, it can impact the interaction of MDM2 with E2F1, p73, HIF-1α, and NUMB (11). The ability of these imidazoline compounds to induce growth arrest or apoptosis and their synergy with other agents are the subject of ongoing investigation; for example, signaling through the mTOR pathway can reduce the apoptotic activity of nutlins (12, 13)

PD0332991 is a highly selective CDK4/6 inhibitor that has very low toxicity in animals (14). PD0332991 can induce G1 arrest in both normal and tumor cells (15) and has entered clinical trials in a number of cancers including WD/DDLS (51). This drug has no effect on the proliferation of RB-negative cells, thus, demonstrating its specificity for these kinases. However, neither an intact RB locus nor the presence of lesions that activate CDK4, such as a CDK2NA deletion, can predict whether or not PD0332991 will inhibit cell proliferation (16).

We found that amplification or activity of CDK4 correlated with the accumulation of MDM2 protein from the amplified locus in some cells, and sustained MDM2 protein expression in quiescent cells played a critical role suppressing an RB-associated senescence pathway. Furthermore, looking at the response of patients to PD0332991 and measuring the amount of MDM2 in pre- and post-treatment biopsies, we found that reductions in MDM2 were correlated to favorable outcome.

6.1 Materials and Methods

Cell Line Culture, Differentiation and Validation.

Cell lines were developed from WD/DDLS tumors resected from surgical patients after obtaining informed consent. LS8817 and LS0082 have previously been described using the nomenclature DDLS8817 and WD0082. DNA was extracted from cell lines using standard protocols (QIAGEN DNEasy) and lineage confirmed by copy number array to confirm amplification of segment 12q13-15 (Agilent 244K according to manufacturer's specifications). Analysis of comparative genomic hybridization data was performed using a custom pipeline, which conducts the standard circular binary segmentation from the R/bioconductor DNA copy library and processes all samples with the RAE algorithm (47).

Cell lines were maintained in DMEM High glucose (HG) supplemented with 10% heat-inactivated fetal bovine serum. Glioma cell lines, DKMG, SNB19, DBTRG-05MG, and T89G, were maintained in DMEM HG supplemented with 10% fetal bovine serum and 2 mM glutamine. The MCF7 breast cancer cell line was maintained in RPMI-1640 media supplemented with 10% fetal bovine serum and 2 mM glutamine. RNA was extracted from cells (RNEasy, QIAGEN) and reverse transcription performed (22) after treatment for 7 days with PD0332991 (Selleckchem) or differentiation media as previously described (21).

Gene Targeting by shRNA.

shRNA were delivered in the pLKO.1 vector (Sigma) and infected cells selected using puromycin (1 μg/ml); infection with a virus carrying a scramble control (CAACAAGAT-GAAGAGCACCAA) was used as a control in all experiments utilizing shRNA. Cell lines were treated with PD0339221 or shRNA directed against CDK4 (GAGAT-TACTTTGCTGCCTTAA (SEQ ID NO:4)), MDM2 (M376, TTCACTATTCCACTACCAAAG (SEQ ID NO:5); M380, TACTAGAAGTTGATGGCTGAG (SEQ ID NO:6)), HAUSP (4057, CCAGCTAAGTATCAAAGGAAA (SEQ ID NO:7); 845, CGTGGTGTCAAGGTGTACTAA (SEQ ID NO:8)) or CDK6 (GACCTGGAAAGGTGCAAAGAA (SEQ ID NO:9)) for 48 hours to 7 days and stained with BrdU (20 μM for two hours) or annexin V as previously described (22, 48). G0 content was determined by staining with propidium iodine and FACS analyses (49).

Proliferation and Apoptosis Assays.

Cells were stained with BrdU (20 μM for two hours) or annexin V as previously described (22, 48). G0 content was determined by staining with propidium iodine and FACS analyses (49).

Senescence Analyses.

Cells were plated at a concentration of 25,000 per well in a 4-well chamber slides (Lab-Tek) and treated for seven days with drug or shRNA as described above and stained for senescence-associated β-galactosidase (Cell Signaling kit #9860). Cell number was quantitated by DAPI staining and β-galactosidase staining quantitated as a proportion of total cells. Senescence associated heterochromatic foci were quantitated after cells were fixed with 4% paraformaldehyde, permeabilized with 0.1% Triton, blocked with 2% FBS, and stained with antibodies against HP1γ (1:5000 dilution, 2MOD-1G6 Millipore). Senescent cells were identified by immunofluorescence after treatment of slides with anti-mouse secondary antibodies and quantitation of focal SAHF as a percent of total cells (Leica Upright Confocal SP5 confocal microscope). Actin was marked using phalloidin staining (1:500, Invitrogen) and cells were counter-stained with DAPI. Cell area was measured by with Metamorph software to calculate relative area per cell.

Human cytokine arrays were purchased from R&D Technologies (ARY006). Cells were treated in 10 cm dishes with 1 μM PD0332991 or were left untreated as a control. The media was changed 24 hours prior to harvest. On the day of harvest, the media was collected, spun for 5 minutes at 1200 rpm and filtered through a 45 μM syringe to remove debris. Cells were trypsinized and counted and media volume was adjusted so that an equal number of cells were represented from each sample. Cytokine arrays were performed according to manufacturer's protocol. Signal intensity was measured using ImageJ and a $\log_2$ value of the PD/CTRL ratio was calculated.

Immunoblot.

Antibodies against CDK4 (3F121), MDM2 (N-20 and SMP14), total RB (IF8), Cyclin A (H432), p16 (C20), p53 (DO-1 and Bp53-12), tubulin (C20) and FLAG (M2) were obtained from Santa Cruz Biotechnology, phospho-Rb 780 (#9307) from Cell Signalling, and ARF (3642) from Abcam, HAUSP (A300-033A) from Bethyl Laboratories. Treated cells were lysed with buffer composed of 50 mM Tris-HCl, pH7.4, 250 mM NaCl, 5 mM EDTA, 0.5% NP40, 2 mM PMSF, and supplemented with protease inhibitors. Eighty micrograms of protein were resolved by SDS-PAGE and transferred to PVDF membranes. Membranes were incubated overnight with antibodies (1:1000). Extracts were prepared from pre- and post-treatment biopsies of patients treated with 125 mg PD0332991 daily for 3 weeks followed by one week of rest. Cycles were repeated every four weeks and patients are still on trial. Pre-treatment biopsies were collected within two weeks of the first dose and post-treatment biopsies collected after at least three weeks of treatment. Extracts were prepared in 50 mM Tris-HCl, pH7.4, 150 mM NaCl, 1 mM EDTA, 1% NP40, 0.25% sodium deoxycholate and supplemented with mini-protease inhibitor cocktail (Roche). Tumor response was assessed by reference radiologist by CT scan every six weeks for 36 weeks, and every 12 weeks thereafter. The clinical trial was approved by the Institutional Review Board of Memorial Sloan-Kettering Cancer Center and all patients provided written informed consent (NCT01209598).

Wobble Rescue.

Cells were first infected with a lentivirus (pLOC, Open Biosystems) encoding either an MDM2 expression cassette containing the mismatched sequence (ACTATTCTCAAC-CCTCAACTTCTA (SEQ ID NO:10)) or RFP cassette. 24 hours later, transduced cells were selected for in media containing 3 μg/ml blasticidin and selection was maintained throughout the experiment. Five days after blasticidin selection began, we transduced the cells with a second lentiviral vector encoding either the shM380 sequence targeting MDM2 or a scrambled sequence (shSCR) as described above. 24 hours later these cells were selected in media containing both blasticidin and 3 puromycin.

MDM2 Turnover.

250,000 cells were seeded in 6 cm dishes and treated with 1 μM PD0332991 for 48 hrs. Media was then removed and replaced with media containing 75 μg/mL cycloheximide (and PD0332991 as necessary). Plates were harvested at the indicated time points and cells were processed for immunoblot as described above. Signal intensity was measured using ImageJ and was normalized to the corresponding tubulin intensity. Data was plotted and best fit single phase decay was calculated using GraphPad Prism 6.

6.2 Results

Pharmacologic Inhibition of CDK4 can Induce Senescence in a Subset of RB-Positive Liposarcoma Cell Lines.

CDK4 small molecule inhibitors potently inhibit cell proliferation in an RB-dependent manner. In some circumstances, these quiescent cells can undergo senescence, a specialized form of growth arrest, albeit the mechanism driving this transition is not completely understood (17, 18). To determine how CDK4 inhibition would affect WD/DDLS, we treated a collection of seven RB-positive patient derived cell lines that all had common amplifications of MDM2 and CDK4 but also contained a heterogeneous assortment of passenger mutations and possibly additional alterations in driver mutations as well (FIG. 8) with PD0332991. Addition of PD0332991 to asynchronously growing cells resulted in growth arrest within a single cell cycle (FIG. 9A) with cells accumulating in G0/G1 (FIG. 9B) and a significant reduction in the incorporation of bromodeoxyuridine (BrdU; FIG. 1A). As expected, unphosphorylated RB accumulated in these cells (FIG. 1C) and on longer treatments the amount of RB decreased (data not shown) indicating that the drug hit the target. PD0332991 did not induce a significant change in annexin V staining, a marker of apoptosis, in any of the cell lines (FIG. 1B). With continued PD0332991 treatment, all seven cultured cell lines began to take on a confluent appearance. When we traced the cell perimeter after we stained these cultures with phalloidin, which highlights the actin cytoskeleton, it was clear that cells were enlarged. An increase in cell volume was also confirmed by flow cytometry. Representative data is shown in FIG. 10A-C.

In some circumstances quiescent cells undergo senescence, a specialized stable form of growth arrest (17, 18). The molecular pathways driving this transition are not completely understood. Senescent cells are often characterized by a flattened enlarged morphology (19). To determine if PD0332991 induced senescence in these cells, we measured the accumulation of perinuclear associated β-galactosidase (SA-β-gal) (FIG. 2A) and the accumulation of senescence associated heterochromatic foci (SAHF), as marked by HP1γ, a protein known to accumulate in these structures (20) (FIG. 2B). In three cell lines (LS8817, LS141 and LS0082), but not the other four (LS8107, LS7785-10, LS7785-1 and LS8313), a significant increase in the number of SA-β-gal or SAHF positive cells was observed by seven days after exposure to PD0332991 at concentrations as low as 100 nM. There was no increase in the number of SA-β-gal or SAHF positive LS7785-1, LS7785-10, LS8107 and LS8313 cells even when we increased the concentration of PD033299 ten-fold.

Consistent with these differences in the nature of the growth arrest between the cells lines, those that did not stain for SAHF or SA-β-gal (LS8107 and LS7785-1) after seven days of drug treatment returned to the cell cycle within 48 hours after the drug was removed (FIG. 2C). Those that did express senescence markers (LS8817 and LS0082) did not (FIG. 2C). Even at later time points, only limited BrdU incorporation was detected in the cultures containing cells that expressed senescence markers, which we believe to be those cells that did not undergo the transformation to senescence.

The ability of PD0332991 to induce senescence was not associated with the doubling time of the cells. LS8817, LS141, and LS0082 underwent senescence when treated with the drug, but LS8313 did not even though it grows as rapidly as the others (FIG. 9A).

Given the cellular evidence for senescence, we looked at the expression of Arf, p53 and p16, three proteins that typically accumulate in senescent cells (30, 28, 19), and a number of cytokines that are associated with the senescence associated secretory program (SASP; 54, 55, 38, 40, 41). We did not see any differences in the expression of Arf, p53 or p16 in two of the cell lines in which SA-β-gal and SAHF accumulated compared to two of the ones where they did not (FIG. 2D); surprisingly, the amount of p53 even decreased in the cell lines following drug treatment. Similar decreases in Arf and p53 were noted in the other cell lines as well. Reduced levels of cyclin A in drug treated cells confirmed that PD0332991 inhibited cell proliferation and hit its target.

Senescence can be associated with increased expression of a number of cytokines. This is defined as the senescence associated secretory program (SASP; 54, 55, 38, 40, 41). On the other hand, we did observe differences in cytokine secretion when comparing the LS8817 cell line, in which SA-β-gal and SAHF accumulated, to the LS8313 cell line where they did not. Of the 36 cytokines we queried on this protein array, 17 have been implicated as part of the SASP. Of these 17, seven were detectable in the media, a number consistent with prior studies on other non-fibroblast cell lines (56, 57). In LS8817, secretion of GM-CSF, GROα/CXCL1, IL-6, IL-8 and MCP-1 were upregulated following treatment with PD0332991. MIF-1 and PAI-1, two other detectable SASP factors, were essentially unchanged. In LS8313, only IL-6 secretion increased, and this was modest as compared to the change in levels seen in the LS8817 cells (FIG. 16). Similar patterns of cytokine expression were observed when comparing LS0082 and LS8107 cells, a second pair of cells that undergo senescence or quiescence, respectively.

Senescence can be triggered by accumulation of reactive oxygen species (ROS) or DNA damage. Thus, we looked at whether PD0332991 induced catalase expression in two cell lines that undergo PD0332991-induced senescence and two cell lines that do not. Catalase was increased in all four cell lines (FIG. 22), indicating that PD0332991 could increase ROS in both types of non-cycling cells, but this was not a key determinant of whether the cells senesced. Additionally, PD0332991 did not induce significant changes in CHK2 mobility or KAP1 phosphorylation, two markers of ATM activity, in the cell lines that underwent senescence (LS8817 and LS141) or those that quiesced (LS8107, LS8313, and LS7785-1). In contrast, these proteins were clearly increased after radiation induced DNA damage in mouse embryo fibroblasts (FIG. 23A). However, in LS8817 cells the number of γH2Ax and 5313P1 foci, markers of an activated DNA damage response, were reduced following PD0332991 treatment (FIG. 23B). The number of foci was largely unaffected in two other cell lines that underwent PD0332991 induced quiescence (LS8107 and LS7785-10, FIG. 23B). This indicates that ongoing DNA repair and DNA damage can be uncoupled from the PD0332991 induced senescence.

Recently the accumulation of E2F7 has also been reported in senescent cells (5). Although PD0332991 induced accumulation of E2F7 in LS8817, LS0082, and LS8313, the amount of the protein did not change in LS8107. E2F7 was undetectable in LS7785-1 and LS141 (FIG. 24). Thus, we could not correlate E2F7 induction with PD0332991 induced SA-β-gal and SAHF accumulation.

Alternative pathways in which cells accumulate in G0/G1, such as differentiation, i.e., adopting an alternative cell fate, might prevent the induction of a senescence program. We measured three markers of differentiated adipocytes, CEBPα, FABP4, and PPARγ mRNA in LS8107 and LS7785-10 cells, two of the cell lines that underwent growth arrest but not senescence. Expression of these markers was compared with expression when the cells were cultured under conditions that induce differentiation into adipocytes (21). None of these markers increased in PD0332991-treated cultures (FIG. 11), albeit they increased when the cells were cultured under differentiation-inducing conditions. Oil-Red O staining, which detects lipid droplets, were similarly not increased by PD0332991 in these and LS8313 and LS7785-1 cells. Thus, growth arrested cells that failed to senesce upon treatment with PD0332991 did not undergo differentiation.

Consequently, inhibiting CDK4 can induce two different responses in RB-positive WD/DDLS cell lines characterized by the amplification of MDM2 and CDK4: one in which cells undergo growth arrest and another in which growth arrest was associated with the induction of senescence. For simplicity, we refer to these subgroups as non-responders and responders, respectively.

Reducing CDK4 Protein Mimics the Effect of PD0332991 in RB-Positive Liposarcoma Cell Lines.

To address the specificity of PD0332991's effect, we also reduced CDK4 protein expression in two responder cell lines (LS8817 and LS0082) and two non-responder cell lines (LS8107 and LS7785-1) using two independent lentivirus encoding shRNA (FIG. 3A). Reducing CDK4 mimicked the cellular response to CDK4 inhibition; representative data for one of the hairpins is shown in FIG. 3A-D. In these four cell lines, abrogating CDK4 expression reduced the incorporation of BrdU (FIG. 3B), and decreased the level of both Cyclin A and phospho-RB indicating that the cells underwent a G1 arrest (FIG. 3A). p53 and ARF levels decreased equivalently in both responder and non-responder cell lines and p16 levels remained high (FIG. 3A). While all cell lines underwent growth arrest, SA-β-gal staining and SAHF significantly accumulated only in the responder cell lines (FIGS. 3C and 3D). Reducing expression of CDK6, another target of PD0332991, in two responder cell lines (LS8817 and LS0082) with shRNA only modestly reduced proliferation, cyclin A, phospho-Rb, and did not induce accumulation of SA-β-gal or SAHF (FIG. 12A-D). This indicated the importance of CDK4 for suppressing senescence in some of the WD/DDLS cell lines.

Changes in MDM2 Expression were Associated with the Senescence Promoting Effect of PD0332991.

Figure 12:
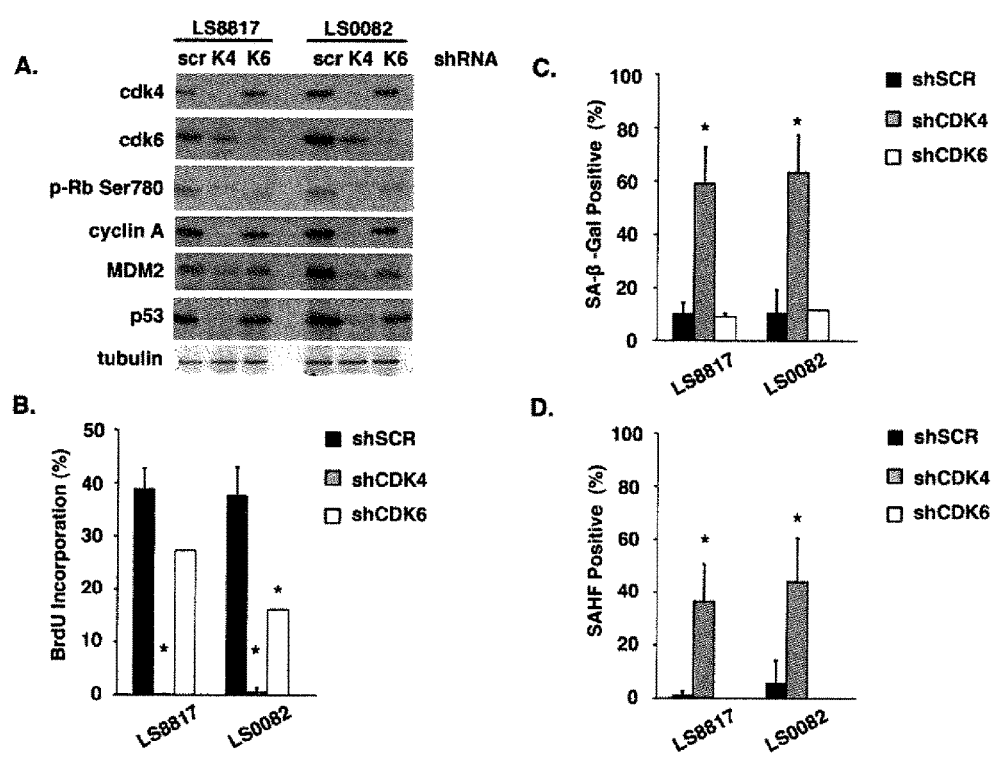

We also looked at whether MDM2 expression might be a determinant of the type of response to PD0332991. MDM2 levels were examined in responder and non-responder cells treated with PD0332991. MDM2 was reduced approximately three-fold in the PD0332991 treated responder cells (LS8817 and LS0082) which underwent senescence and not in the non-responders (LS8107 and LS7785-1) which underwent growth arrest (FIG. 5A). Similar results were seen with the LS141 responder cells and the LS7785-10 (FIG. 25B) and LS8313 non-responder cells. Furthermore, MDM2 levels were reduced by CDK4 knockdown in responder but not in non-responder cells (FIG. 5A). MDM2 levels were not reduced by CDK6 knockdown (FIG. 12A). In responder cells, MDM2 levels were not regulated in a growth or serum-dependent manner (unpublished data).

This data suggested a relationship between CDK4 activity, MDM2 levels, and senescence, further supported when we characterized another cell line, LS6736, which had amplification of MDM2 but not CDK4 (FIG. 8). The expression of MDM2 was remarkably low in these cells, especially in comparison with the other cell lines we were using (data not shown). These cells grew poorly, and there was an extraordinarily high percentage of SA-β-gal and SAHF (HP1γ) positive cells even in the absence of PD0332991 (FIGS. 14A and B). Adding PD0332991 did not increase the number of SA-β-gal and SAHF (HP1γ) positive cells further.

We attempted to infect these cells with a CDK4-expressing lentivirus to see if that would increase MDM2 levels or reduce the number of cells staining positive for SA-β-gal or HP1γ foci, but were unsuccessful in isolating transductants.

Figure 15:
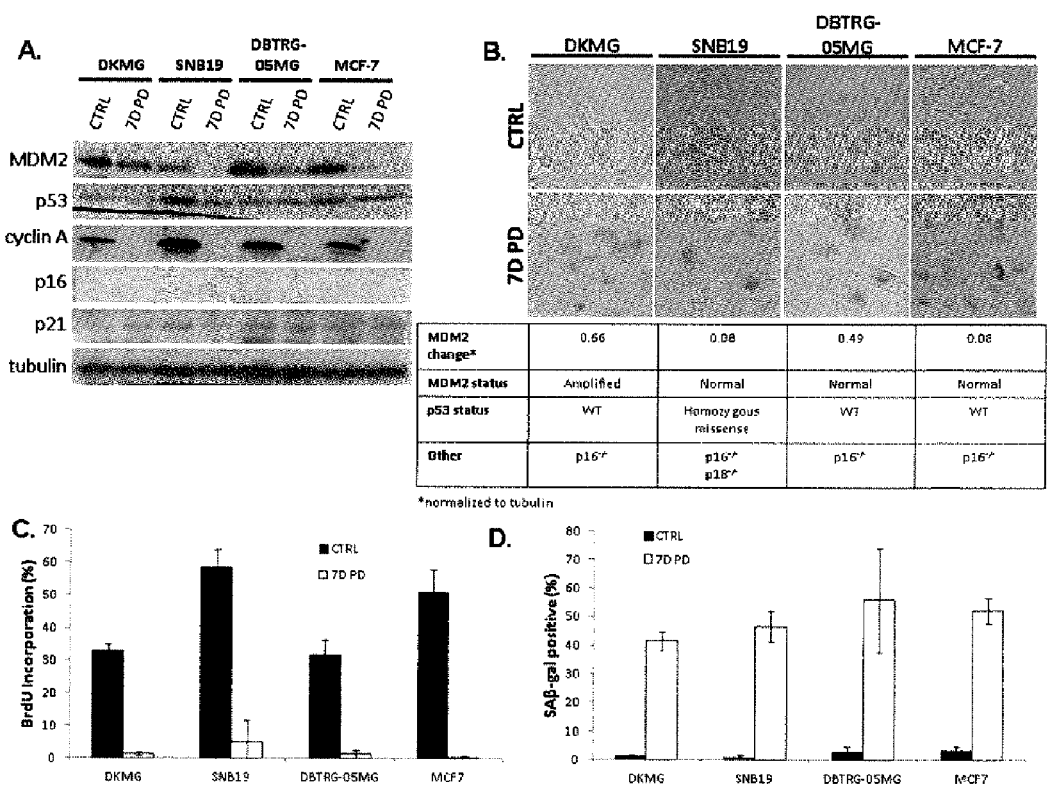

Additionally, we examined the MDM2 levels in various cancer cell lines in response to treatment with PD0332991 (FIG. 15A and Table 1). To determine if PD0332991 induced senescence in these cells, we measured the accumulation of perinuclear associated β-galactosidase (SA-β-gal) (FIG. 15D) and the incorporation of BrdU (FIG. 15C). In four cell lines (DKMG, SNB19, DBTRG-05MG, and MCF7), a significant increase in the number of SA-β-gal cells was observed seven days after exposure to PD0332991. In contrast, an increase in the number of SA-β-gal cells in the T98G cell line was not observed after treatment with PD0332991 (Table 1). In the glioma cells (DKMG, SNB19, and DBTRG-05MG) and the MCF-breast cancer cells (MCF7) that underwent senescence in response to treatment with PD033299, MDM2 expression levels were reduced greater than 34% compared to the non-treated cells, irrespective of p53 status (FIGS. 15A and B). MDM2 levels were unaffected in PD0332991 treated glioma cells (T98G) that did not undergo senescence (Table 1).

Figure 18C:
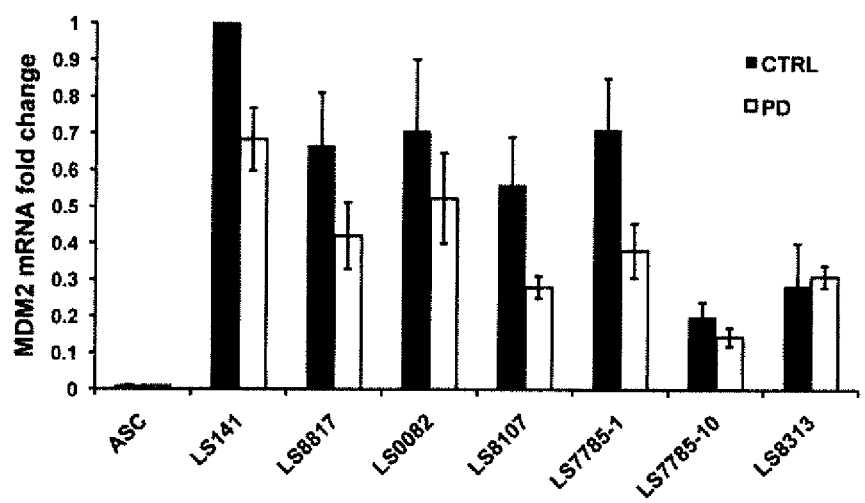
Figure 18D:
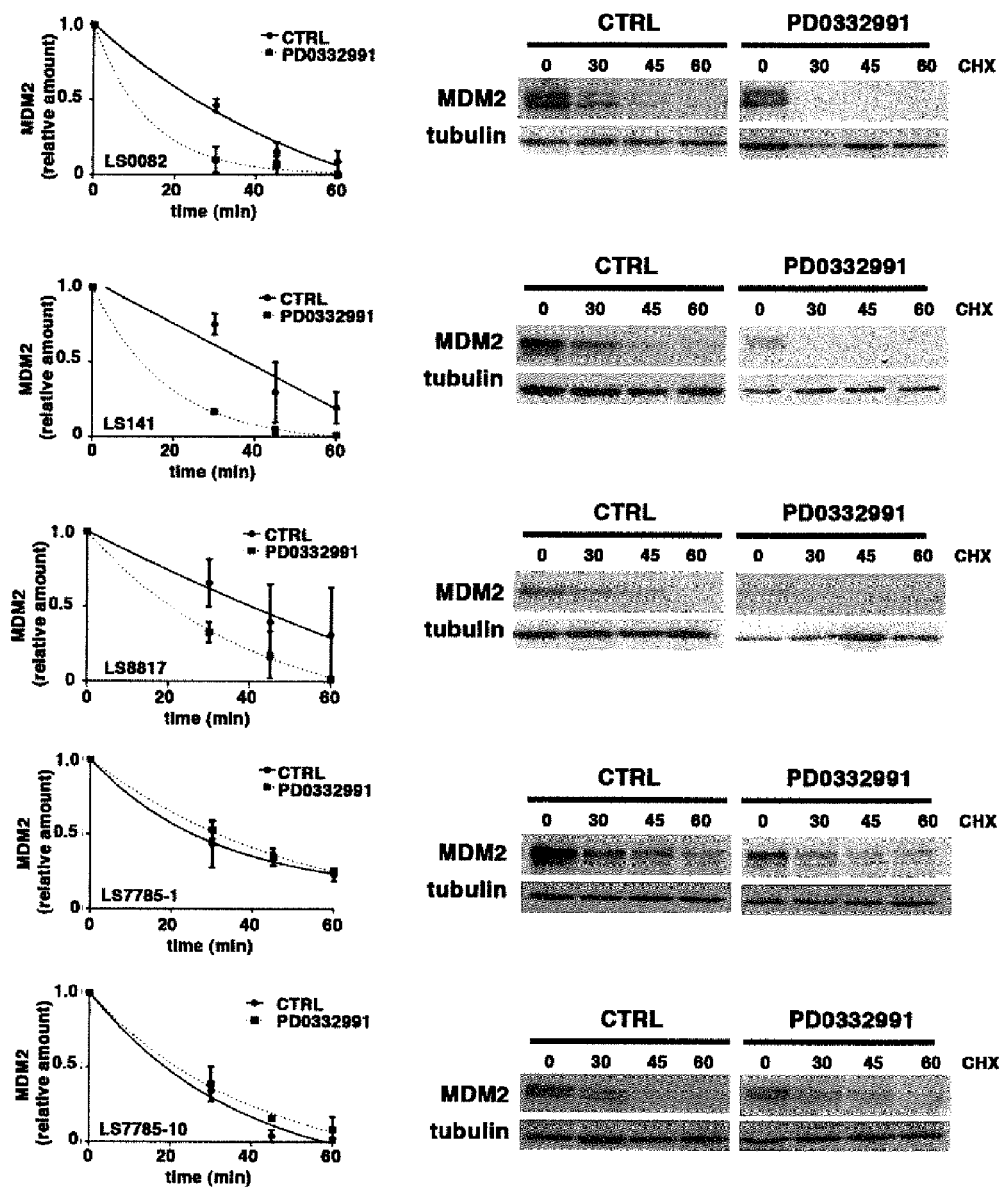
Figure 18E:
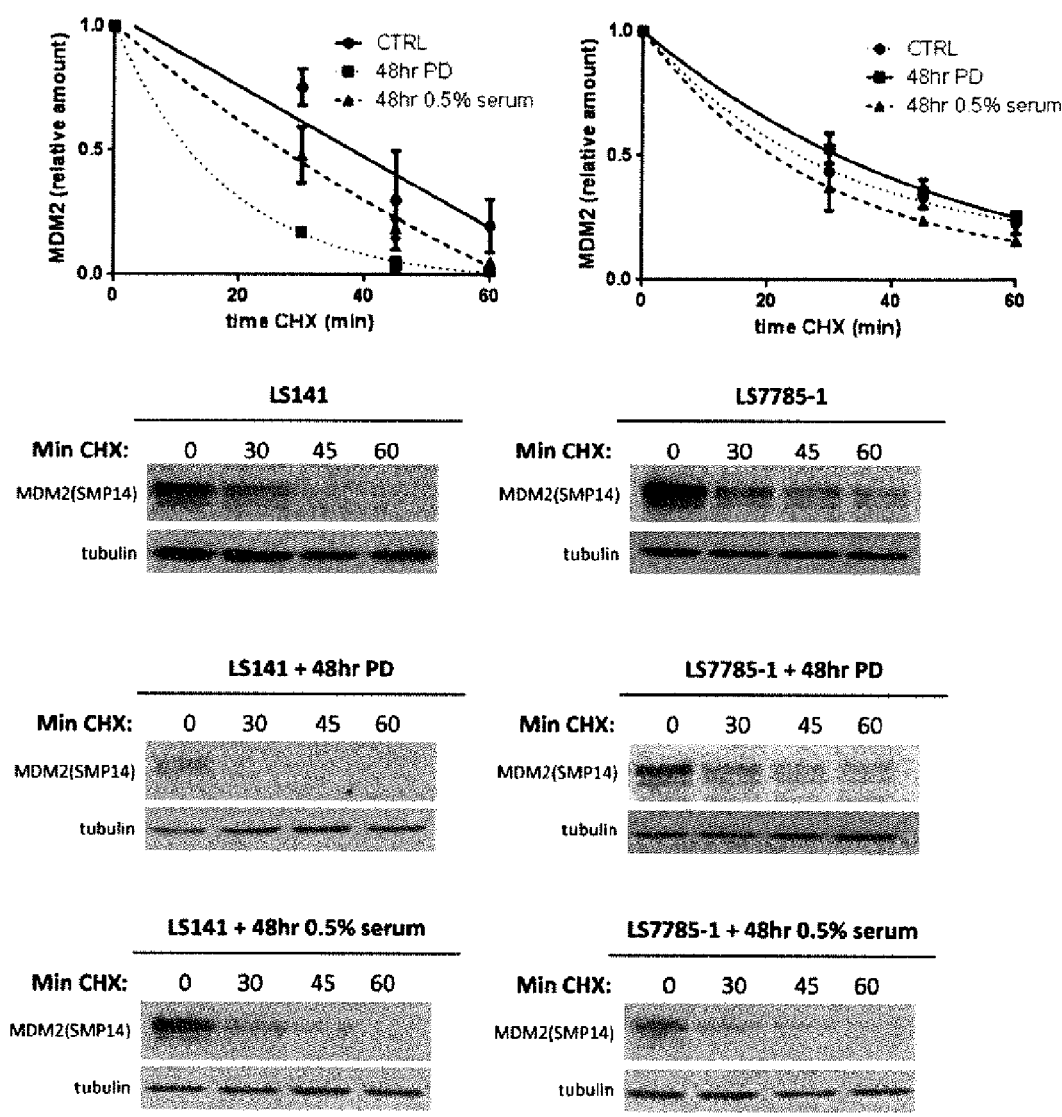

A key difference between responder and non-responder cell lines and those patients who performed well on PD0332991 and those that did not was the level of MDM2 in cells following drug treatment. To determine the mechanism by which PD0332991 affected MDM2 expression, we next looked at the accumulation of MDM2 transcripts. There was no association between MDM2 mRNA expression and whether cells were responders or non-responders (FIG. 18C). We next measured MDM2 protein turnover in PD0332991 treated and serum starved responder and non-responder cells. MDM2 protein half-life was markedly reduced upon PD0332991 treatment in responder cells compared to the non-responder cells (FIGS. 18D and E). Serum starvation did not accelerate turnover to the same extent. Thus, post-translational mechanisms contribute to the turnover in responder cells treated with PD0332991.

To determine how MDM2 contributed to the growth of the WD/DDLS cell lines, we treated two responders (LS8817 and LS0082) and two non-responders (LS8107 and LS7785-1) with nutlin-3a. Nutlin-3a is expected to increase the steady state level of p53 and/or the transcriptional activity of p53 by blocking the physical interaction between p53 and MDM2. As expected, the p53 targets, MDM2 and p21, increased in all of the cell lines treated with nutlin-3a (FIG. 13B) (22). The percentage of annexin V stained apoptotic cells increased as well (FIG. 13A). Thus, nutlin-3a triggers apoptosis in both responders and non-responders.

shRNA Mediated Inhibition of MDM2 Induces Senescence.

To directly assess whether reducing MDM2 expression would induce senescence we transduced two responder (LS8817 and LS0082) and two non-responder (LS8107 and LS7785-1) cells with two lentiviruses expressing shRNAs that targeted different regions of the transcript or a scrambled control (FIG. 4A). The amount of p53 did not increase when MDM2 was reduced with two independent lentiviruses expressing shRNAs that targeted different regions of the MDM2 transcript (FIG. 4A). RB phosphorylation was reduced in all the cell lines indicative of growth arrest (FIG. 4A). p53 and ARF levels were unchanged, and p16 levels remained high (FIG. 4A). Consistent with the ability of MDM2 to block the transcriptional activity of p53 there was an increase in p21 in both responders and non-responders; however, these cells did not undergo apoptosis (data not shown). Surprisingly, both SA-β-gal (FIG. 4B) and SAHF (FIG. 4C) accumulated in responder and non-responder cells in which MDM2 had been reduced, indicating that they underwent senescence. SAHF increased in all of the cells except LS7785-1, which is consistent with the reports that not all senescent cells have the ability to form such foci (52, 53).

To ensure that senescence was not an off-target effect of the shRNA, we expressed a non-targetable 'wobbled' allele of MDM2 in LS8817 and looked at the effect on BrdU incorporation and the appearance of SA-β-gal after shRNA transduction. The shRNA directed against MDM2 was unable to reduce the expression of MDM2 in these cells (FIG. 4D) or induce senescence (FIG. 4E). Thus, we concluded that non-responder cells have the capacity to activate a senescence program but something was blocking its activation when PD0332991 induced growth arrest in these cells. Additionally, reducing MDM2 was sufficient to induce growth arrest and senescence in WD/DDLS cell lines characterized by CDK4 and MDM2 amplification.

We next asked whether the loss of MDM2 was necessary for CDK4 inhibition to induce senescence. To address this, we enforced the expression of a wild type MDM2 from a lentiviral vector and measured its effect on PD0332991-induced senescence in LS8817 cells. As a control we also expressed RFP. After transductants were selected for five days, they were treated with PD03329991. Ectopic expression of MDM2 prevented the PD0332991 induced reduction of MDM2 protein (FIG. 17). Cell cycle exit was not affected as phosphorylated Rb and cyclin A and BrdU incorporation were all reduced (FIG. 17). Arf and p16 levels did not increase, but p53 levels were still reduced (FIG. 17), indicating that PD0332991 regulated p53 accumulation in these cells independently of its effect on MDM2. Nevertheless, SA-β-gal failed to accumulate in the cells with enforced MDM2 expression (FIG. 19A). The partial response observed at higher concentrations of the drug reflects the cellular heterogeneity of MDM2 expression levels in the pool of transductants (FIG. 5D). Interestingly, ectopic expression of MDM2 unveiled the steepness of the response, suggesting that senescence was a cooperative event likely involving feedback loops whose initiation was modulated by the expression of MDM2 and reinforces the notion that it is the change in MDM2, rather than the absolute level of MDM2, that is critical in driving the cells into a senescent state. Thus we concluded that continued elevated MDM2 expression in the quiescent cell could interfere with the activation of a senescence program.

Our data indicated that reducing the level of MDM2 was necessary for senescence following PD0332991-induced growth arrest. It was not the level of MDM2 before or after drug treatment that determined response, rather it was the change in MDM2 induced by the drug that was associated with senescence. This observed change is not related to the fact that these cells overexpress different amounts of MDM2.

TABLE 1

Effect of PD0332991 on the expression of MDM2 and the accumulation of senescence-associated β-galactosidase activity in glioma and breast cancer cell lines

| Cell Line | PD-induced growth arrest[3] | PD-induced SA-β-gal[4] | ΔMDM2 with PD[5] |
|---|---|---|---|
| DKMG[1] | + | Y | 0.66 |
| SNB19[1] | + | Y | 0.08 |

TABLE 1-continued

Effect of PD0332991 on the expression of MDM2 and the accumulation of senescence-associated β-galactosidase activity in glioma and breast cancer cell lines

| Cell Line | PD-induced growth arrest[3] | PD-induced SA-β-gal[4] | ΔMDM2 with PD[5] |
|---|---|---|---|
| DBTRG-05MG[1] | + | Y | 0.49 |
| T98G[1] | + | N | Not detected |
| MCF7[2] | + | Y | 0.08 |

[1]Glioma cells
[2]Breast cancer cells
[3]BrdU incorporation is reduced at least 8X 7 days after treatment with the drug
[4]Y, yes: the number of SA-β-gal cells increases at least 10X after 7 days of treatment
[5]The ratio of MDM2 detected by Image J scanning in treated versus untreated cultures PD0332991-Induced Changes in MDM2 Protein Expression are Correlated to Patient Outcome.

As part of our recent phase II study (NCT01209598) examining the response of approximately 40 patients to PD0332991, nine consented to pre- and post-treatment biopsies allowing us to assess whether changes in MDM2 were associated with clinical outcome. These patients were RS-positive by IHC and CDK4 amplified by FISH. These patients were treated with 125 mg of PD0332991 daily for 21 days followed by seven days of rest with cycles repeating every four weeks. Pre-treatment biopsies were taken before the first dose of the drug, and a post-treatment biopsy was collected either the day before the second cycle (patients 2, 6, 8, and 9) or within six days of the start of the second cycle (patients 1, 3, 4, 5, and 7). Tumor response was assessed by CT scans every six weeks for 36 weeks and every 12 weeks thereafter. Patients were grouped by their response to the drug according to RECIST criteria (51).

Patients were grouped by their best response to the drug according to Response Evaluation Criteria in Solid Tumors (RECIST) criteria. Thus, the growth of target tumor lesions was unaffected in patients with progression of disease (POD; worsen), and halted or reduced in patients with stable disease (SD; remain the same) or partial response (PR; improve) (FIG. 7). MDM2 levels were reduced in patients 1, 4, 7, and 8 and unaffected in patients 2, 3, and 9. We were unable to detect MDM2 or RB in extracts from patient 6, although the patient was immunohistochemically positive before the start of the trial. Because we could not use GAPDH to normalize MDM2 levels in the extracts from patient 5, actin was used instead. Using the RECIST criteria previously described (51), five patients performed well on the drug. As of March 2013, one of these patients (patient 1) achieved a RECIST response as tumor size decreased greater than 60%. Two patients with progressive disease died (patients 2 and 3) and two more withdrew from the study (patients 6 and 9) due to increasing tumor burden. Changes in MDM2 were only observed in association with a favorable response (stable disease or partial response) to PD0332991. Therefore, changes in MDM2 were associated with a favorable response to PD0332991.

PD0332991 Triggers the Dissociation of HAUSP from MDM2.

We next asked how PD0332991 reduced MDM2 expression. MDM2 transcripts were modestly reduced in each cell line by PD0332991 (FIG. 18C); however, MDM2 stability was markedly reduced upon PD0332991 treatment in LS0082, LS141, and LS8817 responder cells and largely unaffected in the LS7785-1 and LS7785-10 non-responder cells (FIG. 18D). Addition of the proteasome inhibitor MG132 to PD0332991 treated LS8817 and LS141 cells allowed the re-accumulation of MDM2 (FIG. 21A). We did not look at the effect on LS0082 cells. Thus, PD0332991 triggers a post-translational proteasome-dependent mechanism that reduces MDM2 in responder cells.

Post-translational regulation of MDM2 is complex with both RING-dependent autoubiquitination and RING-independent trans-ubiquitination reactions playing a role (61, 62). The C464A mutant of MDM2 can be ubiquitinated in trans by both SCFβTrCP and PCAF, but cannot be autoubiquitinated (61-63). Thus, to ask whether autoubiquitination contributed to MDM2 turnover, we transfected LS8817 responder cells with either Flag-tagged MDM2 (F-MDM2) or the Flag-tagged E3 ligase-deficient C464A mutant and measured the stability of the proteins when PD0332991 was added. PD0332991 did not affect the stability of the C464A mutant, but the wild type protein was still turned over (FIG. 21B). Thus the PD0332991 induced turnover of MDM2 was dependent on autoubiquitination.

Figure 25A:
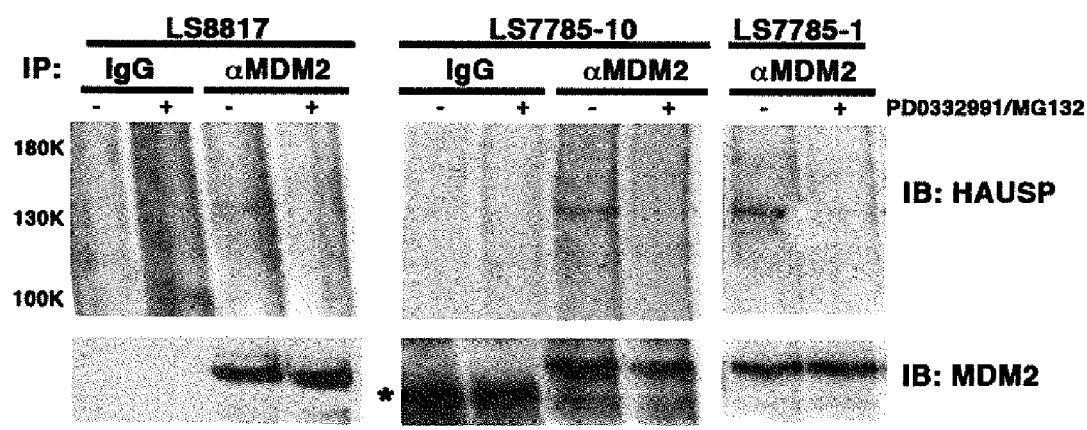
Figure 25B:
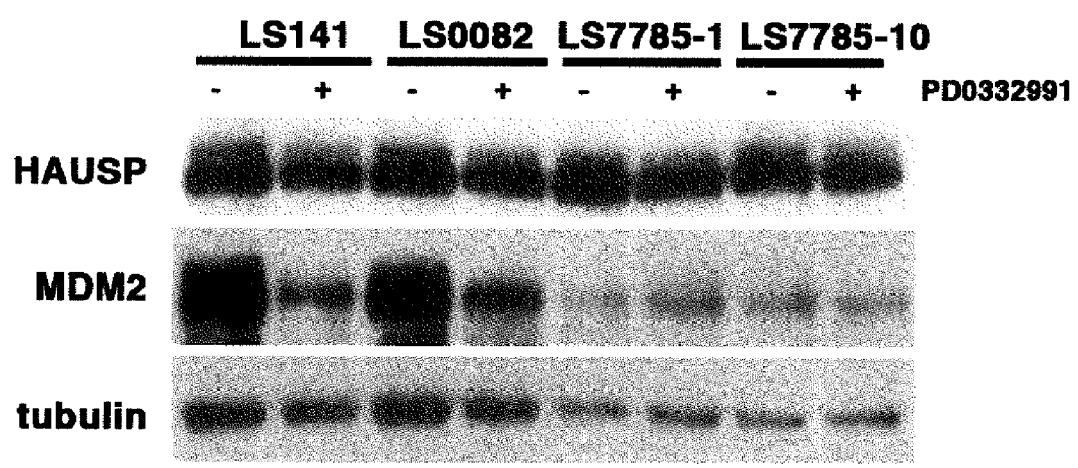
Figure 25C:
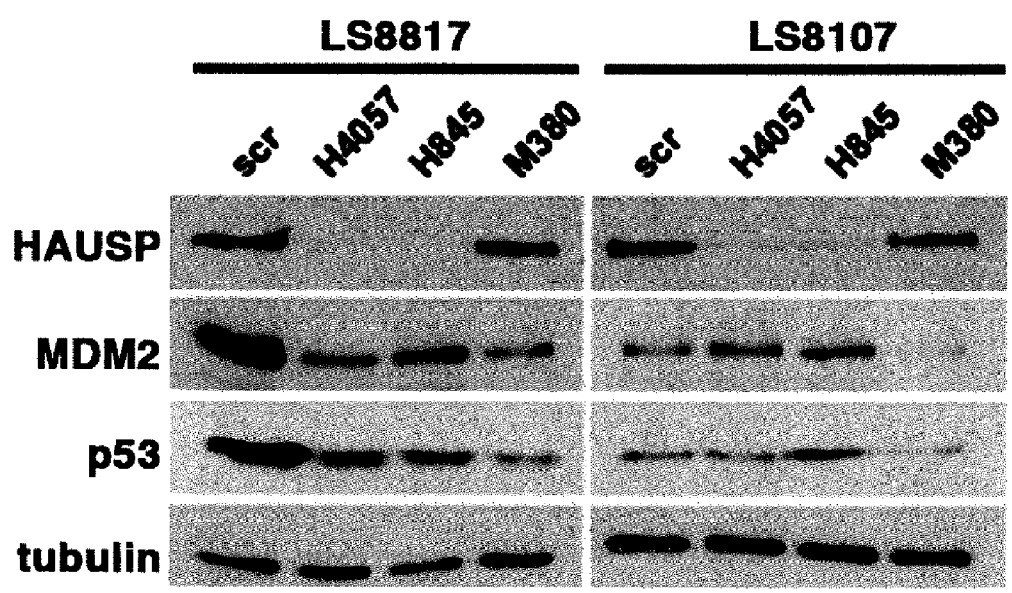

The interaction of MDM2 with the deubiquitinase HAUSP/USP7 is key to inhibiting MDM2 turnover (59, 60). Thus, we asked if differences in the interaction of HAUSP and MDM2 might contribute to the differential stability observed in responder and non-responder cells. We detected the interaction of HAUSP and MDM2 by co-immunoprecipitation in untreated asynchronously growing LS8817 and LS0082 (responder) and LS7785-1 and LS7785-10 (non-responder) cells, but not in any of the cells treated with PD0332991 (FIG. 25A). We did not look at this interaction in LS141, LS8813 and LS8107 cells. HAUSP levels did not change following PD0332991 treatment (FIG. 25B). Thus inhibiting CDK4 induced the dissociation of MDM2 and HAUSP regardless of whether the cell was a responder or a non-responder.

Figure 25D:
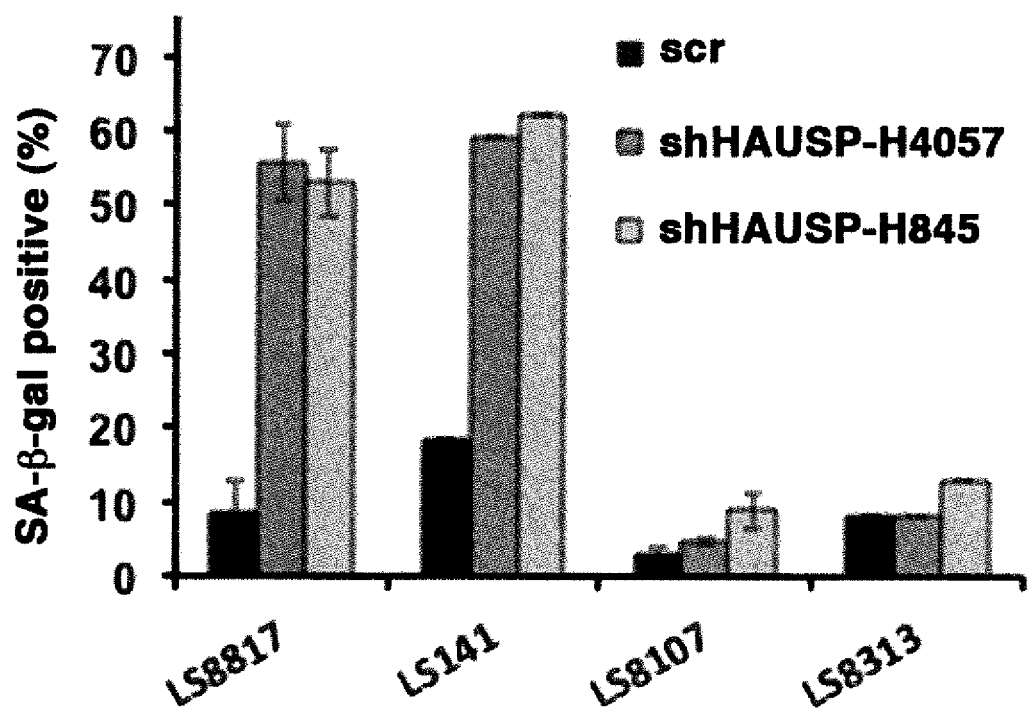

The data above suggested that some activity in non-responder cells was either missing or prevented MDM2 turnover by this mechanism. Consistent with this, knocking down HAUSP with two independent lentiviral hairpins in the non-responder LS8107 did not reduce MDM2 levels (FIG. 25C) and the number of SA-β-gal positive cells did not increase (FIG. 25D). These cells still underwent growth arrest (data not shown). Reducing HAUSP in LS8817 cells was sufficient to induce arrest (data not shown), reduce the level of MDM2 (FIG. 25C), and SA-β-gal positive cells accumulated (FIG. 25D). Taken together, these data indicate that CDK4 inhibitors promote the dissociation of HAUSP from MDM2; however, a subsequent cell-type specific step is required for MDM2 turnover.

6.3 Discussion

WD/DDLS is one of the most common types of soft tissue sarcomas and is difficult to treat when surgical resection is not possible since they are relatively resistant to conventional chemotherapy. Ninety percent (90%) of WD/DDLS have amplification of genes on chromosome segment 12q13-15, associated with overexpression of the oncogenes MDM2 and CDK4. This region contains two distinct 12q amplicons, one that carries the oncogene MDM2 and a second, which carries CDK4 (29). The highly recurrent nature of these amplifications suggests that a greater understanding of the dysregulated signaling pathways driven by MDM2 and CDK4 could lead to the development of more efficacious treatment strategies in WD/DDLS.

In this working example, we demonstrate that inhibiting CDK4 activity in WD/DDLS leads to growth arrest in all cell lines, and induces senescence in a subset. Induction of senescence is associated with decreases in the level of MDM2 but not alterations in expression of p16, ARF, or p53, canonical regulators of the senescent phenotype. Senescence is induced when MDM2 is inhibited by shRNA knockdown in all the cultured cells, suggesting that the continued elevation of MDM2 is preventing senescence in quiescent cells. In fact, enforced expression of MDM2 inhibits PD-induced senescence but not its ability to induce growth arrest.

Senescence is a common early barrier to oncogenesis (28, 30, 31). Our results suggest that co-amplification of MDM2 and CDK4 has the effect of abrogating this response. We propose that during the initiation of this disease, an as of yet unidentified oncogene confers the propensity of cells to senesce. Amplification of MDM2 on 12q13-15 plays a role preventing this. However, amplification is not sufficient to upregulate the amount of MDM2 in the cell, and co-amplification of CDK4 is required to increase MDM2 expression and inhibit cellular senescence. CDK4-dependent upregulation of MDM2 may explain why these two genes are frequently co-amplified, and senescence may explain why those tumors with amplification of MDM2 but not CDK4 typically have a benign clinical course (29).

While providing insight into the roles that MDM2 and CDK4 play in liposarcomagenesis, this work also provides insight into how CDK4 inhibition may have clinical benefit in vivo. In a phase I study of the CDK4/6 inhibitor PD0332991, two patients with RB-positive WD/DDLS had prolonged stable disease lasting several years (32). Findings of a phase II trial examining the safety and efficacy of the CDK4/6 inhibitor PD0332991 in 30 WD/DDLS patients have been reported (51). Results from this trial show prolonged stable disease in 66% of the patients. One patient achieved a RECIST partial response at 74 weeks. Three other patients had evidence of favorable response to treatment that did not meet RECIST, specifically, decrease in tumor size of at least 10%. Treatment with PD0332991 was generally well-tolerated, although myelosuppression was common. Only a minority of patients required dose reductions or dose delays. Our data indicate that the difference in PD0332991-induced response, vis a vis senescence or growth arrest, may underlie the variation in patient response. Senescence has been proposed to be a favorable clinical endpoint (28) and our data indicates that changes in MDM2 correlate with patient response to the drug.

Additional correlative studies involving more WD/DDLS patients, and in other diseases where PD0332991 has had success, need to be carried out to see how universal this relationship might be. The data obtained from our phase II clinical trial shows that reduced MDM2 levels upon CDK4 treatment are associated with better outcomes. This is consistent with the notion that senescence is a preferred clinical outcome and paves the way to directly assess this hypothesis in our future phase III studies to be initiated shortly. Thus, we show that the down-regulation of MDM2 triggered by CDK4 inhibition triggers a novel p53-independent pathway that can contribute to senescence, both in cells in which MDM2 is amplified and the protein overexpressed and those in which MDM2 is not amplified nor over expressed.

6.4. References

1. Jackman D M, Miller V A, Cioffredi L A, et al. Impact of epidermal growth factor receptor and KRAS mutations on clinical outcomes in previously untreated non-small cell lung cancer patients: results of an online tumor registry of clinical trials. Clinical cancer research: an official journal of the American Association for Cancer Research 2009; 15: 5267-73.
2. Janku F, Tsimberidou A M, Garrido-Laguna I, et al. PIK3CA mutations in patients with advanced cancers treated with PI3K/AKT/mTOR axis inhibitors. Molecular cancer therapeutics 2011; 10: 558-65.
3. Khambata-Ford S, Garrett C R, Meropol N J, et al. Expression of epiregulin and amphiregulin and K-ras mutation status predict disease control in metastatic colorectal cancer patients treated with cetuximab. Journal of clinical oncology: official journal of the American Society of Clinical Oncology 2007; 25: 3230-7.
4. Loupakis F, Ruzzo A, Cremolini C, et al. KRAS codon 61, 146 and BRAF mutations predict resistance to cetuximab plus irinotecan in KRAS codon 12 and 13 wild-type metastatic colorectal cancer. British journal of cancer 2009; 101: 715-21.
5. Van Cutsem E, Kohne C H, Hitre E, et al. Cetuximab and chemotherapy as initial treatment for metastatic colorectal cancer. The New England journal of medicine 2009; 360: 1408-17.
6. Barretina J, Taylor B S, Banerji S, et al. Subtype-specific genomic alterations define new targets for soft-tissue sarcoma therapy. Nature genetics 2010; 42: 715-21.
7. Malumbres M, Barbacid M. Cell cycle, CDKs and cancer: a changing paradigm. Nature reviews Cancer 2009; 9: 153-66.
8. Ringshausen I, O'Shea C C, Finch A J, Swigart L B, Evan G L Mdm2 is critically and continuously required to suppress lethal p53 activity in vivo. Cancer cell 2006; 10: 501-14.
9. McDuff F K, Turner S D. Jailbreak: oncogene-induced senescence and its evasion. Cellular signalling 2011; 23: 6-13.
10. Sperka T, Wang J, Rudolph K L. DNA damage checkpoints in stem cells, ageing and cancer. Nature reviews Molecular cell biology 2012; 13: 579-90.
11. Secchiero P, Bosco R, Celeghini C, Zauli G. Recent advances in the therapeutic perspectives of Nutlin-3. Current pharmaceutical design 2011; 17: 569-77.
12. Cheok C F, Verma C S, Baselga J, Lane D P. Translating p53 into the clinic. Nature reviews Clinical oncology 2011; 8: 25-37.
13. Korotchkina L G, Leontieva O V, Bukreeva E I, Demidenko Z N, Gudkov A V, Blagosklonny M V. The choice between p53-induced senescence and quiescence is determined in part by the mTOR pathway. Aging 2010; 2: 344-52.
14. Fry D W, Harvey P J, Keller P R, et al. Specific inhibition of cyclin-dependent kinase 4/6 by PD 0332991 and associated antitumor activity in human tumor xenografts. Molecular cancer therapeutics 2004; 3: 1427-38.
15. Roberts P J, Bisi J E, Strum J C, et al. Multiple roles of cyclin-dependent kinase 4/6 inhibitors in cancer therapy. Journal of the National Cancer Institute 2012; 104: 476-87.
16. Johnson S M, Torrice C D, Bell J F, et al. Mitigation of hematologic radiation toxicity in mice through pharmacological quiescence induced by CDK4/6 inhibition. The Journal of clinical investigation 2010; 120: 2528-36.
17. Michaud K, Solomon D A, Oermann E, et al. Pharmacologic inhibition of cyclin-dependent kinases 4 and 6 arrests the growth of glioblastoma multiforme intracranial xenografts. Cancer research 2010; 70: 3228-38.
18. Wiedemeyer W R, Dunn I F, Quayle S N, et al. Pattern of retinoblastoma pathway inactivation dictates response to CDK4/6 inhibition in GBM. Proceedings of the National Academy of Sciences of the United States of America 2010; 107: 11501-6.
19. Serrano M, Lin A W, McCurrach M E, Beach D, Lowe S W. Oncogenic ras provokes premature cell senescence associated with accumulation of p53 and p16INK4a. Cell 1997; 88: 593-602.
20. Narita M, Nunez S, Heard E, et al. Rb-mediated heterochromatin formation and silencing of E2F target genes during cellular senescence. Cell 2003; 113: 703-16.
21. Halvorsen Y D, Bond A, Sen A, et al. Thiazolidinediones and glucocorticoids synergistically induce differentiation of human adipose tissue stromal cells: biochemical, cellular, and molecular analysis. Metabolism: clinical and experimental 2001; 50: 407-13.
22. Singer S, Socci N D, Ambrosini G, et al. Gene expression profiling of liposarcoma identifies distinct biological types/subtypes and potential therapeutic targets in well-differentiated and dedifferentiated liposarcoma. Cancer research 2007; 67: 6626-36.
23. Chan C H, Gao Y, Moten A, Lin H K. Novel ARF/p53-independent senescence pathways in cancer repression. J Mol Med (Berl) 2011; 89: 857-67.
24. Hsieh J K, Chan F S, O'Connor D J, Mittnacht S, Zhong S, Lu X. RB regulates the stability and the apoptotic function of p53 via MDM2. Molecular cell 1999; 3: 181-93.
25. Xiao Z X, Chen J, Levine A J, et al. Interaction between the retinoblastoma protein and the oncoprotein MDM2. Nature 1995; 375: 694-8.
26. Yap D B, Hsieh J K, Chan F S, Lu X. mdm2: a bridge over the two tumour suppressors, p53 and Rb. Oncogene 1999; 18: 7681-9.
27. Knudsen E S, Buckmaster C, Chen T T, Feramisco J R, Wang J Y. Inhibition of DNA synthesis by RB: effects on G1/S transition and S-phase progression. Genes & development 1998; 12: 2278-92.
28. Collado M, Serrano M. Senescence in tumours: evidence from mice and humans. Nature reviews Cancer 2010; 10: 51-7.
29. Italiano A, Bianchini L, Gjernes E, et al. Clinical and biological significance of CDK4 amplification in well-differentiated and dedifferentiated liposarcomas. Clinical cancer research: an official journal of the American Association for Cancer Research 2009; 15: 5696-703.
30. Campisi J. Cellular senescence: putting the paradoxes in perspective. Current opinion in genetics & development 2011; 21: 107-12.
31. Narita M, Lowe S W. Senescence comes of age. Nature medicine 2005; 11: 920-2.
32. Schwartz G K, LoRusso P M, Dickson M A, et al. Phase 1 study of PD 0332991, a cyclin-dependent kinase inhibitor, administered in 3-week cycles (Schedule 2/1). British journal of cancer 2011; 104: 1862-8.
33. Goentoro L, Kirschner M W. Evidence that fold-change, and not absolute level, of beta-catenin dictates Wnt signaling. Molecular cell 2009; 36: 872-84.
34. Campisi J. The biology of replicative senescence. Eur J Cancer 1997; 33: 703-9.
35. Courtois-Cox S, Jones S L, Cichowski K. Many roads lead to oncogene-induced senescence. Oncogene 2008; 27: 2801-9.
36. Prieur A, Besnard E, Babied A, Lemaitre J M. p53 and p16(INK4A) independent induction of senescence by chromatin-dependent alteration of S-phase progression. Nature communications 2011; 2: 473.
37. Ramsey M R, Sharpless N E. ROS as a tumour suppressor? Nature cell biology 2006; 8: 1213-5.
38. Kuilman T, Peeper D S. Senescence-messaging secretome: SMS-ing cellular stress. Nature reviews Cancer 2009; 9: 81-94.
39. Chicas A, Wang X, Zhang C, et al. Dissecting the unique role of the retinoblastoma tumor suppressor during cellular senescence. Cancer cell 2010; 17: 376-87.
40. Kuilman T, Michaloglou C, Mooi W J, Peeper D S. The essence of senescence. Genes & development 2010; 24: 2463-79.
41. Rodier F, Campisi J. Four faces of cellular senescence. The Journal of cell biology 2011; 192: 547-56.
42. Capparelli C, Chiavarina B, Whitaker-Menezes D, et al. CDK inhibitors (p16/p19/p21) induce senescence and autophagy in cancer-associated fibroblasts, "fueling" tumor growth via paracrine interactions, without an increase in neo-angiogenesis. Cell Cycle 2012; 11: 3599-610.
43. Puyol M, Martin A, Dubus P, et al. A synthetic lethal interaction between K-Ras oncogenes and Cdk4 unveils a therapeutic strategy for non-small cell lung carcinoma. Cancer cell 2010; 18: 63-73.
44. Rane S G, Cosenza S C, Mettus R V, Reddy E P. Germ line transmission of the Cdk4(R24C) mutation facilitates tumorigenesis and escape from cellular senescence. Molecular and cellular biology 2002; 22: 644-56.
45. Adams P D. Healing and hurting: molecular mechanisms, functions, and pathologies of cellular senescence. Molecular cell 2009; 36: 2-14.
46. Anders L, Ke N, Hydbring P, et al. A systematic screen for CDK4/6 substrates links FOXM1 phosphorylation to senescence suppression in cancer cells. Cancer cell 2011; 20: 620-34.
47. Taylor B S, Barretina J, Socci N D, et al. Functional copy-number alterations in cancer. PloS one 2008; 3: e3179.
48. Zezula J, Casaccia-Bonnefil P, Ezhevsky S A, et al. p21cip1 is required for the differentiation of oligodendrocytes independently of cell cycle withdrawal. EMBO reports 2001; 2: 27-34.
49. Ciznadija D, Zhu X H, Koff A. Hdm2- and proteasome-dependent turnover limits p21 accumulation during S phase. Cell Cycle 2011; 10: 2714-23.
50. Iwakuma T and Lozano G. MDM2, An Introduction. Mol. Cancer Research 2003; 1: 993-1000.
51. Dickson M A, Tap, W D, Keohan M L, et al. Phase H Trial of the CDK4 Inhibitor PD0332991 in Patients With Advanced CDK4-Amplified Well-Differentiated or Dedifferentiated Liposarcoma. J. Clin. Oncol. 2013; 31(16): 2024-8.
52. Kosar, M., Bartkova, J., Hubackova, S., Hodny, Z., Lukas, J., and Bartek, J. (2011). Senescence-associated heterochromatin foci are dispensable for cellular senescence, occur in a cell type- and insult-dependent manner and follow expression of p16(ink4a). Cell Cycle 10, 457-468.
53. Lawless, C., Wang, C., Jurk, D., Merz, A., Zglinicki, T., and Passos, J. F. (2010). Quantitative assessment of markers for cell senescence. Exp Gerontol 45, 772-778.
54. Coppe, J. P., Desprez, P. Y., Krtolica, A., and Campisi, J. (2010). The senescence-associated secretory phenotype: the dark side of tumor suppression. Annu Rev Pathol 5, 99-118.

55. Davalos, A. R., Coppe, J. P., Campisi, J., and Desprez, P. Y. (2010). Senescent cells as a source of inflammatory factors for tumor progression. Cancer Metastasis Rev 29, 273-283.

56. Lujambio, A., Akkari, L., Simon, J., Grace, D., Tscharganeh, D. F., Bolden, J. E., Zhao, Z., Thapar, V., Joyce, J. A., Krizhanovsky, V., and Lowe, S. W. (2013). Non-cell-autonomous tumor suppression by p53. Cell 153, 449-460.

57. Tchkonia, T., Zhu, Y., van Deursen, J., Campisi, J., and Kirkland, J. L. (2013). Cellular senescence and the senescent secretory phenotype: therapeutic opportunities. The Journal of clinical investigation 123, 966-972.

58. Aksoy, O., Chicas, A., Zeng, T., Zhao, Z., McCurrach, M., Wang, X., and Lowe, S. W. (2012). The atypical E2F family member E2F7 couples the p53 and RB pathways during cellular senescence. Genes & development 26, 1546-1557.

59. Brooks, C. L., Li, M., Hu, M., Shi, Y., and Gu, W. (2007). The p53-Mdm2-HAUSP complex is involved in p53 stabilization by HAUSP. Oncogene 26, 7262-7266.

60. Li, M., Brooks, C. L., Kon, N., and Gu, W. (2004). A dynamic role of HAUSP in the p53-Mdm2 pathway. Molecular cell 13, 879-886.

61. Inuzuka, H., Tseng, A., Gao, D., Zhai, B., Zhang, Q., Shaik, S., Wan, L., Ang, X. L., Mock, C., Yin, H., et al. (2010). Phosphorylation by casein kinase I promotes the turnover of the Mdm2 oncoprotein via the SCF(beta-TRCP) ubiquitin ligase. Cancer cell 18, 147-159.

62. Jung, C. R., Lim, J. H., Choi, Y., Kim, D. G., Kang, K. J., Noh, S. M., and Im, D. S. (2010). Enigma negatively regulates p53 through MDM2 and promotes tumor cell survival in mice. The Journal of clinical investigation 120, 4493-4506. Knudsen, E. S., Buckmaster, C., Chen, T. T., Feramisco, J. R., and Wang, J. Y.

63. Linares, L. K., Kiernan, R., Triboulet, R., Chable-Bessia, C., Latreille, D., Cuvier, O., Lacroix, M., Le Cam, L., Coux, O., and Benkirane, M. (2007). Intrinsic ubiquitination activity of PCAF controls the stability of the oncoprotein Hdm2. Nature cell biology 9, 331-338.

7. EXAMPLE 2: SENESCENCE INDUCED BY CDK4 INHIBITION MODULATES RB PHOSPHORYLATION

7.1 Materials and Methods

Cell Line Culture, Differentiation and Validation.

Cell lines were developed from WD/DDLS tumors resected from surgical patients after obtaining informed consent. LS8817 and LS0082 have previously been described using the nomenclature DDLS8817 and WD0082. DNA was extracted from cell lines using standard protocols (QIAGEN DNEasy) and lineage confirmed by copy number array to confirm amplification of segment 12q13-15 (Agilent 244K according to manufacturer's specifications). Analysis of comparative genomic hybridization data was performed using a custom pipeline, which conducts the standard circular binary segmentation from the R/bioconductor DNA-copy library and processes all samples with the RAE algorithm (Taylor et al., 2008).

Cell lines were maintained in DME HG supplemented with 10% heat-inactivated fetal bovine serum and 2 mM L-glutamine. RNA was extracted from cells (RNEasy, QIAGEN) and reverse transcription performed (Singer et al., 2007) after treatment for 7 days with PD0332991 (Selleckchem) or differentiation media as previously described (Halvorsen et al., 2001).

Cell Cycle Analyses.

shRNA were delivered in the pLKO.1 vector (Sigma) and infected cells selected using puromycin (1 µg/ml); infection with a virus carrying a scramble control (CAACAAGAT-GAAGAGCACCAA) was used as a control in all experiments utilizing shRNA. Cell lines were treated with PD0339221 or shRNA directed against CDK4 (GAGAT-TACTTTGCTGCCTTAA (SEQ ID NO:4)), MDM2 (M376, TTCACTATTCCACTACCAAAG (SEQ ID NO:5); M380, TACTAGAAGTTGATGGCTGAG (SEQ ID NO:6)), HAUSP (4057, CCAGCTAAGTATCAAAGGAAA (SEQ ID NO:7); 845, CGTGGTGTCAAGGTGTACTAA (SEQ ID NO:8)) or CDK6 (GACCTGGAAAGGTGCAAAGAA (SEQ ID NO:9)) for 48 hours to 7 days and stained with BrdU (20 µM for two hours) or annexin V as previously described (Singer et al., 2007; Zezula et al., 2001). G0 content was determined by staining with propidium iodine and FACS analyses (Ciznadija et al., 2011).

For MDM2 and Rb expression, cells were infected with a lentivirus (pLOC, Open Biosystems) encoding either MDM2, MDM2 V75A, MDM2 I440A, MDM2 C464A, MDM2 Δ254-264, MDM2 L468A, MDM2 Δ464-471, MDM2 P476A, RB, LP-RB, PSM-RB or RFP. Transduced cells were selected for in media containing 3 µg/ml blasticidin and selection was maintained throughout the experiment.

Senescence Analyses.

Cells were plated at a concentration of 25,000 per well in a 4-well chamber slides (Lab-Tek) and treated for seven days with drug and stained for senescence-associated β-galactosidase (Cell Signaling kit #9860). Cell number was quantitated by DAPI staining and β-galactosidase staining quantitated as a proportion of total cells.

Senescence associated heterochromatic foci were quantitated after cells were fixed with 4% paraformaldehyde, permeabilized with 0.1% Triton, blocked with 2% FBS, and stained with antibodies against HP1γ (1:5000 dilution, 2MOD-1G6 Millipore). Senescent cells were identified by immunofluorescence after treatment of slides with anti-mouse secondary antibodies and quantitation of focal SAHF as a percent of total cells (Leica Upright Confocal SP5 confocal microscope).

Immunoblot.

Antibodies against CDK4 (3F121), MDM2 (SMP-14), total RB (IFS), Cyclin A (H432), p16 (C20), and p53 (Bp53-12), were obtained from Santa Cruz Biotechnology, phospho-Rb 780 (#9307) from Cell Signalling, and ARF (3642) from Abcam. Treated cells were lysed with buffer composed of 50 mM Tris-HCl, pH7.4, 250 mM NaCl, 5 mM EDTA, 0.5% NP40, 2 mM PMSF, and supplemented with protease inhibitors. Eighty micrograms of protein were resolved by SDS-PAGE and transferred to PVDF membranes. Membranes were incubated overnight with antibodies (1:1000).

Extracts were prepared from pre-treatment biopsies within a period of two weeks before the first dose of the drug and post-treatment biopsies within 7-10 days after three weeks of treatment. Extracts were prepared in 50 mM Tris-HCl, pH7.4, 150 mM NaCl, 1 mM EDTA, 1% NP40, 0.25% sodium deoxycholate and supplemented with mini-protease inhibitor cocktail (Roche). Tumor response was assessed by reference radiologist by CT scan every six weeks for 36 weeks, and every 12 weeks thereafter. The clinical trial was approved by the Institutional Review Board of Memorial Sloan-Kettering Cancer Center and all patients provided written informed consent (NCT01209598).

Wobble Rescue.

Cells were first infected with a lentivirus (pLOC, Open Biosystems) encoding either an MDM2 expression cassette containing the mismatched sequence (ACTATTCTCAAC-CCTCAACTTCTA (SEQ ID NO:10)) or RFP cassette. 24 hours later, transduced cells were selected for in media containing 3 μg/ml blasticidin and selection was maintained throughout the experiment. Five days after blasticidin selection began, we transduced the cells with a second lentiviral vector encoding either the shM380 sequence targeting MDM2 or a scrambled sequence (shSCR) as described above. 24 hours later these cells were selected in media containing both blasticidin and 3 mg/ml puromycin.

7.2 Results

Senescence Induced by PD0332991 is p53 and INK4A Independent.

MDM2 is best known as a negative regulator of p53, affecting both its transcriptional activity and catalyzing its ubiquitination and turnover (Haupt et al., 1997; Honda et al., 1997; Kubbutat et al., 1997; Momand et al., 1992; Oliner et al., 1993). Therefore, we looked at the effect of PD0332991, CDK4 knockdown, expression of PSM-Rb, MDM2 knockdown, and CDK6 knockdown on p53 accumulation. Remarkably, p53 levels were decreased by PD0332991 treatment (FIG. 2D), and in cells in which CDK4 was reduced by knock down (FIG. 3A), regardless of whether they were responders or nonresponders. We could not detect any increase in p53 when we assessed protein accumulation and localization with a number of different extraction conditions and a number of different antibodies for blotting (for example, extracts were prepared in SDS-RIPA buffers for FIG. 22). On the other hand, p53 levels were not reduced in the MDM2 knockdown (FIG. 4A) or in cells expressing PSM-Rb (FIG. 6B), or in cells in which CDK6 was knocked down (FIG. 12A). There are multiple pathways by which cells can become senescent, some of which are p53-dependent and others that are p53-independent (Campisi, 1997; Courtois-Cox et al., 2008; Kuilman et al., 2010; Lin et al., 2010; Prieur et al., 2011; Ramsey and Sharpless, 2006). However, because it was so surprising that pathways involving MDM2 might be p53-independent, we investigated this further.

To determine if p53 was important for senescence induced by either PD0332991 or MDM2 knockdown in LS8817 cells, we reduced the level of p53 with two independent shRNAs in these cells. Although both shRNAs reduced the level of p53, one had a more pronounced effect on the steady state level of MDM2 than the other (FIG. 26). SA-β-gal positive cells still accumulated when the p53 deficient cells were treated with PD0332991 (FIG. 26) or when MDM2 was knocked down (FIG. 26). This indicates that loss of MDM2 can induce senescence in a p53-independent manner. Additionally, PD0332991 induced senescence in responder cells in which p53 was reduced by infection with lentiviral shRNA expressing vectors that reduced p53. Collectively, this suggested that MDM2 suppressed senescence in a p53-independent manner We also wanted to determine if PD0332991 induced senescence depended on the products of the INK4A locus, p16 and Arf. PD0332991 induced senescence was not affected when we knocked down these gene products.

However, a knock down could leave a small undetectable biologically active pool of p53; thus, we wanted a cleaner "genetic" test of p53 dependence. We realized that p53 mutations and INK4 loss are quite common in glioma and breast cancer (Dean et al., 2012; Michaud et al., 2010; Roberts et al., 2012; Thangavel et al., 2011). Thus, we collected eight cell lines, some of which were mutant at the p53 and/or the INK4 locus, and all of which do not over express MDM2 and asked whether they underwent senescence when treated with PD0332991 as indicated, by loss of cyclin A and/or a reduction in RB phosphorylation (FIG. 19B). Total RB expression is also reduced in many of the arrested cells but we did not pursue this. Consistent with the reported mutational status of p53, we could detect p21 in U87MG, DBTRG-05MG, ZR-75-1, and MCF7 cells but not in U251, SNB19 and MDA453 cells (FIG. 19B). T47D, reported to have an L194F mutation in p53, still expressed p21. All of the cell lines underwent senescence as measured by accumulation of SA-β-gal (FIG. 19B). Similar to our observations in the WD/DDLS responder cell lines, MDM2 levels decreased following PD0332991 treatment (FIG. 19B). Thus, PD0332991-induced loss of MDM2 and senescence is also seen in breast cancer and glioma cell lines. While the WD/DDLS cell lines all had amplification and over-expression of MDM2, these breast and glioma cell lines do not; thus, indicating that CDK4 inhibition induced senescence was not dependent on high levels of MDM2. Thus, this MDM2-dependent p53- and INK4A-independent senescence pathway triggered by CDK4 inhibition operates in multiple cell types, including those in which MDM2 is not amplified. We then asked if MDM2 knockdown would also induce senescence in SNB19 and MCF7 cells, a p53 mutant glioma and a p53 wild type breast cancer. In both cases, the cells underwent senescence (FIG. 27A).

To further confirm that the p53 interaction was not required for MDM2 to prevent senescence, we compared the capacity of a V75A that disrupts p53 binding (Moll and Petrenko, 2003) and wild-type MDM2 to block PD0332991 induced senescence. We also looked at MDM2 mutations that affect its non-p53 related functions (Marine and Lozano, 2010), such as the C464A. I440A, L468A, P476A and Δ254-264 mutations. The C464A mutation disrupts the cross brace structure of the RING and eliminates E3 ligase activity (Foo et al., 2007; Wawrzynow et al., 2007), and the I440A, L468A, and P476A mutations eliminate E3 ligase activity but do so by selectively disrupting E2 binding (Mace et al., 2008). The Δ254-264 mutation in the acidic domain disrupts multiple MDM2 protein interactions (Sdek et al., 2004). As a control, we also expressed red fluorescent protein (RFP).

The V75A mutant was capable of suppressing the PD0332991 induced accumulation of SA-β-gal positive cells (FIG. 19A), therefore, reinforcing the notion that PD0332991 induced senescence was p53-independent. None of the four RING mutants examined were able to suppress the PD0332991 induced accumulation of SA-β-gal positive cells. Additionally, another mutant that overlaps with the RING but also affects nucleolar localization (Δ464-471) could not suppress accumulation of SA-β-gal positive cells. Collectively, this indicated that the E3 ligase activity of MDM2 was necessary for suppressing senescence and it might target a substrate that binds to the acidic domain, but it was clearly not p53-dependent. Similarly, the wild type and V75A mutant could suppress PD0332991-induced accumulation of SA-β-gal positive SNB19 cells, but the C464A mutant could not (FIG. 19C).

Reducing SKP2 induces cell cycle arrest and can trigger an INK4A and p53-independent senescence pathway in oncogenically transformed cells (Lin et al., 2010). Given that activation of the SKP2 pathway is essential for continued cell cycling it was not likely that it was a key determinant for whether a cell undergoes senescence or quiescence once it exits the cell cycle. Nevertheless, to confirm that the activity of the SKP2 complex was not different between the responder and non-responder cells we looked at the expression of p27, the best described substrate of the SKP2 ligase (Hershko, 2008; Wang et al., 2012; Zhu et al., 2004). p27 levels were identical in the responder and non-responder cells, and were unchanged by PD0332991 treatment (FIG. 22). Thus, as expected, this MDM2 repressed pathway was unrelated to the $SCF^{skp2}$ repressed pathway.

Accumulation of Unphosphorylated RB is Sufficient to Promote Senescence.

The senescence programs induced by either PD0332991 or MDM2 knockdown were not associated with accumulation of a robust transcriptionally active p53 program. In contrast, accumulation of transcriptionally active p53 led to apoptosis. Furthermore, after changing extraction conditions and using a number of different p53 antibodies for blotting and localization by immunofluorescence we ruled out that p53 modifications or localization differences could explain the apparent p53-independence of this process.

Senescence can be induced by triggering the RB pathway in the absence of p53 (Sperka et al., Nature reviews Molecular cell biology 2012; 13: 579-90; Chan et al., J Mal Med (Berl) 2011; 89: 857-67). MDM2 can interact with RB (Hsieh et al., Molecular cell 1999; 3: 181-93; Xiao et al., Nature 1995; 375: 694-8; Yap et al., Oncogene 1999; 18: 7681-9), and might prevent its ability to promote senescence. To determine whether the accumulation of unphosphorylated RB would be sufficient to induce senescence, we expressed the non-phosphorylatable large pocket mutant of RB (PSM-Rb) (Knudsen et al., 1998) in two of the responder cell lines, LS8817 and LS0082, and as a control in one of the non-responder cell lines, LS7785-1. As another control, we also expressed the wild type large pocket (LP) which could be inactivated by endogenous cyclin-dependent kinases. As expected, proliferation was significantly curtailed by expression of PSM-Rb in the three cell lines, but not by LP (FIG. 6A). MDM2 levels were reduced in the responder cell lines but not in the non-responder (FIG. 6A), and SA-βgal staining (FIG. 6B) increased only in the PSM-Rb expressing responder cell lines and not the non-responder. Phosphorylation of the endogenous RB protein, while diminished relative to control cells was still detected indicating that these growth arrested cells still had a higher level of cyclin D1-cdk4 activity than the PD0332991 treated control cells (FIGURE C and D).

We also induced G0/G1 arrest and prevented RB phosphorylation by serum starvation of two responder cell lines, LS141 and LS8817, and two non-responder cell lines, LS8107 and LS7785-10 (FIG. 18) and measured the effect on senescence. BrdU incorporation was reduced, but MDM2 was not reduced (FIG. 18A), nor did the number of SA-β-gal positive cells increase (FIG. 18B). This indicated that growth arrest was not sufficient to account for the regulation of MDM2. We did not detect any association between catalase expression (FIG. 22), a marker of the ROS pathway, or recruitment of p53BP1 to chromatin, a marker of the DNA damage response pathway with response status, indicating that unbalanced mitogenic signaling is the stress that induces this pathway.

Thus, at least, in the presence of serum the accumulation of unphosphorylated RB in responders is sufficient to reduce the accumulation of MDM2 and induce senescence to a quantitatively similar degree as PD0332991, shRNA directed against CDK4, or shRNA directed against MDM2. Without being bound to a particular theory, this data suggest there is a feedback loop between RB inactivation and MDM2 levels that could initiate and maintain cells in the senescent state, which was disrupted in the non-responder.

7.3 Discussion

Senescence is a potent barrier to tumor formation, and triggering its reactivation in tumor cells is considered a viable therapeutic option. However, our understandings of the pathways through which cells become senescent are still immature. Most triggers, such as oncogenic stress, accumulation of reactive oxygen species or DNA damage, lead to the activation of the ARF-p53 and/or p16-RB pathways, with either alone often being sufficient for cells to senesce (Campisi, 1997; Courtois-Cox et al., 2008; Kuilman et al., 2010; Ramsey and Sharpless, 2006). In common between all these pathways is that the cell makes a decision to either continue cycling or undergo senescence. On the other hand, here we report a novel pathway to senescence, one that reflects a choice between quiescence or senescence. Studying this developmentally unique pathway led us to define an equally unique molecular pathway—one induced by inhibiting CDK4 and is independent of p53 and INK4A.

We identified MDM2 as a critical player suppressing senescence in cells that exited the cell cycle in response to CDK4 inhibition. Continued MDM2 expression prevents quiescent cells from progressing to senescence, and reducing MDM2 is sufficient to trigger the senescence pathway. This pathway can be triggered in a number of cell types, including WD/DDLS in which MDM2 is amplified and over-expressed, and those in which it is not typically amplified or over-expressed such as breast cancer and glioma. This pathway is not activated by serum starvation, induction of p53 by nutlins, or DNA damage.

It is quite interesting to note that the reduction of MDM2 from cycling to non-cycling cells, rather than the absolute level of MDM2, is what triggers the senescence response. This type of signal, where the cell reads the change in the level of the protein versus its absolute level, is emerging as a systems-level concept in other signaling pathways (Goentoro et al., Molecular Cell 2009; 36: 872-84). It is proposed to buffer cellular response to transient variations in protein amount. However, the question of how cells accomplish such a measurement is still not clear. Understanding why the level of MDM2 is altered so much more in responders compared to the non-responders may illuminate our understanding of such regulatory inputs. Clearly, accumulation of unphosphorylated Rb in responder cells is necessary, but it is not sufficient because serum starvation induces arrest with hypophosphorylated RB but not senescence (unpublished data), and unphosphorylated RB alone cannot does not induce senescence in non-responder cells.

In addition to the potential clinical implications, our study also has provided significant and innovative insight into the molecular mechanisms by which CDK4 and MDM2 inhibit senescence. Senescence is induced in response to many types of cellular stress (Campisi, Eur J Cancer 1997; 33: 703-9; Courtois-Cox et al., Oncogene 2008; 27: 2801-9; Prieur et al., Nature communications 2011; 2: 473; Ramsey et al., Nature cell biology 2006; 8: 1213-5). It has been observed in the context of DNA damage, after multiple cellular replications (aging), in the presence of high levels of cellular reactive oxygen species (ROS), and in association with aberrant expression of oncoproteins such as $Ras^{V12}$ (Kuilman et al., Nature reviews Cancer 2009; 9: 81-94). In the classic view of senescence, the DNA damage response is triggered by one of these events and causes a signaling cascade culminating in irreversible cell cycle arrest. The process is mediated by p53 and RB or through overlapping pathways triggered by high levels of cyclin dependent kinase inhibitors (e.g., p21, p16) or ARF (Campisi, Eur J Cancer 1997; 33: 703-9; Chicas et al., Cancer cell 2010; 17: 376-87; Kuilman et al., Genes & development 2010; 24: 2463-79; Rodier et al. The Journal of cell biology 2011; 192: 547-56). However, knocking down the expression of these proteins in responder cell lines did not affect the ability of PD0332991 to cause senescence (data not shown) arguing against a key role for them in this type of senescence. Nevertheless, senescence is triggered by PSM-Rb in responders, overexpression of CDK4 can inhibit senescence induced in fibroblasts, and inhibiting CDK4 can induce senescence in some cancer cell lines (Michaud et al., Cancer research 2010; 70: 3228; Wiedemeyer et al., 2010; 107: 11501-6; Capparelli et al., Cell Cycle 2012; 11: 3599-610; Puyol et al., Cancer cell 2010; 18: 63-73; and Rane et al., Molecular and cellular biology 2002; 22: 644-56). This is consistent with a model in which CDK4 inhibits senescence via its canonical effect on RB phosphorylation; inhibiting this kinase allows unphosphorylated RB to accumulate on the promoters of E2F target genes and participate in the formation of senescence-associated heterochromatic foci (SAHF) (Narita et al., Cell 2003; 113: 703-16; Adams et al., Molecular cell 2009; 36: 2-14) affecting MDM2 expression.

Nevertheless, RB may not be the sole target by which CDK4 inhibits senescence. Multiple CDK4 targets may cooperate to coordinate the response. For example, Anders et al. (Cancer cell 2011; 20: 620-34) determined that FOXM1 is also a substrate of CDK4, and FOXM1 was required for CDK4-dependent inhibition of senescence. Stable FOXM1 promotes expression of cell cycle genes, a possible mechanism by which it counteracts senescence. Multiple CDK4 targets may cooperate to coordinate the response. Our observations suggest, that a CDK4-dependent quiescent program impinges upon a signaling pathway sensitive to MDM2 levels in quiescent cells. This may represent an additional, novel mechanism by which CDK4 regulates senescence. Whether or not this pathway is intact may determine the nature of a cell's response to PD0332991.

Other senescence pathways that are independent of p53 and INK4A have been described (Lin et al., 2010; Prieur et al., 2011). One is activated by the loss of SKP2 (Lin et al., 2010). This pathway is a classic situation when cells are forced to exit the cell cycle. This is what we expected for senescence induced by CDK4 inhibition because CDK4 drives cell proliferation and prevents senescence in other circumstances (Anders et al., 2011; Puyol et al., 2010; Rane et al., 2002; Zou et al., 2002). Regardless, the scenario we describe here is that the cell chooses between quiescence and senescence, a different developmental choice with a different molecular mechanism.

Another pathway is activated by the loss of the histone acetyl transferase p300 (Prieur et al., 2011). The amount of p300 is reduced in a variety of circumstances that induce senescence, including the overexpression of oncogenic ras. In all cases, hypoacetylation of histone H3/H4 is observed and reducing p300 can lead to this as well. This is probably a common downstream effect of many pathways as it relates to the chromatin condensation state in senescent cells.

How cells choose between quiescent and senescent states is not completely understood. TOR signaling can affect this choice by altering the output of the p53 program (Korotchkina et al., 2010; Leontieva and Blagosklonny, 2013). In contrast, the pathway triggered by MDM2 loss described here is clearly p53-independent. We determined that (i) p53 protein was reduced in these senescent cells, (ii) knocking down p53 did not affect senescence, (iii) cells with p53 mutations were induced to senesce by CDK4 inhibition or reduction of MDM2, and (iv) senescence could be prevented by ectopic expression of an MDM2 protein that cannot bind to p53. The p53 response in these cells is not atypical, because irradiation or treatment of these cells with nutlin-3a triggers growth arrest, p53 accumulation and apoptosis (Ambrosini et al., 2007; Singer et al., 2007). In fact, doxorubicin can induce the accumulation of p53 and the entry of the LS8817 cells into senescence without a reduction in MDM2 levels.

Database mining (Jensen et al., 2009; Stark et al., 2011) indicated that MDM2 can interact with a number of chromatin remodeling enzymes such as PCAF, YY1 and HDAC1 and these may participate as well. While a number of MDM2 binding proteins have been described as noted above, only the apoptotic regulators p53, CAS and HUWE1 have been defined as substrates (Kurokawa et al., 2013; Marine and Lozano, 2010).

CDK4 inhibition is sufficient to trigger the down-regulation of MDM2 in some cell lines but not others. Down-regulation is associated with increased turnover and requires the intrinsic E3 ligase activity of MDM2. The deubiquitinase USP7/HAUSP is the major regulatory mechanism controlling MDM2 turnover by this pathway. However, nonresponders were either missing a critical additional factor or had evolved a way to prevent turnover induced by loss of the interaction or even the down regulation of HAUSP with shRNA.

Consequently, while trying to identify the nature of intrinsic resistance to CDK4 inhibitors, we chanced upon a novel pathway that regulates whether a cell becomes quiescent or senescent. We established that MDM2 is a key player in this pathway. Interestingly, we showed that this pathway is p53- and INK4-independent and dependent on the E3 ligase activity of MDM2.

7.4. References

Adams, P. D. (2009). Healing and hurting: molecular mechanisms, functions, and pathologies of cellular senescence. Molecular cell 36, 2-14.

Ambrosini, G., Sambol, E. B., Carvajal, D., Vassilev, L. T., Singer, S., and Schwartz, G. K. (2007). Mouse double minute antagonist Nutlin-3a enhances chemotherapy-induced apoptosis in cancer cells with mutant p53 by activating E2F1. Oncogene 26, 3473-3481.

Barretina, J., Taylor, B. S., Banerji, S., Ramos, A. H., Lagos-Quintana, M., Decarolis, P. L., Shah, K., Sacci, N. D., Weir, B. A., Ho, A., et al. (2010). Subtype-specific genomic alterations define new targets for soft-tissue sarcoma therapy. Nature genetics 42, 715-721.

Brooks, C. L., and Gu, W. (2009). How does SIRT1 affect metabolism, senescence and cancer? Nature reviews Cancer 9, 123-128.

Campisi, J. (1997). The biology of replicative senescence. Eur J Cancer 33, 703-709.

Campisi, J. (2011). Cellular senescence: putting the paradoxes in perspective. Current opinion in genetics & development 21, 107-112.

Chappell, W. H., Steelman, L. S., Long, J. M., Kempf, R. C., Abrams, S. L., Franklin, R. A., Basecke, J., Stivala, F., Donia, M., Fagone, P., et al. (2011). Ras/Raf/MEK/ERK and PI3K/PTEN/Akt/mTOR inhibitors: rationale and importance to inhibiting these pathways in human health. Oncotarget 2, 135-164.

Chicas, A., Wang, X., Zhang, C., McCurrach, M., Zhao, Z., Mert, O., Dickins, R. A., Narita, M., Zhang, M., and Lowe, S. W. (2010). Dissecting the unique role of the retinoblastoma tumor suppressor during cellular senescence. Cancer cell 17, 376-387.

Ciznadija, D., Zhu, X. H., and Koff, A. (2011). Hdm2- and proteasome-dependent turnover limits p21 accumulation during S phase. Cell Cycle 10, 2714-2723.

Collado, M., and Serrano, M. (2010). Senescence in tumours: evidence from mice and humans. Nature reviews Cancer 10, 51-57.

Coppe, J. P., Desprez, P. Y., Krtolica, A., and Campisi, J. (2010). The senescence-associated secretory phenotype: the dark side of tumor suppression. Annu Rev Pathol 5, 99-118.

Courtois-Cox, S., Jones, S. L., and Cichowski, K. (2008). Many roads lead to oncogene-induced senescence. Oncogene 27, 2801-2809.

Davalos, A. R., Coppe, J. P., Campisi, J., and Desprez, P. Y. (2010). Senescent cells as a source of inflammatory factors for tumor progression. Cancer Metastasis Rev 29, 273-283.

Dean, J. L., McClendon, A. K., Hickey, T. E., Butler, L. M., Tilley, W. D., Witkiewicz, A. K., and Knudsen, E. S. (2012). Therapeutic response to CDK4/6 inhibition in breast cancer defined by ex vivo analyses of human tumors. Cell Cycle 11, 2756-2761.

Dickson, M. A., Tap, W. D., Keohan, M. L., D'Angelo, S. P., Gounder, M. M., Antonescu, C. R., Landa, J., Qin, L. X., Rathbone, D. D., Condy, M. M., et al. (2013). Phase II trial of the CDK4 inhibitor PD0332991 in patients with advanced CDK4-amplified well-differentiated or dedifferentiated liposarcoma. Journal of clinical oncology: official journal of the American Society of Clinical Oncology 31, 2024-2028.

Favaro, E., Bensaad, K., Chong, M. G., Tennant, D. A., Ferguson, D. J., Snell, C., Steers, G., Turley, H., Li, J. L., Gunther, U. L., et al. (2012). Glucose utilization via glycogen phosphorylase sustains proliferation and prevents premature senescence in cancer cells. Cell Metab 16, 751-764.

Foo, R. S., Chan, L. K., Kitsis, R. N., and Bennett, M. R. (2007). Ubiquitination and degradation of the anti-apoptotic protein ARC by MDM2. The Journal of biological chemistry 282, 5529-5535.

Fry, D. W., Harvey, P. J., Keller, P. R., Elliott, W. L., Meade, M., Trachet, E., Albassam, M., Zheng, X., Leopold, W. R., Pryer, N. K., and Toogood, P. L. (2004). Specific inhibition of cyclin-dependent kinase 4/6 by PD 0332991 and associated antitumor activity in human tumor xenografts. Molecular cancer therapeutics 3, 1427-1438.

Guha, M. (2013). Blockbuster dreams for Pfizer's CDK inhibitor. Nat Biotechnol 31, 187.

Halvorsen, Y. D., Bond, A., Sen, A., Franklin, D. M., Lea-Currie, Y. R., Sujkowski, D., Ellis, P. N., Wilkison, W. O., and Gimble, J. M. (2001). Thiazolidinediones and glucocorticoids synergistically induce differentiation of human adipose tissue stromal cells: biochemical, cellular, and molecular analysis. Metabolism: clinical and experimental 50, 407-413.

Haupt, Y., Maya, R., Kazaz, A., and Oren, M. (1997). Mdm2 promotes the rapid degradation of p53. Nature 387, 296-299.

Honda, R., Tanaka, H., and Yasuda, H. (1997). Oncoprotein MDM2 is a ubiquitin ligase E3 for tumor suppressor p53. FEBS Lett 420, 25-27.

Hsieh, J. K., Chan, F. S., O'Connor, D. J., Mittnacht, S., Zhong, S., and Lu, X. (1999). RB regulates the stability and the apoptotic function of p53 via MDM2. Molecular cell 3, 181-193.

Jackman, D. M., Miller, V. A., Cioffredi, L. A., Yeap, B. Y., Janne, P. A., Riely, G. J., Ruiz, M. G., Giaccone, G., Sequist, L. V., and Johnson, 13. E. (2009). Impact of epidermal growth factor receptor and KRAS mutations on clinical outcomes in previously untreated non-small cell lung cancer patients: results of an online tumor registry of clinical trials. Clinical cancer research: an official journal of the American Association for Cancer Research 15, 5267-5273.

Janku, F., Tsimberidou, A. M., Garrido-Laguna, 1., Wang, X., Luthra, R., Hong, D. S., Naing, A., Falchook, G. S., Moroney, J. W., Piha-Paul, S. A., et al. (2011). PIK3CA mutations in patients with advanced cancers treated with PI3K/AKT/mTOR axis inhibitors. Molecular cancer therapeutics 10, 558-565.

Jensen, L. J., Kuhn, M., Stark, M., Chaffron, S., Creevey, C., Muller, J., Doerks, T., Julien, P., Roth, A., Simonovic, M., et al. (2009). STRING 8—a global view on proteins and their functional interactions in 630 organisms. Nucleic acids research 37, D412-416.

Jiang, P., Du, W., Mancuso, A., Wellen, K. E., and Yang, X. (2013). Reciprocal regulation of p53 and malic enzymes modulates metabolism and senescence. Nature 493, 689-693.

Jones, K., Timchenko, L., and Timehenko, N. A. (2012). The role of CUGBP1 in age-dependent changes of liver functions. Ageing Res Rev 11, 442-449.

Khambata-Ford, S., Garrett, C. R., Meropol, N. J., Basik, M., Harbison, C. T., Wu, S., Wong, T. W., Huang, X., Takimoto, C. H., Godwin, A. K., et al. (2007). Expression of epiregulin and amphiregulin and K-ras mutation status predict disease control in metastatic colorectal cancer patients treated with cetuximab. Journal of clinical oncology: official journal of the American Society of Clinical Oncology 25, 3230-3237.

Knudsen, E. S., Buckmaster, C., Chen, T. T., Feramisco, J. R., and Wang, J. Y. (1998). Inhibition of DNA synthesis by RB: effects on G1/S transition and S-phase progression. Genes & development 12, 2278-2292.

Korotchkina, L. G., Leontieva, O. V., Bukreeva, E. I., Demidenko, Z. N., Gudkov, A. V., and Blagosklonny, M. V. (2010). The choice between p53-induced senescence and quiescence is determined in part by the mTOR pathway. Aging 2, 344-352.

Kosar, M., Bartkova, J., Hubackova, S., Hodny, Z., Lukas, J., and Bartek, J. (2011). Senescence-associated heterochromatin foci are dispensable for cellular senescence, occur in a cell type- and insult-dependent manner and follow expression of p16(ink4a). Cell. Cycle 10, 457-468.

Kubbutat, M. H., Jones, S. N., and Vousden, K. H. (1997). Regulation of p53 stability by Mdm2. Nature 387, 299-303.

Kuilman, T., Michaloglou, C., Mooi, W. J., and Peeper, D. S. (2010). The essence of senescence. Genes & development 24, 2463-2479.

Kuilman, T., and Peeper, D. S. (2009). Senescence-messaging secretome: SMS-ing cellular stress. Nature reviews Cancer 9, 81-94.

Lawless, C., Wang, C., Jurk, D., Merz, A., Zglinicki, T., and Passos, J. F. (2010). Quantitative assessment of markers for cell senescence. Exp Gerontol 45, 772-778.

Leach, F. S., Tokino, T., Meltzer, P., Burrell, M., Oliner, J. D., Smith, S., Hill, D. E., Sidransky, D., Kinzler, K. W., and Vogelstein, B. (1993). p53 Mutation and MDM2 amplification in human soft tissue sarcomas. Cancer research 53, 2231-2234.

Li, Q., and Lozano, G. (2013). Molecular pathways: targeting Mdm2 and Mdm4 in cancer therapy. Clinical cancer research: an official journal of the American Association for Cancer Research 19, 34-41.

Loupakis, F., Ruzzo, A., Cremolini, C., Vincenzi, B., Salvatore, L., Santini, D., Masi, G., Stasi, I., Canestrari, E., Rulli, E., et al. (2009). KRAS codon 61, 146 and BRAF mutations predict resistance to cetuximab plus irinotecan in KRAS codon 12 and 13 wild-type metastatic colorectal cancer. British journal of cancer 101, 715-721.

Lujambio, A., Akkari, L., Simon, J., Grace, D., Tschaharganeh, D. F., Bolden, J. E., Zhao, Z., Thapar, V., Joyce, J. A., Krizhanovsky, V., and Lowe, S. W. (2013). Non-cell-autonomous tumor suppression by p53. Cell 153, 449-460.

Malumbres, M., and Barbacid, M. (2009). Cell cycle, CDKs and cancer: a changing paradigm. Nature reviews Cancer 9, 153-166.

Marine, J. C., and Lozano, G. (2010). Mdm2-mediated ubiquitylation: p53 and beyond. Cell Death Differ 17, 93-102.

McCubrey, J. A., Steelman, L. S., Chappell, W. H., Abrams, S. L., Montalto, G., Cervello, M., Nicoletti, F., Fagone, P., Malaponte, G., Mazzarino, M. C., et al. (2012). Mutations and deregulation of Ras/Raf/MEK/ERK and PI3K/PTEN/Akt/mTOR cascades which alter therapy response. Oncotarget 3, 954-987.

McDuff, F. K., and Turner, S. D. (2011). Jailbreak: oncogene-induced senescence and its evasion. Cellular signalling 23, 6-13.

Michaud, K., Solomon, D. A., Oermann, E., Kim, J. S., Zhong, W. Z., Prados, M. D., Ozawa, T., James, C. D., and Waldman, T. (2010). Pharmacologic inhibition of cyclin-dependent kinases 4 and 6 arrests the growth of glioblastoma multiforme intracranial xenografts. Cancer research 70, 3228-3238.

Miller, K. R., Kelley, K., Tuttle, R., and Berberich, S. J. (2010). HdmX overexpression inhibits oncogene induced cellular senescence. Cell Cycle 9, 3376-3382.

Moll, U. M., and Petrenko, O. (2003). The MDM2-p53 interaction. Mol Cancer Res 1, 1001-1008.

Momand, J., Zambetti, G. P., Olson, D. C., George, D., and Levine, A. J. (1992). The mdm-2 oncogene product forms a complex with the p53 protein and inhibits p53-mediated transactivation. Cell 69, 1237-1245.

Narita, M., Nunez, S., Heard, E., Narita, M., Lin, A. W., Hearn, S. A., Spector, D. L., Hannon, G. J., and Lowe, S. W. (2003). Rb-mediated heterochromatin formation and silencing of E2F target genes during cellular senescence. Cell 113, 703-716.

Oliner, J. D., Pietenpol, J. A., Thiagalingam, S., Gyuris, J., Kinzler, K. W., and Vogelstein, B. (1993). Oncoprotein MDM2 conceals the activation domain of tumour suppressor p53. Nature 362, 857-860.

Pearson, M., Carbone, R., Sebastiani, C., Cioce, M., Fagioli, M., Saito, S., Higashimoto, Y., Appella, E., Minucci, S., Pandolfi, P. P., and Pelicci, P. G. (2000). PML regulates p53 acetylation and premature senescence induced by oncogenic Ras. Nature 406, 207-210.

Prieur, A., Besnard, E., Babied, A., and Lemaitre, J. M. (2011). p53 and p16(INK4A) independent induction of senescence by chromatin-dependent alteration of S-phase progression. Nature communications 2, 473.

Puyol, M., Martin, A., Dubus, P., Mulero, F., Pizcueta, P., Khan, G., Guerra, C., Santamaria, D., and Barbacid, M. (2010). A synthetic lethal interaction between K-Ras oncogenes and Cdk4 unveils a therapeutic strategy for non-small cell lung carcinoma. Cancer cell 18, 63-73.

Quijano, C., Cao, L., Fergusson, M. M., Romero, H., Liu, J., Gutkind, S., Rovira, I I, Mohney, R. P., Karoly, E. D., and Finkel, T. (2012). Oncogene-induced senescence results in marked metabolic and bioenergetic alterations. Cell Cycle 11, 1383-1392.

Ramsey, M. R., and Sharpless, N. E. (2006). ROS as a tumour suppressor? Nature cell biology 8, 1213-1215.

Rane, S. G., Cosenza, S. C., Mettus, R. V., and Reddy, E. P. (2002). Germ line transmission of the Cdk4(R24C) mutation facilitates tumorigenesis and escape from cellular senescence. Molecular and cellular biology 22, 644-656.

Rayess, H., Wang, M. B., and Srivatsan, E. S. (2012). Cellular senescence and tumor suppressor gene p16. International journal of cancer Journal international du cancer 130, 1715-1725.

Ringshausen, I., O'Shea, C. C., Finch, A. J., Swigart, L. B., and Evan, G. I. (2006). Mdm2 is critically and continuously required to suppress lethal p53 activity in vivo. Cancer cell 10, 501-514.

Roberts, P. J., Bisi, J. E., Strum, J. C., Combest, A. J., Darr, D. B., Usary, J. E., Zamboni, W. C., Wong, K. K., Perou, C. M., and Sharpless, N. E. (2012). Multiple roles of cyclin-dependent kinase 4/6 inhibitors in cancer therapy. Journal of the National Cancer Institute 104, 476-487.

Rodier, F., and Campisi, J. (2011). Four faces of cellular senescence. The Journal of cell biology 192, 547-556.

Salomoni, P., and Pandolfi, P. P. (2002). The role of PML in tumor suppression. Cell 108, 165-170.

Scaglioni, P. P., Rabellino, A., Yung, T. M., Bernardi, R., Choi, S., Konstantinidou, G., Nardella, C., Cheng, K., and Pandolfi, P. P. (2012). Translation-dependent mechanisms lead to PML upregulation and mediate oncogenic K-RAS-induced cellular senescence. EMBO Mol Med 4, 594-602.

Schwartz, G. K., LoRusso, P. M., Dickson, M. A., Randolph, S. S., Shaik, M. N., Wilner, K. D., Courtney, R., and O'Dwyer, P. J. (2011). Phase I study of PD 0332991, a cyclin-dependent kinase inhibitor, administered in 3-week cycles (Schedule 2/1). British journal of cancer 104, 1862-1868.

Serrano, M., Lin, A. W., McCurrach, M. E., Beach, D., and Lowe, S. W. (1997). Oncogenic ras provokes premature cell senescence associated with accumulation of p53 and p16INK4a. Cell 88, 593-602.

Singer, S., Socci, N. D., Ambrosini, G., Sambol, E., Decarolis, P., Wu, Y., O'Connor, R., Maki, R., Viale, A., Sander, C., et al. (2007). Gene expression profiling of liposarcoma identifies distinct biological types/subtypes and potential therapeutic targets in well-differentiated and dedifferentiated liposarcoma. Cancer research 67, 6626-6636.

Sperka, T., Wang, J., and Rudolph, K. L. (2012). DNA damage checkpoints in stem cells, ageing and cancer. Nature reviews Molecular cell biology 13, 579-590.

Stark, C., Breitkreutz, B. J., Chatr-Aryamontri, A., Boucher, L., Oughtred, R., Livstone, M. S., Nixon, J., Van Auken, K., Wang, X., Shi, X., et al. (2011). The BioGRID Interaction Database: 2011 update. Nucleic acids research 39, D698-704.

Steelman, L. S., Chappell, W. H., Abrams, S. L., Kempf, R. C., Long, J., Laidler, P., Mijatovic, S., Maksimovic-Ivanic, D., Stivala, F., Mazzarino, M. C., et al. (2011). Roles of the Raf/MEK/ERK and PI3K/PTEN/Akt/mTOR pathways in controlling growth and sensitivity to therapy-implications for cancer and aging. Aging 3, 192-222.

Talluri, S., and Dick, F. A. (2012). Regulation of transcription and chromatin structure by pRB: here, there and everywhere. Cell Cycle 11, 3189-3198.

Taylor, B. S., Barretina, J., Socci, N. D., Decarolis, P., Ladanyi, M., Meyerson, M., Singer, S., and Sander, C. (2008). Functional copy-number alterations in cancer. PloS one 3, e3179.

Tchkonia, T., Zhu, Y., van Deursen, J., Campisi, J., and Kirkland, J. L. (2013). Cellular senescence and the senescent secretory phenotype: therapeutic opportunities. The Journal of clinical investigation 123, 966-972.

Teicher, 13. A. (2012). Searching for molecular targets in sarcoma. Biochem Pharmacol 84, 1-10.

Thangavel, C., Dean, J. L., Ertel, A., Knudsen, K. E., Aldaz, C. M., Witkiewicz, A. K., Clarke, R., and Knudsen, E. S. (2011). Therapeutically activating RB: reestablishing cell cycle control in endocrine therapy-resistant breast cancer. Endocrine-related cancer 18, 333-345.

Van Cutsem, E., Kohne, C. H., Hitre, E., Zaluski, J., Chang Chien, C. R., Makhson, A., D'Haens, G., Pinter, T., Lim, R., Bodoky, G., et al. (2009). Cetuximab and chemotherapy as initial treatment for metastatic colorectal cancer. The New England journal of medicine 360, 1408-1417.

Varmeh, S., Egia, A., McGrouther, D., Tahan, S. R., Bayat, A., and Pandolfi, P. P. (2011). Cellular senescence as a possible mechanism for halting progression of keloid lesions. Genes Cancer 2, 1061-1066.

Wawrzynow, B., Zylicz, A., Wallace, M., Hupp, T., and Zylicz, M. (2007). MDM2 chaperones the p53 tumor suppressor. The Journal of biological chemistry 282, 32603-32612.

Wiedemeyer, W. R., Dunn, I. F., Quayle, S. N., Zhang, J., Chheda, M. G., Dunn, G. P., Zhuang, L., Rosenbluh, J., Chen, S., Xiao, Y., et al, (2010). Pattern of retinoblastoma pathway inactivation dictates response to CDK4/6 inhibition in GBM. Proceedings of the National Academy of Sciences of the United States of America 107, 11501-11506.

Wolyniec, K., Shortt, J., de Stanchina, E., Levav-Cohen, Y., Alsheich-Bartok, O., Louria-Hayon, I., Corneille, V., Kumar, B., Woods, S. J., Opat, S., et al. (2012). E6AP ubiquitin ligase regulates PML-induced senescence in Myc-driven lymphomagenesis. Blood 120, 822-832.

Xiao, Z. X., Chen, J., Levine, A. J., Modjtahedi, N., Xing, J., Sellers, W. R., and Livingston, D. M. (1995). Interaction between the retinoblastoma protein and the oncoprotein MDM2. Nature 375, 694-698.

Yap, D. B., Hsieh, J. K., Chan, F. S., and Lu, X. (1999). mdm2: a bridge over the two tumour suppressors, p53 and Rb. Oncogene 18, 7681-7689.

Zezula, J., Casaccia-Bonnefil, P., Ezhevsky, S. A., Osterhout, D. J., Levine, J. M., Dowdy, S. F., Chao, M. V., and Koff, A. (2001). p21cip1 is required for the differentiation of oligodendrocytes independently of cell cycle withdrawal. EMBO reports 2, 27-34.

Zou, X., Ray, D., Aziyu, A., Christov, K., Boiko, A. D., Gudkov, A. V., and Kiyokawa, H. (2002). Cdk4 disruption renders primary mouse cells resistant to oncogenic transformation, leading to Arf/p53-independent senescence. Genes & development 16, 2923-2934.

Various references are cited herein, the contents of which are hereby incorporated by reference in their entireties.

---

What is claimed is:

1. A method for treating a subject having a cancer selected from the group consisting of liposarcoma, breast cancer, glioma and glioblastoma, comprising obtaining a sample of the cancer before treatment of the subject with a CDK4 inhibitor selected from the group consisting of an ATP-competitive inhibitor of CDK4, pyridopyrimidine compounds, pyrrolopyrimidine compounds, indolocarbazole compounds, Palbociclib Isethionate, LEE011, LY2835219, PD0332991, Flavopiridol Hydrochloride, an antisense oligonucleotide that inhibits the expression or activity of CDK4, a shRNA molecule that inhibits the expression or activity of CDK4, a siRNA molecule that inhibits the expression or activity of CDK4 and combinations thereof, and determining, in one or more cancer cells from the sample, the effect of treatment with the CDK4 inhibitor on the expression level of a MDM2 biomarker, where if the MDM2 biomarker expression level is decreased following treatment with the CDK4 inhibitor, then initiating treatment of the subject with a therapeutically effective amount of the CDK4 inhibitor.

2. The method of claim 1, where the cancer is a liposarcoma.

3. The method of claim 1, where the cancer is a glioma or glioblastoma.

4. The method of claim 1, where the cancer is a breast cancer.

5. A method for treating a subject having a cancer selected from the group consisting of liposarcoma, breast cancer, glioma and glioblastoma, comprising, obtaining a sample of the cancer after treatment with a CDK4 inhibitor selected from the group consisting of an ATP-competitive inhibitor of CDK4, pyridopyrimidine compounds, pyrrolopyrimidine compounds, indolocarbazole compounds Palbociclib Isethionate, LEE011, LY2835219, PD0332991, Flavopiridol Hydrochloride, an antisense oligonucleotide that inhibits the expression or activity of CDK4, a shRNA molecule that inhibits the expression or activity of CDK4, a siRNA molecule that inhibits the expression or activity of CDK4 and combinations thereof, and determining, in the sample, the expression level of a MDM2 biomarker, where if the MDM2 biomarker expression level, when compared to a reference standard level, is decreased following treatment with a CDK4 inhibitor, then continuing or resuming treatment of the subject with a therapeutically effective amount of a CDK4 inhibitor.

6. The method of claim 5, where the reference standard level is the level of the MDM2 biomarker in a sample of the cancer prior to treatment with a CDK4 inhibitor.

7. The method of claim 5, where the reference standard level is the level of the MDM2 biomarker in a parallel culture of the subject's cancer cells.

8. The method of claim 5, where the cancer is a liposarcoma.

9. The method of claim 5, where the cancer is a glioma or glioblastoma.

10. The method of claim 5, where the cancer is a breast cancer.

* * * * *

SEQUENCE LISTING

```
<160> NUMBER OF SEQ ID NOS: 10

<210> SEQ ID NO 1
<211> LENGTH: 497
<212> TYPE: PRT
<213> ORGANISM: Homo sapiens

<400> SEQUENCE: 1

Met Val Arg Ser Arg Gln Met Cys Asn Thr Asn Met Ser Val Pro Thr
1               5                   10                  15

Asp Gly Ala Val Thr Thr Ser Gln Ile Pro Ala Ser Glu Gln Glu Thr
            20                  25                  30

Leu Val Arg Pro Lys Pro Leu Leu Leu Lys Leu Leu Lys Ser Val Gly
        35                  40                  45

Ala Gln Lys Asp Thr Tyr Thr Met Lys Glu Val Leu Phe Tyr Leu Gly
    50                  55                  60

Gln Tyr Ile Met Thr Lys Arg Leu Tyr Asp Glu Lys Gln Gln His Ile
65                  70                  75                  80

Val Tyr Cys Ser Asn Asp Leu Leu Gly Asp Leu Phe Gly Val Pro Ser
                85                  90                  95

Phe Ser Val Lys Glu His Arg Lys Ile Tyr Thr Met Ile Tyr Arg Asn
            100                 105                 110

Leu Val Val Val Asn Gln Gln Glu Ser Ser Asp Ser Gly Thr Ser Val
        115                 120                 125

Ser Glu Asn Arg Cys His Leu Glu Gly Gly Ser Asp Gln Lys Asp Leu
```

```
                    130                 135                 140
Val Gln Glu Leu Gln Glu Glu Lys Pro Ser Ser Ser His Leu Val Ser
145                 150                 155                 160

Arg Pro Ser Thr Ser Arg Arg Arg Ala Ile Ser Glu Thr Glu Glu
                165                 170                 175

Asn Ser Asp Glu Leu Ser Gly Glu Arg Gln Arg Lys Arg His Lys Ser
                180                 185                 190

Asp Ser Ile Ser Leu Ser Phe Asp Glu Ser Leu Ala Leu Cys Val Ile
                195                 200                 205

Arg Glu Ile Cys Cys Glu Arg Ser Ser Ser Glu Ser Thr Gly Thr
        210                 215                 220

Pro Ser Asn Pro Asp Leu Asp Ala Gly Val Ser Glu His Ser Gly Asp
225                 230                 235                 240

Trp Leu Asp Gln Asp Ser Val Ser Asp Gln Phe Ser Val Glu Phe Glu
                245                 250                 255

Val Glu Ser Leu Asp Ser Glu Asp Tyr Ser Leu Ser Glu Glu Gly Gln
                260                 265                 270

Glu Leu Ser Asp Glu Asp Asp Glu Val Tyr Gln Val Thr Val Tyr Gln
        275                 280                 285

Ala Gly Glu Ser Asp Thr Asp Ser Phe Glu Glu Asp Pro Glu Ile Ser
290                 295                 300

Leu Ala Asp Tyr Trp Lys Cys Thr Ser Cys Asn Glu Met Asn Pro Pro
305                 310                 315                 320

Leu Pro Ser His Cys Asn Arg Cys Trp Ala Leu Arg Glu Asn Trp Leu
                325                 330                 335

Pro Glu Asp Lys Gly Lys Asp Lys Gly Glu Ile Ser Glu Lys Ala Lys
                340                 345                 350

Leu Glu Asn Ser Thr Gln Ala Glu Glu Gly Phe Asp Val Pro Asp Cys
                355                 360                 365

Lys Lys Thr Ile Val Asn Asp Ser Arg Glu Ser Cys Val Glu Glu Asn
        370                 375                 380

Asp Asp Lys Ile Thr Gln Ala Ser Gln Ser Gln Glu Ser Glu Asp Tyr
385                 390                 395                 400

Ser Gln Pro Ser Thr Ser Ser Ile Ile Tyr Ser Gln Glu Asp
                405                 410                 415

Val Lys Glu Phe Glu Arg Glu Thr Gln Asp Lys Glu Glu Ser Val
                420                 425                 430

Glu Ser Ser Leu Pro Leu Asn Ala Ile Glu Pro Cys Val Ile Cys Gln
                435                 440                 445

Gly Arg Pro Lys Asn Gly Cys Ile Val His Gly Lys Thr Gly His Leu
        450                 455                 460

Met Ala Cys Phe Thr Cys Ala Lys Lys Leu Lys Lys Arg Asn Lys Pro
465                 470                 475                 480

Cys Pro Val Cys Arg Gln Pro Ile Gln Met Ile Val Leu Thr Tyr Phe
                485                 490                 495

Pro

<210> SEQ ID NO 2
<211> LENGTH: 489
<212> TYPE: PRT
<213> ORGANISM: Mus musculus

<400> SEQUENCE: 2

Met Cys Asn Thr Asn Met Ser Val Ser Thr Glu Gly Ala Ala Ser Thr
```

```
1               5                   10                  15
Ser Gln Ile Pro Ala Ser Glu Gln Glu Thr Leu Val Arg Pro Lys Pro
                20                  25                  30
Leu Leu Leu Lys Leu Lys Ser Val Gly Ala Gln Asn Asp Thr Tyr
                35                  40                  45
Thr Met Lys Glu Ile Ile Phe Tyr Ile Gly Gln Tyr Ile Met Thr Lys
    50                  55                  60
Arg Leu Tyr Asp Glu Lys Gln Gln His Ile Val Tyr Cys Ser Asn Asp
65                  70                  75                  80
Leu Leu Gly Asp Val Phe Gly Val Pro Ser Phe Ser Val Lys Glu His
                85                  90                  95
Arg Lys Ile Tyr Ala Met Ile Tyr Arg Asn Leu Val Ala Val Ser Gln
                100                 105                 110
Gln Asp Ser Gly Thr Ser Leu Ser Glu Ser Arg Arg Gln Pro Glu Gly
                115                 120                 125
Gly Ser Asp Leu Lys Asp Pro Leu Gln Ala Pro Pro Glu Glu Lys Pro
                130                 135                 140
Ser Ser Ser Asp Leu Ile Ser Arg Leu Ser Thr Ser Ser Arg Arg Arg
145                 150                 155                 160
Ser Ile Ser Glu Thr Glu Glu Asn Thr Asp Glu Leu Pro Gly Glu Arg
                165                 170                 175
His Arg Lys Arg Arg Ser Leu Ser Phe Asp Pro Ser Leu Gly Leu
                180                 185                 190
Cys Glu Leu Arg Glu Met Cys Ser Gly Gly Ser Ser Ser Ser Ser
                195                 200                 205
Ser Ser Ser Glu Ser Thr Glu Thr Pro Ser His Gln Asp Leu Asp Asp
210                 215                 220
Gly Val Ser Glu His Ser Gly Asp Cys Leu Asp Gln Asp Ser Val Ser
225                 230                 235                 240
Asp Gln Phe Ser Val Glu Phe Glu Val Glu Ser Leu Asp Ser Glu Asp
                245                 250                 255
Tyr Ser Leu Ser Asp Glu Gly His Glu Leu Ser Asp Glu Asp Asp Glu
                260                 265                 270
Val Tyr Arg Val Thr Val Tyr Gln Thr Gly Glu Ser Asp Thr Asp Ser
                275                 280                 285
Phe Glu Gly Asp Pro Glu Ile Ser Leu Ala Asp Tyr Trp Lys Cys Thr
                290                 295                 300
Ser Cys Asn Glu Met Asn Pro Pro Leu Pro Ser His Cys Lys Arg Cys
305                 310                 315                 320
Trp Thr Leu Arg Glu Asn Trp Leu Pro Asp Asp Lys Gly Lys Asp Lys
                325                 330                 335
Val Glu Ile Ser Glu Lys Ala Lys Leu Glu Asn Ser Ala Gln Ala Glu
                340                 345                 350
Glu Gly Leu Asp Val Pro Asp Gly Lys Lys Leu Thr Glu Asn Asp Ala
                355                 360                 365
Lys Glu Pro Cys Ala Glu Glu Asp Ser Glu Glu Lys Ala Glu Gln Thr
                370                 375                 380
Pro Leu Ser Gln Glu Ser Asp Asp Tyr Ser Gln Pro Ser Thr Ser Ser
385                 390                 395                 400
Ser Ile Val Tyr Ser Ser Gln Glu Ser Val Lys Glu Leu Lys Glu Glu
                405                 410                 415
Thr Gln Asp Lys Asp Glu Ser Val Glu Ser Ser Phe Ser Leu Asn Ala
                420                 425                 430
```

```
Ile Glu Pro Cys Val Ile Cys Gln Gly Arg Pro Lys Asn Gly Cys Ile
        435                 440                 445

Val His Gly Lys Thr Gly His Leu Met Ser Cys Phe Thr Cys Ala Lys
    450                 455                 460

Lys Leu Lys Lys Arg Asn Lys Pro Cys Pro Val Cys Arg Gln Pro Ile
465                 470                 475                 480

Gln Met Ile Val Leu Thr Tyr Phe Asn
                485

<210> SEQ ID NO 3
<211> LENGTH: 458
<212> TYPE: PRT
<213> ORGANISM: Rattus norvegicus

<400> SEQUENCE: 3

Met Cys Asn Thr Asn Met Ser Val Ser Thr Glu Gly Ala Ala Gly Thr
1               5                   10                  15

Ser Gln Ile Pro Ala Ser Glu Gln Glu Thr Leu Ile Ile Phe Tyr Ile
            20                  25                  30

Gly Gln Tyr Ile Met Thr Lys Arg Leu Tyr Asp Glu Lys Gln Gln His
        35                  40                  45

Ile Val Tyr Cys Ser Asn Asp Leu Leu Gly Asp Val Phe Gly Val Pro
    50                  55                  60

Ser Phe Ser Val Lys Glu His Arg Lys Ile Tyr Ala Met Ile Tyr Arg
65                  70                  75                  80

Asn Leu Val Val Ser Gln Gln Asp Ser Gly Thr Ser Pro Ser Glu
                85                  90                  95

Ser Arg Cys Gln Pro Glu Gly Gly Ser Asp Leu Lys Asp Pro Val Gln
            100                 105                 110

Ala Ser Gln Glu Glu Lys Pro Ser Ser Ser Asp Val Val Ser Arg Pro
        115                 120                 125

Ser Thr Ser Ser Arg Arg Arg Ala Ile Ser Glu Thr Glu Glu Asn Thr
    130                 135                 140

Asp Glu Leu Pro Gly Glu Arg Gln Arg Lys Arg His Arg Ala Leu Ser
145                 150                 155                 160

Phe Asp Glu Ser Leu Gly Leu Cys Val Leu Arg Glu Ile Cys Cys Glu
                165                 170                 175

Arg Ser Ser Ser Glu Ala Thr Asp Thr Pro Ser His Gln Asp Leu
            180                 185                 190

Asp Asp Gly Val Ser Asp His Ser Ala Asp Cys Leu Asp Gln Asp Ser
        195                 200                 205

Val Ser Asp Gln Phe Ser Val Glu Phe Glu Val Glu Ser Leu Asp Ser
    210                 215                 220

Glu Asp Tyr Ser Leu Ser Asp Glu Gly His Glu Leu Ser Asp Glu Asp
225                 230                 235                 240

Asp Glu Val Tyr Arg Val Thr Val Tyr Gln Ala Gly Glu Ser Asp Ala
                245                 250                 255

Asp Ser Phe Glu Gly Asp Pro Glu Ile Ser Leu Ala Asp Tyr Trp Lys
            260                 265                 270

Cys Thr Ser Cys Asn Glu Met Asn Pro Pro Leu Pro Ser His Cys Asn
        275                 280                 285

Arg Cys Trp Thr Leu Arg Glu Asn Trp Leu Pro Asp Asp Lys Gly Lys
    290                 295                 300

Asp Lys Val Glu Ile Ser Glu Lys Ala Lys Leu Glu Ser Ser Asp Gln
```

```
            305                 310                 315                 320
Ala Glu Glu Gly Leu Asp Val Pro Asp Gly Lys Lys Val Thr Glu Asp
                    325                 330                 335

Asp Ala Lys Glu Ser Ala Glu Asp Ser Glu Glu Lys Val Ala Gln
                340                 345                 350

Met Leu Leu Ser Gln Glu Ser Asp Asp Tyr Ser Gln Pro Ser Thr Ser
            355                 360                 365

Ser Ser Ile Val Tyr Ser Ser Gln Glu Ser Gly Lys Glu Leu Lys Glu
        370                 375                 380

Asp Thr Gln Asp Lys Glu Glu Ser Met Glu Ser Ser Phe Ser Leu Asn
385                 390                 395                 400

Ala Ile Glu Pro Cys Val Ile Cys Gln Gly Arg Pro Lys Asn Gly Cys
                405                 410                 415

Ile Val His Gly Lys Thr Gly His Leu Met Ser Cys Phe Thr Cys Ala
                420                 425                 430

Lys Lys Leu Lys Lys Arg Asn Lys Pro Cys Pro Val Cys Arg Gln Pro
            435                 440                 445

Ile Gln Met Ile Val Leu Thr Tyr Phe Asn
    450                 455

<210> SEQ ID NO 4
<211> LENGTH: 21
<212> TYPE: DNA
<213> ORGANISM: Artificial Sequence
<220> FEATURE:
<223> OTHER INFORMATION: CDK4 shRNA

<400> SEQUENCE: 4
gagattactt tgctgcctta a                                              21

<210> SEQ ID NO 5
<211> LENGTH: 21
<212> TYPE: DNA
<213> ORGANISM: Artificial Sequence
<220> FEATURE:
<223> OTHER INFORMATION: MDM2 shRNA (M376)

<400> SEQUENCE: 5
ttcactattc cactaccaaa g                                              21

<210> SEQ ID NO 6
<211> LENGTH: 21
<212> TYPE: DNA
<213> ORGANISM: Artificial Sequence
<220> FEATURE:
<223> OTHER INFORMATION: MDM2 shRNA (M380)

<400> SEQUENCE: 6
tactagaagt tgatggctga g                                              21

<210> SEQ ID NO 7
<211> LENGTH: 21
<212> TYPE: DNA
<213> ORGANISM: Artificial Sequence
<220> FEATURE:
<223> OTHER INFORMATION: HAUSP shRNA (4057)

<400> SEQUENCE: 7
ccagctaagt atcaaaggaa a                                              21

<210> SEQ ID NO 8
```

```
<211> LENGTH: 21
<212> TYPE: DNA
<213> ORGANISM: Artificial Sequence
<220> FEATURE:
<223> OTHER INFORMATION: HAUSP shRNA (845)

<400> SEQUENCE: 8
cgtggtgtca aggtgtacta a                                              21

<210> SEQ ID NO 9
<211> LENGTH: 21
<212> TYPE: DNA
<213> ORGANISM: Artificial Sequence
<220> FEATURE:
<223> OTHER INFORMATION: CDK6 shRNA

<400> SEQUENCE: 9
gacctggaaa ggtgcaaaga a                                              21

<210> SEQ ID NO 10
<211> LENGTH: 24
<212> TYPE: DNA
<213> ORGANISM: Artificial Sequence
<220> FEATURE:
<223> OTHER INFORMATION: MDM2 shRNA (mismatch)

<400> SEQUENCE: 10
actattctca accctcaact tcta                                           24
```